(12) United States Patent
Pfefferkorn et al.

(10) Patent No.: US 8,389,552 B2
(45) Date of Patent: *Mar. 5, 2013

(54) (S)-6-(2-(4-(CYCLOBUTYLSULFONYL)-1H-IMIDAZOL-1-YL)-3-CYCLOPENTYL-PROPANAMIDO)NICOTINIC ACID USEFUL AS A GLUCOKINASE ACTIVATOR

(75) Inventors: Jeffrey Allen Pfefferkorn, Mystic, CT (US); Meihua Mike Tu, Mystic, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/453,292

(22) Filed: Apr. 23, 2012

(65) Prior Publication Data

US 2012/0225910 A1 Sep. 6, 2012

Related U.S. Application Data

(60) Continuation of application No. 13/116,398, filed on May 26, 2011, now Pat. No. 8,329,920, which is a division of application No. 12/556,086, filed on Sep. 9, 2009, now Pat. No. 7,977,367.

(60) Provisional application No. 61/232,578, filed on Aug. 10, 2009.

(51) Int. Cl.
*A61K 31/44* (2006.01)
(52) U.S. Cl. ........................ 514/356; 546/318; 548/335.1
(58) Field of Classification Search .................. 514/356; 546/318; 548/335.1
See application file for complete search history.

(56) References Cited

U.S. PATENT DOCUMENTS

| 4,404,214 | A | 9/1983 | Takeda et al. |
|---|---|---|---|
| 5,972,936 | A | 10/1999 | Dyke et al. |
| 6,066,657 | A | 5/2000 | Dyke et al. |
| 6,117,874 | A | 9/2000 | Dombroski et al. |
| 6,121,274 | A | 9/2000 | Ulrich et al. |
| 6,133,286 | A | 10/2000 | Dombroski et al. |
| 6,211,203 | B1 | 4/2001 | Amschler |
| 7,842,713 | B2 | 11/2010 | Bai et al. |
| 8,071,606 | B2 | 12/2011 | Benbow et al. |
| 8,119,624 | B2 | 2/2012 | Bai et al. |
| 2003/0139402 | A1 | 7/2003 | Konradi et al. |
| 2004/0138286 | A1 | 7/2004 | Imazaki et al. |
| 2004/0147512 | A1 | 7/2004 | Konradi et al. |
| 2004/0214868 | A1 | 10/2004 | Hayter et al. |
| 2005/0026969 | A1 | 2/2005 | Cheng et al. |
| 2005/0113420 | A1 | 5/2005 | Nan et al. |
| 2006/0058353 | A1 | 3/2006 | Mckerrecher et al. |
| 2006/0142269 | A1 | 6/2006 | Dykes |
| 2006/0148888 | A1 | 7/2006 | Krauss et al. |
| 2006/0167053 | A1 | 7/2006 | Iino et al. |
| 2006/0205751 | A1 | 9/2006 | Lee et al. |
| 2006/0258701 | A1 | 11/2006 | Mitsuya et al. |
| 2006/0287291 | A1 | 12/2006 | Johansson et al. |
| 2007/0213349 | A1 | 9/2007 | Cheruvallath et al. |
| 2011/0039821 | A1 | 2/2011 | Bai et al. |

FOREIGN PATENT DOCUMENTS

| EP | 0606489 | 7/1994 |
|---|---|---|
| EP | 1433778 | 6/2004 |
| EP | 1532980 | 5/2005 |
| JP | 2006177436 | 7/2006 |
| WO | 9304580 | 3/1993 |
| WO | 9610016 | 9/1996 |
| WO | 9728133 | 8/1997 |
| WO | 0066557 | 11/2000 |
| WO | 0220463 | 3/2002 |
| WO | 0240448 | 5/2002 |
| WO | 0246173 | 6/2002 |
| WO | 02051836 | 7/2002 |
| WO | 03035621 | 5/2003 |
| WO | 03068230 | 8/2003 |
| WO | 03092670 | 11/2003 |
| WO | 03106427 | 12/2003 |
| WO | 2004046139 | 6/2004 |
| WO | 2004072066 | 8/2004 |
| WO | 2004074262 | 9/2004 |
| WO | 2005018557 | 3/2005 |
| WO | 2005095418 | 10/2005 |
| WO | 2006015159 | 2/2006 |
| WO | 2006028833 | 3/2006 |
| WO | 2006030031 | 3/2006 |
| WO | 2006098683 | 9/2006 |
| WO | 2006106326 | 10/2006 |
| WO | 2007022380 | 2/2007 |
| WO | 2007026761 | 3/2007 |
| WO | 2007043638 | 4/2007 |
| WO | 2007058580 | 5/2007 |
| WO | 2007117995 | 10/2007 |
| WO | 2008079787 | 7/2008 |
| WO | 2008120754 | 10/2008 |
| WO | 2008149382 | 12/2008 |

OTHER PUBLICATIONS

Sarabu, et al., "Glucokinase activators as new type 2 diabetes therapeutic agents", Expert Opinion on Therapeutic Patents, vol. 18(7), pp. 759-768 (2008).
Janusz et al., "New cyclooxygenase-2/5-Lipoxygenase Inhibitors.3. 7-tert/Butyl-2,3-dihydro-3,3-dimethylbenzoforan Derivatives as Gastrointestinal Safe Antiinflammatory and Analgesic Agents: Variations at the 5 position", J. Med. Chem., vol. 41, pp. 3515-3529 (1998).

(Continued)

*Primary Examiner* — Douglas M Willis
(74) *Attorney, Agent, or Firm* — James T. Wasicak

(57) ABSTRACT

The present invention provides Formula (1A) compounds

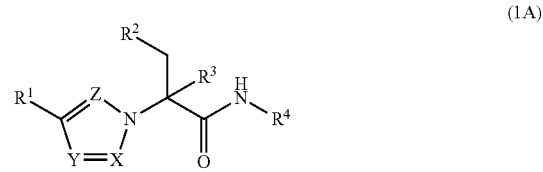

(1A)

that act as glucokinase activators; pharmaceutical compositions thereof; and methods of treating diseases, disorders, or conditions mediated by glucokinase. X, Y, Z, $R^1$, $R^2$, $R^3$, and $R^4$ areas described herein.

3 Claims, No Drawings

OTHER PUBLICATIONS

Moller, "New drug targets for Type II diabetes and the metabolic syndrome", Nature, vol. 414, pp. 821-827 (2001).

Fyfe, et al., "Glucokinase activator PSN-GK1 displays enhanced antihyperglycaemic and insulinotropic actions", Diabetologia, vol. 50, pp. 1277-1287 (2007).

Jordan, "Tamoxifen: A Most Unlikely Pioneering Medicine", Nature Reviews: Drug Discovery, vol. 2, pp. 205-213 (2003).

Hackam, et al., "Translation of Research Evidence From Animals to Humans", JAMA, vol. 296(14), pp. 1731-1732 (2006).

Krause, et al., "N-Terminal pyrazinones: a new class of peptide-bound advanced glycation and end-products", Amino Acids, vol. 27(1), pp. 9-18 (2004).

(S)-6-(2-(4-(CYCLOBUTYLSULFONYL)-1H-IMIDAZOL-1-YL)-3-CYCLOPENTYL-PROPANAMIDO)NICOTINIC ACID USEFUL AS A GLUCOKINASE ACTIVATOR

This application is a continuation of U.S. application Ser. No. 13/116,398 filed May 26, 2011 now U.S. Pat. No. 8,329,920, which is a divisional of U.S. application Ser. No. 12/556,086 filed Sep. 09, 2009 now U.S. Pat. No. 7,977,367 issued Jul. 12, 2011, which claims the benefit of priority from U.S. Provisional Application No. 61/232,578, filed Aug. 10, 2009.

FIELD OF THE INVENTION

The present invention relates to substituted heteroaryls and the uses thereof as glucokinase activators.

BACKGROUND

Diabetes is a major public health concern because of its increasing prevalence and associated health risks. The disease is characterized by metabolic defects in the production and utilization of carbohydrates which result in the failure to maintain appropriate blood glucose levels. Two major forms of diabetes are recognized. Type I diabetes, or insulin-dependent diabetes mellitus (IDDM), is the result of an absolute deficiency of insulin. Type II diabetes, or non-insulin dependent diabetes mellitus (NIDDM), often occurs with normal, or even elevated levels of insulin and appears to be the result of the inability of tissues and cells to respond appropriately to insulin. Aggressive control of NIDDM with medication is essential; otherwise it can progress into IDDM.

As blood glucose increases, it is transported into pancreatic beta cells via a glucose transporter. Intracellular mammalian glucokinase (GK) senses the rise in glucose and activates cellular glycolysis, i.e. the conversion of glucose to glucose-6-phosphate, and subsequent insulin release. Glucokinase is found principally in pancreatic β-cells and liver parenchymal cells. Because transfer of glucose from the blood into muscle and fatty tissue is insulin dependent, diabetics lack the ability to utilize glucose adequately which leads to undesired accumulation of blood glucose (hyperglycemia). Chronic hyperglycemia leads to decreases in insulin secretion and contributes to increased insulin resistance. Glucokinase also acts as a sensor in hepatic parenchymal cells which induces glycogen synthesis, thus preventing the release of glucose into the blood. The GK processes are thus critical for the maintenance of whole body glucose homeostasis.

It is expected that an agent that activates cellular GK will facilitate glucose-dependent secretion from pancreatic beta cells, correct postprandial hyperglycemia, increase hepatic glucose utilization and potentially inhibit hepatic glucose release. Consequently, a GK activator may provide therapeutic treatment for NIDDM and associated complications, inter alia, hyperglycemia, dyslipidemia, insulin resistance syndrome, hyperinsulinemia, hypertension, and obesity.

Several drugs in five major categories, each acting by different mechanisms, are available for treating hyperglycemia and subsequently, NIDDM (Moller, D. E., "New drug targets for Type II diabetes and the metabolic syndrome" Nature 414; 821-827, (2001)): (A) Insulin secretogogues, including sulphonyl-ureas (e.g., glipizide, glimepiride, glyburide) and meglitinides (e.g., nateglidine and repaglinide) enhance secretion of insulin by acting on the pancreatic beta-cells. While this therapy can decrease blood glucose level, it has limited efficacy and tolerability, causes weight gain and often induces hypoglycemia. (B) Biguanides (e.g., metformin) are thought to act primarily by decreasing hepatic glucose production. Biguanides often cause gastrointestinal disturbances and lactic acidosis, further limiting their use. (C) Inhibitors of alpha-glucosidase (e.g., acarbose) decrease intestinal glucose absorption. These agents often cause gastrointestinal disturbances. (D) Thiazolidinediones (e.g., pioglitazone, rosiglitazone) act on a specific receptor (peroxisome proliferator-activated receptor-gamma) in the liver, muscle and fat tissues. They regulate lipid metabolism subsequently enhancing the response of these tissues to the actions of insulin. Frequent use of these drugs may lead to weight gain and may induce edema and anemia. (E) Insulin is used in more severe cases, either alone or in combination with the above agents.

Ideally, an effective new treatment for NIDDM would meet the following criteria: (a) it would not have significant side effects including induction of hypoglycemia; (b) it would not cause weight gain; (c) it would at least partially replace insulin by acting via mechanism(s) that are independent from the actions of insulin; (d) it would desirably be metabolically stable to allow less frequent usage; and (e) it would be usable in combination with tolerable amounts of any of the categories of drugs listed herein.

Substituted heteroaryls, particularly pyridones, have been implicated in mediating GK and may play a significant role in the treatment of NIDDM. For example, U.S. Patent publication No. 2006/0058353 and PCT publication Nos. WO2007/043638, WO2007/043638, and WO2007/117995 recite certain heterocyclic derivatives with utility for the treatment of diabetes. Although investigations are on-going, there still exists a need for a more effective and safe therapeutic treatment for diabetes, particularly NIDDM.

SUMMARY OF THE INVENTION

The present invention provides Formula (1A) compounds that act as glucokinase modulators, in particular, glucokinase activators; therefore, may be used in the treatment of diseases mediated by such activation (e.g., diseases related to Type 2 diabetes, and diabetes-related and obesity-related co-morbidities).

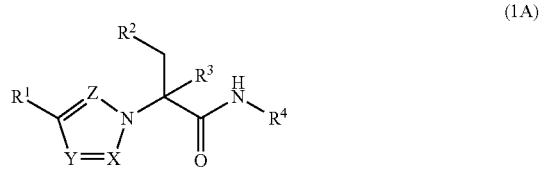

(1A)

wherein

X, Y, and Z are each independently C(R) or N, where R is H, halo, halo-substituted ($C_1$-$C_3$)alkyl, ($C_1$-$C_6$)alkyl, or ($C_1$-$C_6$)alkoxy, and X, Y, and Z are not all N;

$R^1$ is H, ($C_1$-$C_6$)alkyl, halo-substituted ($C_1$-$C_3$)alkyl, —S(O)$_2$($R^{1a}$), or C(O)$R^{1a}$, where $R^{1a}$ is ($C_1$-$C_6$)alkyl, ($C_3$-$C_6$)cycloalkyl, ($C_1$-$C_3$)alkylamino, or di-($C_1$-$C_3$)alkylamino;

$R^2$ is ($C_3$-$C_6$)cycloalkyl or 5- to 6-membered heterocycle containing one N, O, or S heteroatom, where said cycloalkyl and said heterocycle are optionally substituted with one to two substituents each independently halo, ($C_1$-$C_6$)alkyl, ($C_1$-$C_6$)alkoxy, —$CF_3$, or cyano;

$R^3$ is H or ($C_1$-$C_6$)alkyl; and $R^4$ is quinolinyl, thiazolo[5,4-b]pyridinyl or 5- to 6-membered heteroaryl containing one to two N heteroatoms and optionally one O or S heteroatom, where said heteroaryl, quinolinyl and thiazolo[5,4-b]pyridinyl are optionally substituted with one to two $R^{4a}$, where each $R^{4a}$ is independently ($C_1$-$C_6$)alkyl optionally substituted with one to three hydroxy, —$CF_3$, cyano, ($C_1$-$C_6$)alkoxy, halo, amino, ($C_1$-$C_3$) alkylamino, di-($C_1$-$C_3$)alkylamino, —$CO_2R^{4b}$, —($C_1$-$C_6$) alkyl$CO_2R^{4b}$, —$C(O)N(R^{4b})_2$, —$P(O)(OR_{4b})_2$, —($C_1$-$C_6$) alkyl$P(O)(OR_{4b})_2$, —$P(O)(OR^{4b})(C_1$-$C_3$alkyl), ($C_1$-$C_3$) alkylsufonyl, —$SO_3H$, —$NHC(O)R^{4c}$ or aryl($C_1$-$C_6$)alkyl, where the aryl of said arylalkyl is optionally substituted with ($C_1$-$C_6$)alkyl, —$CF_3$, cyano, ($C_1$-$C_6$)alkoxy, halo, amino, ($C_1$-$C_3$)alkylamino, or di-($C_1$-$C_3$)alkylamino;

$R^{4b}$ at each occurrence is independently hydrogen, ($C_1$-$C_6$) alkyl or benzyl; and $R^{4c}$ at each occurrence is independently $CO_2H$ or ($C_1$-$C_6$)alkyl optionally substituted with one to three hydroxy; or a pharmaceutically acceptable salt thereof.

$R^1$ is preferably H, methyl, ethyl, —$CF_3$, —$S(O)_2(R^{1a})$, or $C(O)R^{1a}$, where $R^{1a}$ is methyl, ethyl, isopropyl, cyclopropyl, cyclobutyl, ($C_1$-$C_3$)alkylamino, or di-($C_1$-$C_3$)alkylamino. More preferred, $R^1$ is H, methyl, ethyl, —$CF_3$, —$S(O)_2CH_3$, —$S(O)_2CH_2CH_3$, —$S(O)_2CH(CH_3)_2$, —$S(O)_2$cyclopropyl, —$S(O)_2$cyclobutyl, —$C(O)NHCH_3$, —$C(O)NHCH_2CH_3$, or —$C(O)N(CH_3)_2$. Most preferred, $R^1$ is H, methyl, —$CF_3$, —$S(O)_2CH_3$, —$S(O)_2CH_2CH_3$, —$S(O)_2CH(CH_3)_2$, —$S(O)_2$cyclobutyl, or —$C(O)N(CH_3)_2$.

$R^2$ is preferably ($C_3$-$C_6$)cycloalkyl or 5- to 6-membered heterocycle containing one N, O, or S heteroatom, where said cycloalkyl and said heterocycle are optionally substituted with halo, ($C_1$-$C_6$)alkyl, ($C_1$-$C_6$)alkoxy, —$CF_3$, or cyano. More preferred, $R^2$ is cyclobutyl, cyclopentyl, cyclohexyl, tetrahydrofuranyl, or tetrahydropyranyl, each optionally substituted with halo, ($C_1$-$C_6$)alkyl, ($C_1$-$C_6$)alkoxy, —$CF_3$, or cyano. Most preferred, $R^2$ is cyclopentyl or tetrahydropyranyl.

$R^3$ is preferably H, methyl, or ethyl. Most preferred, $R^3$ is H.

$R^4$ is preferably pyrrolyl, pyrazolyl, imidazolyl, isoxazolyl, oxazolyl, isothiazolyl, thiazolyl, pyridinyl, pyridazinyl, pyrimidinyl, pyrazinyl, or quinolinyl, each optionally substituted with one to two $R^{4a}$, where $R^{4a}$ is as described above. More preferred, $R^4$ is pyrazolyl, isoxazolyl, pyridinyl, pyrazinyl, pyrimidinyl, quinolinyl, each optionally substituted with one to two $R^{4a}$, where $R^{4a}$ is as described above. Most preferred, $R^4$ is pyrazolyl, isoxazolyl, pyridinyl, pyrazinyl, pyrimidinyl, quinolinyl, or a Formula of (a), (b), (c), (d), or (e), (a)
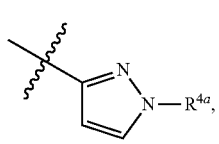

(b)
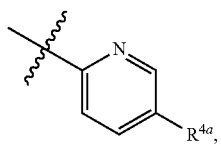

(c)
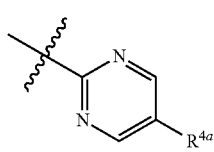

(d)
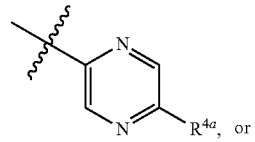

(e)
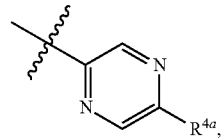

where $R^{4a}$ is methyl, ethyl, —$CF_3$, —$CO_2H$, —$CH_2CO_2H$, —$P(O)(OH)_2$, —$CH_2P(O)(OH)_2$, —$SO_3H$ or benzyl.

A preferred compound of the present invention is a compound of Formula (1B)

(1B)
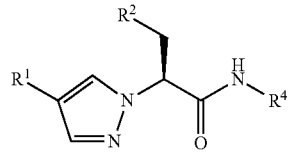

where $R^1$, $R^2$, and $R^4$ are as described above.

Preferred compounds of Formula (1B) include (S)-3-cyclopentyl-2-(4-(isopropylsulfonyl)-1H-pyrazol-1-yl)-N-(5-methylpyridin-2-yl)propanamide; (S)-3-cyclopentyl-2-(4-(isopropylsulfonyl-1H-pyrazol-1-yl)-N-(pyrazin-2-yl) propanamide; (S)-3-cyclopentyl-2-(4-(isopropylsulfonyl)-1H-pyrazol-1-yl)-N-(5-(trifluoromethyl)pyridin-2-yl) propanamide; (S)-3-cyclopentyl-2-(4-(isopropylsulfonyl)-1H-pyrazol-1-yl)-N-(pyrimidin-4-yl)-propanamide; (S)-3-cyclopentyl-2-(4-(isopropylsulfonyl)-1H-pyrazol-1-yl)-N-(pyrimidin-2-yl)-propanamide; (S)-3-cyclopentyl-2-(4-(isopropylsulfonyl)-1H-pyrazol-1-yl)-N-(5methylpyrazin-2yl)-propanamide; (S)-3-cyclopentyl-2-(4-(isopropylsulfonyl)-1H-pyrazol-1yl)-N-(1-methyl-1H-pyrazol-3yl)-propanamide; (S)-3-cyclopentyl-N-(5-methylpyridin-2-yl)-2-(4-(methylsulfonyl-1H-pyrazol-1-yl)-propanamide; (S)-3-cyclopentyl-N-(1-methyl-1H-pyrazol-3-yl)-2-(4-(methylsulfonyl)-1H-pyrazol-1-yl)-propanamide; (S)-3-cyclopentyl-2-(4-(methylsulfonyl)-1H-pyrazol-1-yl)-N-(5-(trifluoromethyl)pyridin-2-yl) propanamide; (S)-3-cyclopentyl-N-(1-ethyl-1H-pyrazol-3-yl)-2-(4-(methylsulfonyl)-1H-pyrazol-1-yl)-propanamide; (S)—N-(1-benzyl-1H-pyrazol-3-yl)-3-cyclopentyl-2-(4-(methylsulfonyl)-1H-pyrazol-1-yl)-propanamide; (S)-3-cyclopentyl-2-(4-(methylsulfonyl)-1H-pyrazol-1-yl)-N-(pyrimidin-4-yl)propanamide; (S)-3-cyclopentyl-N-(5-methylpyrazin-2-yl)-2-(4-(methylsulfonyl)-1H-pyrazol-1-yl)-propanamide; (S)-3-cyclopentyl-2-(4-(isopropylsulfonyl)-1H-pyrazol-1-yl)-N-(isoxazol-3-yl)-propanamide; (S)-3-cyclopentyl-2-(4-(isopropylsulfonyl)-1H-pyrazol-1-yl)-N-(pyridin-2-yl)propanamide; (S)-3-cyclopentyl-2-(4-(isopropylsulfonyl)-1H-pyrazol-1-yl)-N-(quinolin-2-yl)-propanamide; (S)-3-cyclopentyl-N-(1-ethyl-1H-pyrazol-3-yl)-2-(4-(isopropylsulfonyl)-1H-pyrazol-1-yl)-propanamide; (S)—N-(1-benzyl-1H-pyrazol-3-yl)-3-cyclopentyl-2-(4-(isopropylsulfonyl)-1H-pyrazol-1-yl)-propanamide; (S)-3-cyclopentyl-2-(4-(ethylsulfonyl)-1H-pyrazol-1-yl)-N-(1-methyl-1H-pyrazol-3-yl)-propanamide;

(S)-3-cyclopentyl-2-(4-(ethylsulfonyl)-1H-pyrazol-1-yl)-N-(5-methylpyridin-2-yl)-propanamide; (S)-3-cyclopentyl-2-(4-(ethylsulfonyl)-1H-pyrazol-1-yl)-N-(5-methylpyrazin-2-yl)-propanamide; (S)-benzyl 6-(3-cylclopentyl-2-(4-(methylsulfonyl)-1H-pyrazol-1-yl)propanamido)nicotinate; and (S)-6-(3-cyclopentyl-2-(4-(methylsulfonyl)-1H-pyrazol-1-yl)propanamido)nicotinic acid; or a pharmaceutically acceptable salt thereof.

Another preferred compound of the present invention is a compound of Formula (1C)

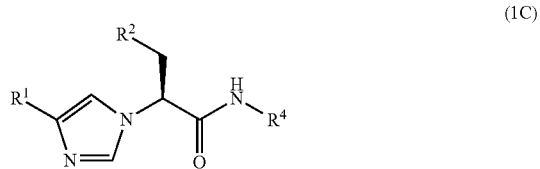

(1C)

where R¹, R², and R⁴ are as described above.

Preferred compounds of Formula (1) include(S)-3-cyclopentyl-2-(4-(isopropylsulfonyl)-1H-imidazol-1-yl)-N-(5-methylpyridin-2-yl)propanamide; (S)-3-cyclopentyl-2-(4-(isopropylsulfonyl)-1H-imidazol-1-yl)-N-(1-methyl-1H-pyrazol-3-yl)propanamide; (S)-3-cyclopentyl-2-(4-(isopropylsulfonyl)-1H-imidazol-1-yl)-N-(5-methylpyrazin-2-yl)propanamide; (S)-3-cyclopentyl-2-(4-(ethylsulfonyl)-1H-imidazol-1-yl)-N-(1-methyl-1H-pyrazol-3-yl)propanamide; (S)-3-cyclopentyl-2-(4-(ethylsulfonyl)-1H-imidazol-1-yl)-N-(5-methylpyridin-2-yl)propanamide; (S)-3-cyclopentyl-2-(4-(ethylsulfonyl)-1H-imidazol-1-yl)-N-(5-methylpyrazin-2-yl)propanamide; (S)-3-cyclopentyl-N-(5-methylpyrazin-2-yl)-2-(4-(methylsulfonyl)-1H-imidazol-1-yl)propanamide; (S)-3-cyclopentyl-N-(5-methylpyridin-2-yl)-2-(4-(methylsulfonyl)-1H-imidazol-1-yl)propanamide; (S)-3-cyclopentyl-N-(1-methyl-1H-pyrazol-3-yl)-2-(4-(methylsulfonyl)-1H-imidazol-1-yl)propanamide; (S)-benzyl 6-(3-cyclopentyl-2-(4-(methylsulfonyl)-1H-imidazol-1-yl)propanamido)nicotinate; (S)-6-(3-cyclopentyl-2-(4-(methylsulfonyl)-1H-imidazol-1-yl)propanamido)nicotinic acid; (S)-6-(3-cyclopentyl-2-(4-(ethylsulfonyl)-1H-imidazol-1-yl)propanamido)nicotinic acid; (S)-6-(3-cyclopentyl-2-(4-(isopropylsulfonyl)-1H-imidazol-1-yl)propanamido)nicotinic acid; (S)-6-(2-(4-(cyclobutylsulfonyl)-1H-imidazol-1-yl)-3-cyclopentylpropanamido)nicotinic acid; 6-[(S)-3-cyclopentyl-2-(4-dimethylsulfamoyl-imidazol-1-yl)-propionylamino]nicotinic acid; (S)-3-cyclopentyl-N-(1-methyl-1H-pyrazol-3-yl)-2-(4-(trifluoromethyl)-1H-imidazol-1-yl)propanamide; (S)-3-cyclopentyl-N-(5-methylpyridin-2-yl)-2-(4-(trifluoromethyl)-1H-imidazol-1-yl)propanamide; (S)-3-cyclopentyl-N-(5-methylpyrazin-2-yl)-2-(4-(trifluoromethyl)-1H-imidazol-1-yl)propanamide; (S)-methyl 6-(3-cyclopentyl-2-(4-(trifluoromethyl)-1H-imidazol-1-yl)propanamido)nicotinate; (S)-benzyl 6-(3-cyclopentyl-2-(4-(trifluoromethyl)-1H-imidazol-1-yl)propanamido)nicotinate; (S)-6-(3-cyclopentyl-2-(4-(trifluoromethyl)-1H-imidazol-1-yl)propanamido)nicotinic acid; (S)-3-cyclopentyl-N-(2-ethyl-2H-[1,2,3]triazol-4-yl)-2-(4-trifluoromethyl-1H-imidazol-1-yl)propanamide; (S)-3-cyclopentyl-N-(5-((S)-1,2-dihydroxyethyppyrazin-2-yl)-2-(4-(trifluoromethyl)-1H-imidazol-1-yl)propanamide; (S)-3-cyclopentyl-N-[5-(methylsulfonyl)pyridin-2-yl]-2-[4-(trifluoromethyl)-1H-imidazol-1-yl]propanamide; 6-[(S)-3-cyclopentyl-2-(4-trifluoromethyl-1H-imidazol-1-yl)-propionylamino]nicotinamide; (S)-benzyl 5-(3-cyclopentyl-2-(4-(trifluoromethyl)-1H-imidazol-1-yl)propanamido)pyrazine-2-carboxylate; (S)-5-(3-cyclopentyl-2-(4-(trifluoromethyl)-1H-imidazol-1-yl)propanamido)pyrazine-2-carboxylic acid; (S)-ethyl 2-(3-(3-cyclopentyl-2-(4-(trifluoromethyl)-1H-imidazol-1-yl)propanamido)-1H-pyrazol-1-yl)acetate; (S)-3-cyclopentyl-N-(1-(2-hydroxy-2-methylpropyl)-1H-pyrazol-3-yl)-2-(4-(trifluoromethyl)-1H-imidazol-1-yl)propanamide; (S)-2-(3-(3-cyclopentyl-2-(4-(trifluoromethyl)-1H-imidazol-1-yl)propanamido)-1H-pyrazol-1-yl)acetic acid; (S)-diethyl(6-(3-cyclopentyl-2-(4-(trifluoromethyl)-1H-imidazol-1-yl)propanamido)pyridin-3-yl)methylphosphonate; (S)-diethyl 6-(3-cyclopentyl-2-(4-(trifluoromethyl)-1H-imidazol-1-yl)propanamido)pyridin-3-ylphosphonate; (S)-(6-(3-cyclopentyl-2-(4-(trifluoromethyl)-1H-imidazol-1-yl)propanamido)pyridin-3-yl)methylphosphonic acid; (S)-6-(3-cyclopentyl-2-(4-(trifluoromethyl)-1H-imidazol-1-yl)propanamido)pyridine-3-sulfonic acid; (S)-6-(3-cyclopentyl-2-(4-(trifluoromethyl)-1H-imidazol-1-yl)propanamido)pyridin-3-ylphosphonic acid; 6-((S)-3-cyclopentyl-2-(4-(trifluoromethyl)-1H-imidazol-1-yl)propanamido)pyridin-3-yl(methyl)phosphinic acid; (S)-2-(6-(3-cyclopentyl-2-(4-(trifluoromethyl)-1H-imidazol-1-yl)propanamido)pyridin-3-yl)acetic acid; (S)-2-(6-(3-cyclopentyl-2-(4-(trifluoromethyl)-1H-imidazol-1-yl)propanamido)pyridin-3-yl)-2-methylpropanoic acid; (S)-2-(6-(3-cyclopentyl-2-(4-(trifluoromethyl)-1H-imidazol-1-yl)propanamido)pyridin-3-ylamino)-2-oxoacetic acid; and (S)-3-Cyclopentyl-N-[5-(2-hydroxy-2-methyl-propionylamino)-pyridin-2-yl]-2-(4-trifluoromethyl-imidazol-1-yl)-propionamide; (S)—N-(5-methylpyrazin-2-yl)-3-(tetrahydro-2H-pyran-4-yl)-2-(4-(trifluoromethyl)-1H-imidazol-1-yl)propanamide; (S)—N-(5-methylpyridin-2-yl)-3-(tetrahydro-2H-pyran-4-yl)-2-(4-(trifluoromethyl)-1H-imidazol-1-yl)propanamide; (S)—N-(1-methyl-1H-pyrazol-3-yl)-3-(tetrahydro-2H-pyran-4-yl)-2-(4-(trifluoromethyl)-1H-imidazol-1-yl)propanamide; (S)-3-(tetrahydro-2H-pyran-4-yl)-N-(thiazolo[5,4-b]pyridin-2-yl)-2-(4-(trifluoromethyl)-1H-imidazol-1-yl)propanamide; (S)—N-(5-methoxythiazolo[5,4-b]pyridin-2-yl)-3-(tetrahydro-2H-pyran-4-yl)-2-(4-(trifluoromethyl)-1H-imidazol-1-yl)propanamide; (2S)—N-(5-methylpyridin-2-yl)-3-(tetrahydrofuran-2-yl)-2-(4-(trifluoromethyl)-1H-imidazol-1-yl)propanamide; (S)—N-(5-methylpyridin-2-yl)-3-(1H-pyrazol-1-yl)-2-(4-(trifluoromethyl)-1H-imidazol-1-yl)propanamide; and (S)-6-(3-cyclohexyl-2-(4-(trifluoromethyl)-1H-imidazol-1-yl)propanamido)nicotinic acid; or a pharmaceutically acceptable salt thereof.

More preferred compounds of Formula (1C) include (S)-3-cyclopentyl-N-(1-methyl-1H-pyrazol-3-yl)-2-(4-(trifluoromethyl)-1H-imidazol-1-yl)-propanamide; (S)-3-cyclopentyl-N-(5-methylpyridin-2-yl)-2-(4-(trifluoromethyl)-1H-imidazol-1-yl)-propanamide; (S)-3-cyclopentyl-N-(5-methylpyrazin-2-yl)-2-(4-(trifluoromethyl)-1H-imidazol-1-yl)-propanamide; (S)—N-(5-methylpyrazin-2-yl)-3-(tetrahydro-2H-pyran-4-yl)-2-(4-(trifluoromethyl)-1H-imidazol-1-yl)propanamide; (S)—N-(5-methylpyridin-2-yl)-3-(tetrahydro-2H-pyran-4-yl)-2-(4-(trifluoromethyl)-1H-imidazol-1-yl)propanamide; (S)-6-(3-cyclopentyl-2-(4-(ethylsulfonyl)-1H-imidazol-1-yl)propanamido)nicotinic acid; (S)-6-(2-(4-(cyclobutylsulfonyl)-1H-imidazol-1-yl)-3-cyclopentylpropanamido)nicotinic acid; (S)-6-(3-cyclopentyl-2-(4-(trifluoromethyl)-1H-imidazol-1-yl)propanamido) nicotinic acid; (S)-2-(6-(3-cyclopentyl-2-(4-(trifluoromethyl)-1H-imidazol-1-yl)propanamido)pyridin-3-yl)acetic acid; and (S)-6-(3-cyclohexyl-2-(4-

(trifluoromethyl)-1H-imidazol-1-yl)propanamido)nicotinic acid; or a pharmaceutically acceptable salt thereof.

Another preferred compound of the present invention is a compound of Formula (1D)

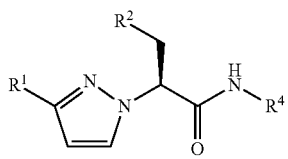

(1D)

where $R^1$, $R^2$, and $R^4$ are as described above.

Preferred compounds of Formula (1D) include (S)-3-cyclopentyl-N-(1-methyl-1H-pyrazol-3-yl)-2-(3-(trifluoromethyl)-1H-pyrazol-1-yl)propanamide; (S)-3-cyclopentyl-N-(5-methylpyridin-2-yl)-2-(3-(trifluoromethyl)-1H-pyrazol-1-yl)propanamide; and (S)-3-cyclopentyl-N-(5-methylpyrazin-2-yl)-2-(3-(trifluoromethyl)-1H-pyrazol-1-yl)propanamide; or a pharmaceutically acceptable salt thereof.

Another preferred compound of the present invention is a compound of Formula (1E)

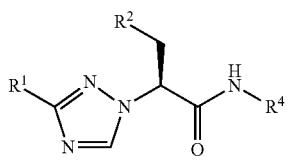

(1E)

where the $R^1$, $R^2$, and $R^4$ are as described above.

Preferred compounds of Formula (1E) include (S)-3-cyclopentyl-N-(5-methylpyridin-2-yl)-2-(3-(methylsulfonyl)-1H-1,2,4-triazol-1-yl)propanamide; (S)-3-cyclopentyl-N-(1-methyl-1H-pyrazol-3-yl)-2-(3-(methylsulfonyl)-1H-1,2,4-triazol-1-yl)propanamide; (S)-3-cyclopentyl-N-(5-methylpyrazin-2-yl)-2-(3-(methylsulfonyl)-1H-1,2,4-triazol-1-yl)propanamide; (S)-3-cyclopentyl-N-(pyrazin-2-yl)-2-(3-(trifluoromethyl)-1H-1,2,4-triazol-1-yl) propanamide; (S)-3-cyclopentyl-N-(5-methylpyridin-2-yl)-2-(3-(trifluoromethyl)-1H-1,2,4-triazol-1-yl)propanamide; (S)-benzyl 6-(3-cyclopentyl-2-(3-(trifluoromethyl)-1H-1,2,4-triazol-1-yl)propanamido)nicotinate; (S)-ethyl 2-(3-(3-cyclopentyl-2-(3-(trifluoromethyl)-1H-1,2,4-triazol-1-yl)propanamido)-1H-pyrazol-1-yl)acetate; (S)-6-(3-cyclopentyl-2-(3-(trifluoromethyl)-1H-1,2,4-triazol-1-yl)propanamido) nicotinic acid; and (S)-2-(3-(3-cyclopentyl-2-(3-(trifluoromethyl)-1H-1,2,4-triazol-1-yl)propanamido)-1H-pyrazol-1-yl)acetic acid; or a pharmaceutically acceptable salt thereof.

Another aspect of the present invention is a pharmaceutical composition that comprises (1) a compound of the present invention, or a pharmaceutically acceptable salt thereof; and (2) a pharmaceutically acceptable excipient, diluent, or carrier. Preferably, the composition comprises a therapeutically effective amount of a compound of the present invention, or a pharmaceutically acceptable salt thereof, and a pharmaceutically acceptable excipient, diluent, or carrier.

The composition may comprise at least one additional pharmaceutical agent, a pharmaceutically acceptable salt thereof. Preferred additional pharmaceutical agents include anti-diabetic, anti-obesity, anti-hypertension, anti-hyperglycemic, and lipid lowering agents, as described herein. More preferred, are anti-diabetic and anti-obesity agents, as described herein.

In yet another aspect of the present invention is a method for treating a disease, condition, or disorder mediated by the glucokinase enzyme, in particular, activation of said enzyme, in a mammal that includes the step of administering to a mammal, preferably a human, in need of such treatment a therapeutically effective amount of a compound of the present invention, or a pharmaceutical composition thereof.

Diseases, disorders, or conditions mediated by glucokinase activators include Type II diabetes, hyperglycemia, metabolic syndrome, impaired glucose tolerance, glucosuria, cataracts, diabetic neuropathy, diabetic nephropathy, diabetic retinopathy, obesity, dyslipidemia, hypertension, hyperinsulinemia, and insulin resistance syndrome. Preferred diseases, disorders, or conditions include Type II diabetes, hyperglycemia, impaired glucose tolerance, obesity, and insulin resistance syndrome. More preferred are Type II diabetes, hyperglycemia, and obesity. Most preferred is Type II diabetes.

In yet another aspect of the present invention is a method of reducing the level of blood glucose in a mammal, preferably a human, which includes the step of administering to a mammal in need of such treatment a therapeutically effective amount of a compound of the present invention, or a pharmaceutical composition thereof.

Compounds of the present invention may be administered in combination with other pharmaceutical agents (in particular, anti-obesity and anti-diabetic agents described herein). The combination therapy may be administered as (1) a single pharmaceutical composition which comprises a compound of the present invention, at least one additional pharmaceutical agent described herein and a pharmaceutically acceptable excipient, diluent, or carrier; or (2) two separate pharmaceutical compositions comprising (i) a first composition comprising a compound of the present invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

DEFINITIONS

For purposes of the present invention, as described and claimed herein, the following terms and phrases are defined as follows:

"Activate(s)" or "activator", or "activation", as used herein, unless otherwise indicated, refers to the ability of the compounds of the present invention to indirectly or directly bind to the GK enzyme in a mammal as a ligand thereby partially or wholly activating said enzyme.

"Additional pharmaceutical agent(s)" as used herein, unless otherwise indicated, refers to other pharmaceutical compounds or products that provide a therapeutically effective amount of said agents that are useful for the treatment of a disease, condition, or disorder, as described herein.

"Alkoxy", as used herein, unless otherwise indicated, refers to an oxygen moiety having a further alkyl substituent. The alkyl portion (i.e., alkyl moiety) of an alkoxy group has the same definition as below. "Alkyl", as used herein, unless otherwise indicated, includes saturated monovalent hydrocarbon alkane radicals of the general formula $C_nH_{2n+1}$. The alkane radical may be straight or branched and may be unsubstituted or substituted. For example, the term "$(C_1$-$C_6)$ alkyl"

refers to a monovalent, straight or branched aliphatic group containing 1 to 6 carbon atoms. Non-exclusive examples of ($C_1$-$C_6$) alkyl groups include, but are not limited to methyl, ethyl, propyl, isopropyl, sec-butyl, t-butyl, n-propyl, n-butyl, i-butyl, s-butyl, n-pentyl, 1-methylbutyl, 2-methylbutyl, 3-methylbutyl, neopentyl, 3,3-dimethylpropyl, 2-methylpentyl, hexyl, and the like. Alkyl represented along with another term (e.g., alkylamino (e.g., $CH_3NH$—), aminoalkyl (e.g., $NH_2CH_2$—), di-alkylamino (e.g., $(CH_3)_2N$—), arylalkyl (e.g., benzyl), and the like) where said alkyl moiety has the same meaning as above and may be attached to the chemical moiety by any one of the carbon atoms of the aliphatic chain.

"Aryl", as used herein, unless otherwise indicated, refers to a monocyclic, bicyclic, or fused ring system wherein each ring is aromatic. A typical aryl group (e.g. phenyl, naphthyl) is a 6- to 10-membered carbocyclic ring or ring system. The aryl group may be attached to the chemical moiety by any one of the carbon atoms within the ring system. Aryl rings are optionally substituted with one to three substituents and may be fused to a heteroaryl to form an aromatic heteroaryl ring system.

"Compounds of the present invention", as used herein, unless otherwise indicated, refers to compounds of Formula (1A), pharmaceutically acceptable salts of the compounds, as well as, all stereoisomers (e.g., enantiomers), tautomers and isotopically labeled compounds, and are therefore considered equivalents of the compounds of the present invention. Solvates and hydrates of the Formula (1A) compounds, or a pharmaceutically acceptable salt thereof, are considered compositions.

"Cycloalkyl", as used herein, unless otherwise indicated, includes fully saturated or partially saturated carbocyclic alkyl moieties, wherein alkyl is as defined above. Preferred cycloalkyls are 3- to 6-membered monocyclic rings including cyclopropyl, cyclobutyl, cyclopentyl, and cyclohexyl. The cycloalkyl group may be attached to the chemical moiety by any one of the carbon atoms within the carbocyclic ring. Cycloalkyl groups are optionally substituted with one to three substituents. The 5- to 6-membered cycloalkyls may be fused with a heteroaryl to form a heteroaryl ring system.

"Diabetes", as used herein, unless otherwise indicated, refers to metabolic defects in the production and utilization of carbohydrates, particularly glucose, which result in the failure of glucose homeostasis. Preferred forms of diabetes include Type I diabetes, or insulin-dependent diabetes mellitus (IDDM) which results from the absolute deficiency of insulin and Type II diabetes, or non-insulin dependent diabetes mellitus (NIDDM), which often occurs with normal, or even elevated levels of insulin and appears to be the result of the inability of mammalian cells and tissues to respond appropriately to insulin. Most preferred is NIDDM.

"Diabetes-related disorder", as used herein, unless otherwise indicated, refers to metabolic syndrome (Syndrome X, or elevated blood glucose, hypertension, obesity, dyslipidemia), hyperglycemia, hyperinsulinemia, impaired glucose tolerance, impaired fasting glucose, insulin resistance, obesity, atherosclerotic disease, cardiovascular disease, cerebrovascular disease, peripheral vessel disease, lupus, polycystic ovary syndrome, carcinogenesis, diabetic neuropathy, diabetic nephropathy, diabetic retinopathy, diabetic macular edema, and hyperplasia.

"Halo-substituted alkyl", unless otherwise indicated, refers to an alkyl group substituted with one or more halogen atoms (e.g., chloromethyl, dichloromethyl, fluoromethyl, difluoromethyl, trifluoromethyl, perfluoroethyl, and the like. When substituted, the alkane radicals are preferably substituted with 1 to 3 fluoro substituents.

"Heteroaryl", as used herein, unless otherwise indicated, refers to an aromatic monocyclic or fused ring containing one or more heteroatoms each independently selected from N, O, or S, preferably from one to three heteroatoms. Non-exclusive examples of monocyclic rings include pyrolyl, furanyl, thiophenyl, pyrazolyl, oxazolyl, thiazolyl, oxadiazolyl, pyridinyl, tetrazolyl, pyridazinyl, pyrimidinyl, and the like. Non-exclusive examples of fused rings include: quinolinyl, cinnolinyl, benzofuranyl, benzothiazolyl, indolyl, iso-indolyl, indazolyl, and the like. The heteroaryl group may be attached to the chemical moiety by any one of the carbon atoms or heteroatoms (e.g., N, O, and S) within the ring. Heteroaryls are optionally substituted with one to three substituents.

"Heterocycle", as used herein, unless otherwise indicated, refers to non-aromatic rings containing one or more heteroatoms each independently selected from N, O, or S, preferably from one to three heteroatoms, that are either partially saturated or fully saturated and may exist as a monocyclic or fused ring. Non-exclusive examples of monocyclic heterocycles include: tetrahydrofuranyl, pyrrolidinyl, tetrahydropyranyl, tetrahydrothiophenyl, piperidinyl, piperazinyl, azathianyl, and the like. Non-exclusive examples of fused heterocycles include: 6,7-dihydro-5H-[1]pyridinyl, thiazolo[5,4-b]pyridinyl, 2,3-dihydro-1H-pyrrolo[2,3-c]pyridinyl, and the like. The heterocyclic group may be attached to the chemical moiety by any one of the carbon atoms or heteroatoms (e.g. N, O, and S) within the ring system. Heterocycles are optionally substituted with one to three substituents.

"Mammal", or "mammalian" as used herein, unless otherwise indicated, refers to an individual animal that is a member of the taxonomic class Mammalia. Non-exclusive examples of mammals include humans, dogs, cats, horses, and cattle, preferably human.

"Mediate(s)" or "mediated", as used herein, unless otherwise indicated, refers to the activation (e.g., partial or full) of the glucokinase enzyme by enhancing glucose binding, alleviating the inhibition of glucokinase regulatory protein, a key regulator of glucokinase activity in the liver, and/or to increase the catalytic rate of the glucokinase enzyme (e.g., change Vmax).

"Obesity" and "obese", as used herein, unless otherwise indicated, refers generally to individuals who are at least about 20-30% over the average weight for his/her age, sex and height. Technically, obese is defined, for males and females, as individuals whose body mass index is greater than 27.8 $kg/m^2$, and 27.3 $kg/m^2$, respectively. Those of skill in the art readily recognize that the invention method is not limited to those who fall within the above criteria. Indeed, the method of the invention can also be advantageously practiced by individuals who fall outside of these traditional criteria, for example, by those who may be prone to obesity.

"Pharmaceutically acceptable" as used herein, unless otherwise indicated, indicates that the substance or composition must be compatible chemically and/or toxicologically, with the other ingredients comprising a formulation, composition, and/or the mammal being treated therewith.

"Reducing the level of blood glucose", or "lower blood glucose" as used herein, unless otherwise indicated, refers to an amount of the compound of the present invention sufficient to provide circulating concentrations of the compound high enough to accomplish the desired effect of lowering blood glucose levels in a mammal.

"Therapeutically effective amount", as used herein, unless otherwise indicated, refers to an amount of the compounds of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

"Treatment", "treating", and the like, as used herein, unless otherwise indicated, refers to reversing, alleviating, or inhibiting the progress of the disorder or condition to which such term applies, or one or more symptoms of such disorder or condition. As used herein, these terms also encompass, depending on the condition of the mammal, preferably a human, preventing the onset of a disorder or condition, or of symptoms associated with a disorder or condition, including reducing the severity of a disorder or condition or symptoms associated therewith prior to affliction with said disorder or condition. Thus, treatment can refer to administration of the compounds of the present invention to a mammal that is not at the time of administration afflicted with the disorder or condition. Treating also encompasses preventing the recurrence of a disorder or condition or of symptoms associated therewith.

DETAILED DESCRIPTION OF THE INVENTION

The present invention provides Formula (1A) compounds, or pharmaceutically acceptable salts thereof, compositions and pharmaceutical compositions that are useful in the treatment of diseases, disorders, or conditions mediated by glucokinase activation, in particular, compounds that activate glucokinase in a mammal, preferably a human.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, "Reagents for Organic Synthesis", 1; 19, Wiley, New York (1967, 1999 ed.), or Beilsteins Handbuch der organischen Chemie, 4, Aufl. ed. Springer-Verlag, Berlin, including supplements (also available via the Beilstein online database)).

For illustrative purposes, the reaction schemes depicted below demonstrate potential routes for synthesizing compounds of the present invention, and key intermediates. For a more detailed description of the individual reaction steps, see the Examples section below. Those skilled in the art will appreciate that other suitable starting materials, reagents, and synthetic routes may be used to synthesize the compounds of the present invention and a variety of derivatives thereof. Further, many of the compounds prepared by the methods described below can be further modified in light of this disclosure using conventional chemistry well known to those skilled in the art.

Compounds of the present invention described herein contain at least one asymmetric or chiral center; and therefore, exist in different stereoisomeric forms. The R and S configurations are based upon knowledge of known chiral inversion/retention chemistry by those skilled in the art. For example, the chirality of an intermediate undergoes an inversion when a neucleophile attacks from the opposite side of the leaving group, the product could be designated as R or S depending on the priorities of the groups attached to the stereocenter (Stereochemistry of Organic Compounds, by Ernest L. Eliel, Samuel H. Wilen, John Wiley and Sons, Inc.(1994)). Whereas, if a nucleophile attaches to the same side as the leaving group the chirality of intermediate is retained. In most of the examples, there is an inversion of the configuration where a compound with R configuration is converted to compound with a S configuration as the priorities of the all the four substituents at the stereocenter is retained. It is further noted that the intermediates can also be racemic (50:50 mixture of stereoisomer) thereby producing racemic products. A chiral separation method can be used to separate these enantiomers to provide the specific R or S isomers. It is further noted that the intermediates can also be racemic thereby producing racemic products. A more detailed description of techniques that can be used to resolve stereoisomers of compounds from their racemic mixture can be found in Jean Jacques Andre Collet, Samuel H. Wilen, Enantiomers, Racemates and Resolutions, John Wiley and Sons, Inc. (1981). In addition, the present invention embraces all geometric and positional isomers. For example, if a compound of the present invention incorporates a double bond or a fused ring, both the cis- and trans-forms, as well as mixtures, are embraced within the scope of the invention.

In the preparation of compounds of the present invention, protection of remote functionality (e.g., primary or secondary amine) of intermediates from undesired reactions with a protecting or blocking group. The term "protecting group" or "Pg" refers to a substituent that is commonly employed to block or protect a particular functionality while reacting other functional groups on the compound. For example, an amine protecting group "Pg$^1$" or a carboxyl protecting group "Pg$^2$" is a substituent attached to an amine or carboxyl group that blocks or protects the amine or carboxyl functionality, respectively, of the compound. Suitable amine protecting groups include: 1-tert-butyloxycarbonyl (Boc), acyl groups including: formyl, acetyl, chloroacetyl, trichloro-acetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl, and the like; and acyloxy groups including: methoxycarbonyl, 9-fluorenyl-methoxycarbonyl, 2,2,2-trifluoroethoxycarbonyl, 2-trimethylsilylethxoycarbonyl, vinyloxycarbonyl, allyloxycarbonyl, 1,1-dimethyl-propynyloxycarbonyl, benzyloxycarbonyl, p-nitrobenzyloxycarbony, 2,4-dichlorobenzyloxycarbonyl, and the like. Representative carboxyl protecting groups include: methyl ester, however, it is not restricted to other alkyl, benzylester, silyl ester, or substituted benzyl esters. Additional carboxyl protecting groups include: methyl-, ethyl-, and t-butyl-esters, trimethylsilyl, t-butyldimethylsilyl, diphenylmethyl, benzhydryl, cyanoethyl, 2-(trimethylsilyl)ethyl, nitroethyl, 2-(trimethylsilyl) ethoxymethyl, 2-(p-toluenesulfonyl)ethyl, and the like.

Suitable protecting groups and their respective uses are readily determined by one skilled in the art. For a general description of protecting groups and their use, see T. W. Greene, *Protective Groups in Organic Synthesis*, John Wiley & Sons, New York, 1991.

The term "leaving group" or "L", as used herein, refers to the group with the meaning conventionally associated with it in synthetic organic chemistry, i.e., an atom or group displaceable under reaction (e.g., alkylating) conditions. Examples of leaving groups include halo (e.g., Cl, F, Br, I), alkyl (e.g., methyl and ethyl), thiomethyl, tosylates, mesylates, and the like. Preferably, the leaving group is a triflate or iodo group.

Schemes 1-5 outline the general procedures useful for the preparation of compounds of the present invention. It is to be understood, however, that the invention, as fully described herein and as recited in the claims, is not intended to be limited by the details of the following schemes or modes of preparation. Other reagents and preparatory modes known by the skilled artisan can also be used. Further, the leaving group, L, the protecting groups, $Pg^1$ and $Pg^2$, X, Y, Z, $R^1$, $R^2$, and $R^3$ are as described herein. In Scheme 1, W represents an atom such as carbon (C), nitrogen (N), or oxygen (O), preferably C or O, and the letter "m" refers to an integer with a value of 0, 1, or 2. The letter "L" refers to a leaving group which undergoes nucleophilic substitution with a nucleophile, and refers to a halogen (e.g., chlorine, bromine, fluorine, or iodide), triflate, mesylate, or tosylate, preferably a triflate. Further, the amino group is protected as a tert-butoxycarbonyl protecting group ($Pg^1$) and the carboxyl group is protected as a methylester protecting group ($Pg^2$).

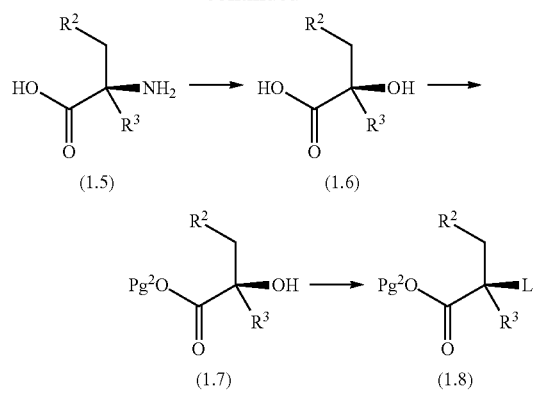

Scheme 1 describes the preparation of chiral α-amino acids (1.5) and finally to an activated ester (1.8) for introduction of an N-linked heterocycle. Although, Scheme 1 describes a method for the preparation of compound (1.5), availability of this amino acid is not restricted to this method only. Alpha-amino acids can also be prepared by other methods known to the skilled artisan or can be purchased from commercial vendors (e.g., Sigma-Aldrich (St. Louis, Mo.); Acros Organics (Geel, Belgium); Fulcrum Scientific Limited (West Yorkshire, UK); and Amatek Chemical (Kowloon, Hong Kong)). Amino ester (1.2) can be synthesized from an appropriately functionalized amino-protected (N-$Pg^1$) and carboxy-protected (O-$Pg^2$) derivative (1.1) with a leaving group (L, preferably an iodo group (Jackson, R. F. W., et. al., *Org. Syn.*, 81, 77, (2005)), by metal mediated coupling, for example, palladium. In a preferred example, 3,6-dihydro-2H-pyran-4-yl trifluoromethanesulfonate can be coupled with (R)-methyl 2-(tert-butoxycarbonylamino)-3-iodopropanoate in the presence of $PdCl_2(PPh_3)_2$ after treating the former with Zinc in an inert solvent such as dimethyl-formamide. The olefin functionality in (1.2) can then be reduced to the corresponding saturated compound (1.3) under hydrogenation conditions. A typical hydrogenation reaction can be performed in methanol with hydrogen in the presence of catalytic amount of Pd/C. Further removal of the amino-protecting group in (1.3) followed by removal of the carboxy protecting group of intermediate (1.4) affords the desired amino acid (1.5). For example, the tert-butoxycarbonyl protecting group and the methyl ester can be cleaved under acidic condition (HCl) in water. The activated ester (1.8) can be synthesized via treatment with an activating agent such as trifluoromethanesulfonic anhydride from the α-hydroxy-ester (1.7) (Degerbeck, F., et. al., *J. Chem. Soc., Perkin Trans.* 1, 11-14, (1993)). In a typical procedure this reaction can be performed in an inert solvent such as anhydrous $CH_2Cl_2$ in the presence of mild base such as 2,6-lutidine by dropwise addition of trifluoromethanesulfonic anhydride to the hydroxy-ester (1.7). The α-hydroxy-ester (1.7) can be prepared from the corresponding amino acid (1.5) via sequence of reactions, first by diazotization of the amino acid with sodium nitrite in water in presence of acid (McCubbin, J. A., et. al., *Org. Letters*, 8, 2993-2996, (2006)) followed by acid catalyzed ($H_2SO_4$) esterification of the resulting hydroxy-ester (1.6).

Scheme 2

Method A

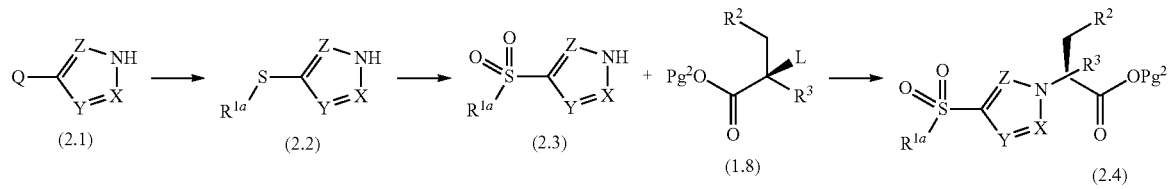

Method B

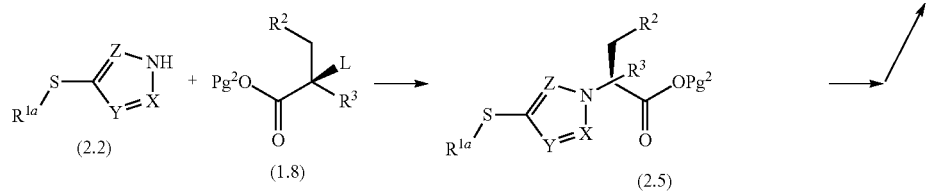

Method C

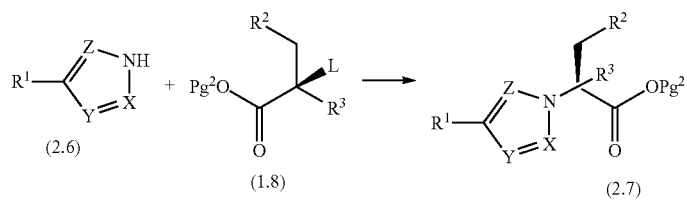

Scheme 2, describes the preparation of carboxy-protected hetero-substituted-esters (2.4) and (2.7).

In Method A, the intermediate (2.3) can be obtained from commercially available halo-substituted heterocycles (2.1) by treatment with t-butyllithium followed by reaction with a dialkyl disulfide (Katritzky, Alan R. et al. *J. Chem. Soc., Perkin Trans.* 1, (6), 1139-45; 1989). The resulting sulfide (2.2) can be oxidized to the corresponding sulfone with a suitable oxidant such as potassium peroxomonosulfate (Oxone®, DuPont Specialty Chemicals (Deepwater, N.J.)), or m-chloroperoxybenzoic acid (See, e.g., Bernotas, Ronald et al. *Bioorganic & Medicinal Chemistry Letters*, 14(22), 5499-5502; 2004; Kristof, T. J., et. al., *Tetrahedron*, 63, Issue 36, 8954-8961, (2007), Kulkarni, Surendra et al. Australian Journal of Chemistry, 40(8), 1415-25; 1987). Intermediate (2.3) can be converted to (2.4) by nucleophilic substitution reaction. The nucleophilic substitution reaction can be performed in a chiral compound with inversion of the stereochemistry at the chiral center. The nucleophile can be generated by treatment of an appropriate intermediate (2.3) with lithium hexamethyldisilazide and subsequent addition of the triflate-ester (1.8) thereby generating the carboxy-protected 2-hetero-substituted-ester (2.4). Other suitable bases with an appropriate $pK_b$ and other alkylating agents (e.g., alkyl sulfonates and the like) can also be utilized (Effenberger, Franz et al. *Liebigs Annalen der Chemie*, (2), 314-33; 1986; Terasaka, Tadashi et al. *Bioorganic & Medicinal Chemistry Letters*, 13(6), 1115-1118; 2003). Q is a halogen, preferably Br or I.

For example, 4-bromo-1H-imidazole (2.1) can be converted to 4-(alkylthio)-1H-imidazole (2.2) by treatment with t-butyllithium followed by reaction with dialkyldisulfide. The sulfide moiety in intermediate (2.2) can be oxidized to corresponding sulfone (2.3) by treatment with m-chloroperbenzoic acid in an inert solvent such as $CH_2Cl_2$. Methyl 3-substituted-2-(4-(alkylsulfonyl)-1H-imidazol-1-yl)propanoate (2.4) was then synthesized from (2.3) by treatment with lithium hexamethyldisilazide in an inert solvent such as THF followed by addition of triflate-ester (1.8).

Further, compound (2.4) can be prepared via reversal of the reaction sequence as shown in Method B. In this case, the alkylation of a sulfide derivative (2.2) with (1.8) can be performed first, and the resulting intermediate (2.5) can be oxidized to the desired sulfone (2.4). For example, 4-substituted-1H-pyrazole (2.2) can be synthesized from 4-bromo-1H-pyrazole (2.1) by metal-halogen exchange followed by treatment with a dialkyl-disulfide (e.g. diisopropyl disulfide) in THF at low temperature. 4-substituted-1H-pyrazole (2.2) can be treated with lithium bis(trimethylsilyl)amide followed by treatment with the activated ester (1.8) providing substituted-2-(4-(thioalkyl)-1H-pyrazol-1-yl)propanoate (2.5), which can be further oxidized to the sulfone with potassium peroxomonosulfate (Oxone®, DuPont Specialty Chemicals, Deepwater, N.J., USA).

Finally, compound (2.7) can be prepared directly from the commercially available heterocycles (such as 3-(trifluoromethyl)-1H-pyrazole, (Shanghai Sinofluoro Scientific Corporation, Shanghai, China)) as shown in Method C using alkylation chemistry as described herein.

Scheme 3

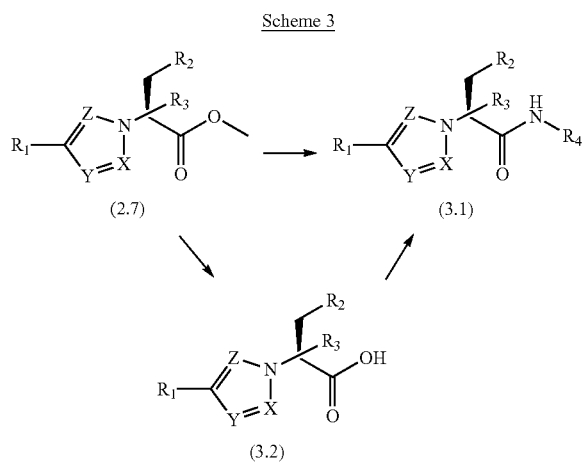

The final transformation to the amide (3.1) can be accomplished via an acid catalyzed transamidation reaction. For example, transformation of the α-heterocycle substituted ester (2.7, wherein the Pg² moiety depicted is methyl) to the amide (3.1) can be achieved by treatment with a Lewis acid in the presence of an appropriate amine ($R^4NH_2$), also referred to as an aprotic acid, such as $AlMe_3$ or $AlMe_2Cl$. See, e.g., Yadav, J. S., et. al., Tet. Letters, 48, Issue 24, 4169-4172, (1977). Other suitable Lewis acids include $Al_2O_3$, $TiO_2$, $ZnCl_2$, $SnCl_4$, $TiCl_4$, $FeCl_3$, $AlMe_3$, $AlMe_2Cl$, and the like.

Alternatively, this transformation can be achieved via ester hydrolysis of the ester (2.7) to the corresponding carboxylic acid (3.2) under acidic or basic conditions and coupling with an appropriate amine to produce the pyridone amide (i.e., a compound of the present invention). Hydrolysis of the ester can be performed under either basic or acidic conditions. For example, aqueous NaOH, KOH, or LiOH in the presence of an inert organic solvent such as THF or dioxane can be used for base catalyzed hydrolysis. For acid catalyzed hydrolysis, HCl in the presence of water with or without an organic solvent can be used. See, e.g., Puschl, A., et. al., J. Chem. Soc., Perkin Transactions 1, (21), 2757-2763, (2001). Other suitable methods can be used to catalyze the hydrolysis. It is noted that compounds of Formula (2.4) can undergo a similar acid catalyzed transamidation reaction or ester hydrolysis for the final sulfonyl substituted amide transformation. The term "coupling reagent" refers to a chemical reagent that is commonly employed as an agent to couple or join two or more specific compounds to make a single combined compound. Suitable coupling agents include [O-(7-azabenzotriazol-1-yl)-N,N,N',N'-tetramethyluronium hexafluorophosphate], 1,1'-thiocarbonyldimidazole, and the like. Moreover, activation of the acid (3.2) to an acid chloride followed by treatment of the suitable amine will also provide compound (3.1).

Scheme 4

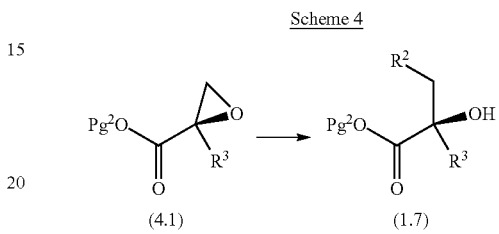

Scheme 4 describes an alternate preparation of the hydroxy-ester (1.7) (Alami, M., et. al., Tet. Asym., 8(17), 2949-2959, (1997). $Li_2CuCl_4$, prepared from $CuCl_2$ and LiCl in THF, can be added to a cold Grignard reagent solution in THF, for instance in a preferred example cyclopentylmagnesium bromide, to form the alkyl magnesium cuprate. Upon addition of (4.1), for instance methyl(2R)-glycidate, followed by an aqueous quench, (1.7) is formed.

Scheme 5

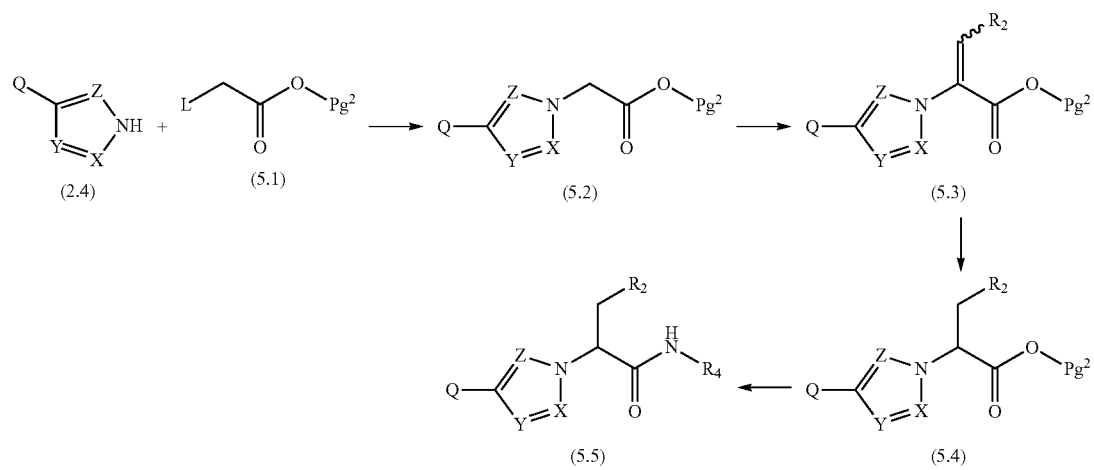

Scheme 5 describes another route to synthesize compounds like (5.5). Intermediate (5.2) can be synthesized by the nucleophilic displacement of a leaving group, such as bromide, on (5.1) by the anion of heterocycle (2.4) formed by mixing (2.4) with a base of sufficient strength, such as sodium hydride (Liu, Z.-C., et al. Tetrahedron, 2005, 61(33), 7967-7973.). An aldol condensation with an aldehyde can form alkene (5.3) via dehydration of a hydroxy intermediate (Sawyer, J. S. J. Med. Chem. 2005, 48, 893-896.). This reaction is promoted by a base such as potassium tert-butoxide. Reduction of the double bond can form (5.4). This can be accomplished with methods that include Pd/C, hydrogen gas or transfer hydrogenation, whereby a hydrogen source other than hydrogen gas is used, for example ammonium formate in the presence of Pd/C (Ranu, B. C., et al. *J. Indian Chem. Soc.* 1998, 75(10-12), 690-694.). Forming (5.5) can be accomplished as detailed in Scheme 3 either directly or via the carboxylic acid.

A compound of the present invention may be isolated and used per se or optionally administered in the form of its pharmaceutically acceptable salt, hydrate, and/or solvate. For example, it is well within the scope of the present invention to convert the compounds of the present invention into and use them in the form of their pharmaceutically acceptable salts derived from various organic and inorganic acids and bases, acids of amino acids, salts derived form organic and inorganic acids and cationic salts based on the alkali and alkaline earth metals in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydrofluoride, hydroiodide; other mineral acids and their corresponding salts such as sulfate, nitrate, phosphate; and alkyl and monoarysulfonates such as ethanesulfonate, toluenesulfonate, and benzene sulfonate; and other organic acids and their corresponding salts such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include sulfate, pyrosulfate, bisulfate, sulfite, bisulfite, nitrate, phosphate, monohydrogenphosphate, dihydrogenphosphate, metaphosphate, pyrophosphate, trifluoroacetate, propionate, caprylate, isobutyrate, oxalate, malonate, succinate, suberate, sebacate, fumarate, acetate, maleate, mandelate, benzoate, chlorobenzoate, methylbenzoate, dinitrobenzoate, phthalate, benzenesulfonate, toluenesulfonate, phenylacetate, citrate, lactate, malate, tartrate, methanesulfonate, and the like. Also contemplated are salts of amino acids such as arginate, gluconate, galacturonate, and the like. See, e.g., Berge S. M., et. al., Pharmaceutical Salts, *J. of Pharma. Sci.*, 66:1 (1977).

Compounds of the present invention that comprise basic nitrogen-containing groups may be quaternized with such agents as ($C_1$-$C_4$)alkyl halides, e.g., methyl, ethyl, isopropyl, and tert-butyl chlorides, bromides, and iodides; di-($C_1$-$C_4$) alkyl sulfates, e.g., dimethyl, diethyl, and diamyl sulfates; ($C_{10}$-$C_{18}$)alkyl halides, e.g., decyl, dodecyl, lauryl, myristyl, and stearyl chlorides, bromides, and iodides; and aryl($C_1$-$C_4$) alkyl halides, e.g., benzylchloride and phenethyl bromide. Such salts permit the preparation of both water-soluble and oil-soluble compounds of the present invention.

When the compounds of the present invention possess a free acid form, a pharmaceutically acceptable base addition salt can be prepared by reacting the free acid form of the compound with a pharmaceutically acceptable organic or inorganic base. Non-exclusive examples of base addition salts include, but are not limited to alkali metal hydroxides including potassium, sodium, and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are aluminum salts of the compounds of the present invention. Further base salts of the present invention include, but are not limited to: copper, ferric, ferrous, lithium, magnesium, manganic, manganous, potassium, sodium, and zinc salts. Organic base salts include but are not limited to, salts of primary, secondary, and tertiary amines, substituted amines including naturally occurring substituted amines, cyclic amines, e.g., ammonium, tetramethylammonium, tetraethylammonium, methylamine, dimethylamine, trimethylamine, triethylamine, and ethylamine; and basic ion exchange resins, e.g., arginine, betaine, caffeine, chloroprocaine, choline, N,N'-dibenzylethylenediamine, dicyclohexylamine, diethanolamine, 2-diethylaminoethanol, 2-dimethylaminoethanol, ethanolamine, ethylenediamine, N-ethylmorpholine, N-ethylpiperidine, glucamine, and glucosamine. See, e.g., Berge S. M., et. al., Pharmaceutical Salts, *J. of Pharma. Sci.*, 66:1, (1977). It should be recognized that the free acid forms will typically differ from their respective salt forms somewhat in physical properties such as solubility in polar solvents, but otherwise the salts are equivalent to their respective free acid forms for the purposes of the present invention.

All of the salt forms are within the scope of the compounds useful in the method of the present invention. Conventional concentration or crystallization techniques can be employed to isolate the salts.

The compounds and salts of the present invention may inherently form solvates, including hydrated forms, with pharmaceutically acceptable solvents. A solvate refers to a molecular complex of a compound represented by Formula (1A) including pharmaceutically acceptable salts thereof, with one or more solvent molecules. In general, the solvated forms, including hydrated forms, are equivalent to unsolvated forms and are intended to be encompassed within the scope of the present invention. Solvents that are commonly used in the pharmaceutical art, which are known to be innocuous to the recipient include water, ethanol, methanol, isopropanol, dimethylsulfoxide (DMSO), ethyl acetate, acetic acid, or ethanolamine, and the like. Although pharmaceutically acceptable solvents are preferred, other solvents may be used and then displaced with a pharmaceutically acceptable solvent to acquire certain polymorphs. A hydrate refers to the complex where the solvent molecule is water. Solvates, including hydrates, are considered compositions of the compound of the present invention.

It is also possible that the intermediates and compounds of the present invention may exist in different tautomeric forms. Tautomers refer to organic compounds that are interconvertible, i.e., when a chemical reaction results in a formal migration of a proton accompanied by a switch of a single bond and adjacent double bond (e.g., enol/keto, amide/imidic acid, and amine/imine forms) or as illustrated below

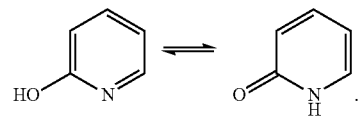

See, e.g., Katritzky, A. R., et. al., *The Tautomerism of Heterocycles*, Academic Press, New York, (1976). All such tautomeric forms are embraced within the scope of the invention.

The present invention also includes isotopically-labelled compounds, which are identical to those recited for the compound of Formula (1A), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine, iodine, and chlorine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{123}$I, $^{125}$I and $^{36}$Cl, respectively. Compounds of Formula (1A) which contain the aforementioned isotopes and/or other isotopes of other atoms are within the scope of this invention.

Certain isotopically-labelled compounds of the present invention, for example those into which radioactive isotopes such as $^{3}$H and $^{14}$C are incorporated, are useful in drug and/or substrate tissue distribution assays. Tritiated, i.e., $^{3}$H, and carbon-14, i.e., $^{14}$C, isotopes are particularly preferred for their ease of preparation and detectability.

Further, substitution with heavier isotopes such as deuterium, i.e., $^{2}$H, can afford certain therapeutic advantages resulting from greater metabolic stability, for example increased in vivo half-life or reduced dosage requirements and, hence, may be preferred in some circumstances. Positron emitting isotopes such as $^{15}$O, $^{13}$N, $^{11}$C, and $^{18}$F are useful for positron emission tomography (PET) studies to examine substrate occupancy. Isotopically labeled compounds of this invention thereof can generally be prepared by carrying out the procedures disclosed herein, by substituting a readily available isotopically labelled reagent for a non-isotopically labeled reagent.

Compounds of the present invention are useful for treating diseases, conditions and/or disorders mediated by the activation of glucokinase; therefore, another embodiment of the present invention is a pharmaceutical composition comprising a therapeutically effective amount of a compound of the present invention, or a pharmaceutically acceptable salt thereof, and a pharmaceutically acceptable excipient, diluent or carrier. The compounds of the present invention (including the compositions and processes used therein) may also be used in the manufacture of a medicament for the therapeutic applications described herein.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations can be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handled product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders mediated by the activation of glucokinase in a mammal that includes administering to a mammal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders that benefit from the activation of glucokinase which include: eating disorders (e.g., binge eating disorder, anorexia, bulimia, weight loss or control and obesity), prevention of obesity and insulin resistance by glucokinase expression in skeletal muscle of transgenic mice (Otaegui, P. J., et. al., *The FASEB Journal*, 17; 2097-2099, (2003)); and Type II diabetes, insulin resistance syndrome, insulin resistance, and hyperglycemia (Poitout, V., et. al., "An integrated view of β-cell dysfunction in type-II diabetes", *Annul. Rev. Medicine*, 47; 69-83, (1996)).

One aspect of the present invention is the treatment of Type II diabetes, progression of disease in Type II diabetes, metabolic syndrome (Syndrome X or a combination of elevated blood glucose, hypertension, obesity, decreased HDL cholesterol, and elevated triglycerides), hyperglycemia, impaired glucose tolerance (a pre-diabetic state of dysglycemia associated with insulin resistance), glucosuria (abnormal condition of osmotic diuresis due to excretion of glucose by the kidneys), cataracts, diabetic neuropathy, diabetic nephropathy, diabetic retinopathy, obesity; conditions exacerbated by obesity; hypertension; dyslipidemia; hyperinsulinemia (excess circulating blood insulin often associated with metabolic syndrome and NIDDM), and diabetic macular edema. The preferred disease, disorder, or condition to be treated is Type II diabetes, hyperglycemia, and reducing blood glucose. Most preferred is Type II diabetes.

Diabetes is generally defined as a syndrome characterized by disordered metabolism and inappropriately high blood glucose (hyperglycemia) resulting from either low levels of the hormone insulin or from abnormal resistance to insulin's effects coupled with inadequate levels of insulin secretion to compensate. Diabetes is generally characterized as three main forms: (1) Type I, (2) Type II, and (3) gestational diabetes. Type I diabetes is usually due to autoimmune destruction of the pancreatic beta cells. Type II diabetes is characterized by insulin resistance in target tissues. This causes a need for abnormally high amounts of insulin and diabetes develops when the beta cells cannot meet this demand. Gestational diabetes is similar to Type II diabetes in that it involves insulin resistance; the hormones of pregnancy can cause insulin resistance in women genetically predisposed to developing this condition, and typically resolves with delivery of the child. However, Types I and II are chronic conditions. Type 1 diabetes, in which insulin is not secreted by the pancreas, is directly treatable with insulin, although dietary and other lifestyle adjustments are part of disease management. Type II diabetes may be managed with a combination of diet and pharmaceutical products (e.g., medicaments), and frequently, insulin supplementation. Diabetes can cause many complications. Acute complications include hypoglycemia, hyperglycemia, ketoacidosis or nonketotic hyperosmolar coma. Serious long-term complications include, but are not limited to: cardiovascular disease, renal failure, retinal damage, decreased blood circulation, nerve damage, and hypertension.

In yet another aspect of the present invention is the treatment of diabetes related disorders, such as metabolic syndrome. Metabolic syndrome includes diseases, conditions or disorders such as dyslipidemia, hypertension, insulin resistance, coronary artery disease, obesity, and heart failure. For more detailed information on Metabolic Syndrome, see, e.g., Zimmet, P. Z., et al., "The Metabolic Syndrome: Perhaps an Etiologic Mystery but Far From a Myth—Where Does the International Diabetes Federation Stand?," *Diabetes & Endocrinology*, 7(2), (2005); and Alberti, K. G., et al., "The Metabolic Syndrome—A New Worldwide Definition," *Lancet*, 366, 1059-62 (2005). Preferably, administration of the compounds of the present invention provides a statistically significant ($p<0.05$) reduction in at least one cardiovascular disease risk factor, such as lowering of plasma leptin, C-reactive protein (CRP) and/or cholesterol, as compared to a vehicle control containing no drug. The administration of compounds of the present invention may also provide a statistically significant ($p<0.05$) reduction in glucose serum levels.

For a normal adult human having a body weight of about 100 kg, a dosage in the range of from about 0.001 mg to about 10 mg per kilogram body weight is typically sufficient, preferably from about 0.01 mg/kg to about 5.0 mg/kg, more preferably from about 0.01 mg/kg to about 1 mg/kg. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents (including appetite suppressants), anti-diabetic agents, anti-hyperglycemic agents, lipid lowering agents, and anti-hypertensive agents.

Suitable anti-obesity agents include cannabinoid-1 (CB-1) antagonists (such as rimonabant), 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, $\beta_3$ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists), $PYY_{3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as dirlotapide), opioid antagonist, orexin antagonist, and the like.

Preferred anti-obesity agents for use in the combination aspects of the present invention include CB-1 antagonists (e.g., rimonabant, taranabant, surinabant, otenabant, SLV319 (CAS No. 464213-10-3) and AVE1625 (CAS No. 358970-97-5)), gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo1-phenyl-4,5-dihydro-2,3,6, 10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), $PYY_{3-36}$ (as used herein "$PYY_{3-36}$" includes analogs, such as peglated $PYY_{3-36}$ e.g., those described in US Publication 2006/0178501), opioid antagonists (e.g., naltrexone), oleoylestrone (CAS No. 180003-17-2), obinepitide (TM30338), pramlintide (Symlin®), tesofensine (NS2330), leptin, liraglutide, bromocriptine, orlistat, exenatide (Byetta®), AOD-9604 (CAS No. 221231-10-3) and sibutramine. Preferably, compounds of the present invention and combination therapies are administered in conjunction with exercise and a sensible diet.

Suitable anti-diabetic agents include an acetyl-CoA carboxylase-2 (ACC-2) inhibitor, a phosphodiesterase (PDE)-10 inhibitor, a diacylglycerol acyltransferase (DGAT) 1 or 2 inhibitor, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone, rosiglitazone and troglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) agonist (e.g., exendin-3 and exendin-4), a protein tyrosine phosphatase-1 B (PTP-1B) inhibitor (e.g., trodusquemine, hyrtiosal extract, and compounds disclosed by Zhang, S., et al., *Drug Discovery Today*, 12 (9/10), 373-381 (2007)), SIRT-1 inhibitor (e.g., reservatrol), a dipeptidyl peptidase IV (DPP-IV) inhibitor (e.g., sitagliptin, vildagliptin, alogliptin and saxagliptin), an insulin secreatagogue, a fatty acid oxidation inhibitor, an A2 antagonist, a c-jun amino-terminal kinase (JNK) inhibitor, insulin, an insulin mimetic, a glycogen phosphorylase inhibitor, a VPAC2 receptor agonist and a glucokinase activator. Preferred antidiabetic agents are metformin and DPP-IV inhibitors (e.g., sitagliptin, vildagliptin, alogliptin and saxagliptin).

Suitable antihyperglycemic agents include, but are not limited to, alpha-glucosidase inhibitors (i.e., acarbose), biguanides, insulin, insulin secretagogues (i.e., sulfonureas (i.e., gliclazide, glimepiride, glyburide) and nonsulfonylureas (i.e., nateglinide and repaglinide)), thiazolidinediones (i.e. pioglitazone, rosiglitazone), and the like.

Suitable lipid lowering agents include, but are not limited to, HMGCoA reductase inhibitors, fibrates, microsomal triglyceride transfer protein inhibitors, cholesterol transfer protein inhibitors, acyl transfer protein inhibitors, low density lipid antioxidants, and the like.

Suitable antihypertensive agents include, but are not limited to, diuretics, adrenergic beta-antagonists, adrenergic alpha-antagonists, angiotensin-converting enzyme inhibitors, calcium channel blockers, ganglionic blockers, vasodilators, and the like.

According to the methods of the invention, when a compound of the present invention and at least one other pharmaceutical agent are administered together, such administration can be sequential in time or simultaneous with the simultaneous method being generally preferred. For sequential administration, a compound of the present invention and the additional pharmaceutical agent can be administered in any order. It is generally preferred that such administration be oral. It is especially preferred that such administration be oral and simultaneous. When a compound of the present invention and the additional pharmaceutical agent are administered sequentially, the administration of each can be by the same or by different methods, for example, tablet and syrup or capsule and parenteral injection or infusion. Administration and dosing will be determined by the prescribing practitioner.

The starting materials and reagents used in preparing these compounds are either available from commercial suppliers such as the Aldrich Chemical Company (Milwaukee, Wis.), Bachem (Torrance, Calif.), Sigma-Aldrich (St. Louis, Mo.), Acros Organics (Geel, Belgium), or Lancaster Synthesis Ltd. (Morecambe, United Kingdom) or may be prepared by methods well known to a person of ordinary skill in the art, following procedures described in such standard references as Fieser and Fieser's *Reagents for Organic Synthesis*, Vols. 1-17, John Wiley and Sons, New York, N.Y., (1991); *Rodd's Chemistry of Carbon compounds*, Vols. 1-5 and supps., Elsevier Science Publishers, (1989); *Organic Reactions*, Vols. 1-40, John Wiley and Sons, New York, N.Y., (1991); March J., *Advanced Organic Chemistry*, 4th ed., John Wiley and Sons, New York, N.Y.; and Larock, *Comprehensive Organic Transformations*, VCH Publishers, New York, (1989). Anhydrous tetrahydrofuran (THF), methylene chloride ($CH_2Cl_2$), and N,N-dimethylformamide may be purchased from Aldrich in Sure-Seal bottles and used as received. Solvents may be purified using standard methods known to those skilled in the art, unless otherwise indicated. Further, starting materials were obtained from commercial suppliers and used without further purification, unless otherwise indicated.

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed using glass-backed silica gel 60 F 254 precoated plates (Merck Art 5719) and eluted with appropriate solvent ratios (v/v). Reactions were assayed by TLC or LCMS and terminated as judged by the consumption of starting material. Visualization of the TLC plates was done with UV light (254 nM wavelength) or with an appropriate TLC visualizing solvent and activated with heat. Flash column chromatography (Still et al., *J. Org. Chem.* 43, 2923, (1978)) was performed using silica gel 60 (Merck Art 9385) or various MPLC systems, such as Biotage or ISCO purification system.

Conventional methods and/or techniques of separation and purification known to one of ordinary skill in the art can be used to isolate the compounds of the present invention, as well as the various intermediates related thereto. Such techniques will be well-known to one of ordinary skill in the art and may include, for example, all types of chromatography (high pressure liquid chromatography (HPLC), column chromatography using common adsorbents such as silica gel, and thin-layer chromatography (TLC)), recrystallization, and differential (i.e., liquid-liquid) extraction techniques. Biotage materials were purchased from Biotage AB (Charlottesville, Va.).

The compound structures in the Examples below were confirmed by one or more of the following methods: proton magnetic resonance spectroscopy, mass spectroscopy, and elemental microanalysis. Proton magnetic resonance ($^1H$ NMR) spectra were determined using a Bruker or Varian spectrometer operating at a field strength of 300 or 400 megahertz (MHz). Chemical shifts are reported in parts per million (PPM, δ) downfield from an internal tetramethylsilane standard. Alternatively, $^1H$ NMR spectra were referenced to signals from residual protons in deuterated solvents as follows: $CDCl_3$=7.25 ppm; DMSO-$d_6$=2.49 ppm; $C_6D_6$=7.16 ppm; $CD_3OD$=3.30 ppm. Mass spectra (MS) data were obtained using Agilent mass spectrometer or Waters Micromass spectrometer with atmospheric pressure chemical or electron spray ionization. Method: Acquity UPLC with chromatography performed on a Waters BEH C18 column (2.1×30 mm, 1.75 μm) at 60° C. The mobile phase was a binary gradient of acetonitrile (containing 0.05% trifluoroacetic acid) and water (5-95%) Elemental microanalyses were performed by Atlantic Microlab Inc. and gave results for the elements stated within ±0.4% of the theoretical values.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

All of the above recited U.S. patents and publications are incorporated herein by reference.

Preparation of Key Intermediates

The following intermediates provide a more detailed description of the process conditions. It is to be understood, however, that the invention, as fully described herein and as recited in the claims, is not intended to be limited by the details of the following schemes or modes of preparation. In the following intermediates, Boc refers to 1-tert-butyloxycarbonyl, and Tf refers to triflate.

Intermediate: (R)-methyl
3-cyclopentyl-2-hydroxypropanoic acid (I-1a)

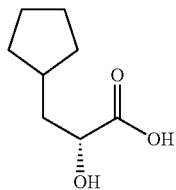

(I-1a)

To a stirred solution of (R)-2-amino-3-cyclopentylpropanoic acid (5.0 grams; Chem-Impex International, Inc., Wood Dale, Ill.) and 1 M $H_2SO_4$ (45.1 mL) at 0° C., was added a solution of $NaNO_2$ (3.12 g) in $H_2O$ (15.6 mL) drop wise over 10 minutes. The reaction mixture was stirred for 3 hours at 0° C., then for 2 hours at room temperature. The solution was then extracted (3 times) with diethyl ether. The combined organic extracts were dried over $MgSO_4$, filtered, and the filtrate concentrated to afford 2.36 g of (I-1a). $^1H$ NMR (400 MHz, $CDCl_3$) δ 4.26-4.28 (1 H), 1.99-2.07 (1H), 1.76-1.81 (4 H), 1.60-1.62 (4 H), 1.12-1.16 (2H); LCMS for $C_8H_{14}O_3$ m/z 157.1 (M–H)⁻.

Intermediate: (R)-methyl
3-cyclopentyl-2-hydroxypropanoate (I-1b)

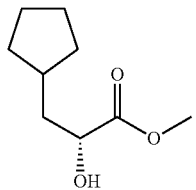

(I-1b)

To a stirred solution of 2.36 g of (I-1a) in anhydrous methanol (15 mL) at room temperature was added $SOCl_2$ (1.64 mL). The resulting mixture was heated at reflux for 2 hours. It was then cooled and concentrated under reduced pressure. The residue was partitioned between ethyl acetate and aqueous saturated $NaHCO_3$ solution. The biphasic mixture was separated and the aqueous portion was extracted with ethyl acetate. The combined extracts were dried over $MgSO_4$, filtered, and the filtrate concentrated under reduced pressure. The resulting residue was purified by flash column chromatography (silica gel, heptanes/ethyl acetate) to afford 1.5 g of (I-1b) as a clear oil. $^1H$ NMR (400 MHz, $CDCl_3$) δ 4.15-4.20 (1 H), 3.77 (3H), 2.62-2.63 (1 H), 1.97-2.05 (1 H), 1.49-1.86 (8 H), 1.06-1.17 (2 H); LCMS for $C_9H_{16}O_3$ m/z 171.6 (M)⁺. Intermediate (I-1b) can alternatively be prepared by the method described below.

A 0.2M solution of $Li_2CuCl_4$ was prepared as follows: Anhydrous $CuCl_2$ (26.9 g, 200 mol) and anhydrous LiCl (17.0 g, 400 mmol) were dissolved in THF (1000 mL). The mixture required gentle heating to completely dissolve the solids. After cooling the solution is ready for use.

A solution of $Li_2CuCl_4$ (0.2 M in THF, 125 mL, 25.0 mmol) was added slowly to a suspension of cyclopentylmagnesium bromide (2 M in diethyl ether, 135 mL, 270 mmol; Aldrich Chemical Company, Inc., Milwaukee, Wis.) and THF (500 mL) at –50° C. over 2-3 mins. The pale grey/brown suspension was then allowed to warm slowly to –10° C. over 30 mins, by which time the color had developed to a dark grey. The mixture was re-cooled to –78° C. and (R)-methyl oxirane-2-carboxylate (25.0 g, 245 mmol; Aldrich Chemical Company, Inc., Milwaukee, Wis.) was added neat via syringe over 90 seconds. The reaction was then stirred at –78° C. for 20 mins, before removing the ice-bath and allowing to warm to approximately –50° C. over 30 mins. Saturated $NH_4Cl$ (aq, 700 mL) was then added and the mixture stirred for 30 mins. The organic layer was collected and the aqueous layer extracted with diethyl ether (2×250 mL). The combined organics were washed with saturated $NH_4Cl$ (aq, 350 mL), dried over $MgSO_4$, and evaporated. Distillation of the crude residue (68-70° C. at 0.8 mbar) yielded 65-70% of (I-1b) as a pale yellow oil. A small amount of less volatile material remained in the still pot. $^1H$ NMR (400 MHz; $CDCl_3$): δ 4.17 (1 H), 3.76 (3 H), 2.67 (1 H), 2.01 (1 H), 1.48-1.88 (8 H), 1.11 (2 H).

Intermediate: (R)-methyl 3-cyclopentyl-2-(trifluoromethylsulfonyloxy)propanoate (I-1c)

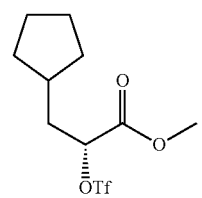

(I-1c)

Intermediate (I-1b) (6.37 g, 37.0 mmol) was dissolved in dry dichloromethane (260 mL) and stirred under nitrogen in an ice bath. 2,6-Lutidine (9.0 mL, 77 mmol) was added. Trifluoromethanesulfonic acid anhydride (11 mL, 65 mmol) in dry dichloromethane (75 mL) was added dropwise. The reaction was stirred in the ice bath for 60 minutes, concentrated under reduced pressure, and taken up in 1N HCl and methyl t-butyl ether. The aqueous layer was separated, and the organic layer was washed with additional 1N HCl to insure the removal of all the lutidine. The combined organic layer was then washed with brine, dried over sodium sulfate, filtered, concentrated under reduced pressure, and dried under high vacuum to afford (I-1c) (11.3 g, 37 mmol, 100%), which was used immediately without further purification; $^1H$ NMR (400 MHz, $CDCl_3$) δ 5.10-5.14 (1 H), 3.82 (3 H), 2.02-2.12 (1 H), 1.79-1.98 (4 H), 1.51-1.66 (4 H), 1.08-1.18 (2 H).

Intermediate: 4-(isopropylthio)-1H-pyrazole (I-2a)

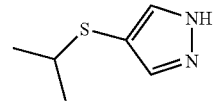

(I-2a)

To a stirred solution of 4-bromo-1H-pyrazole (2.49 g, 16.9 mmol; Aldrich Chemical Company, Inc., Milwaukee, Wis.) in THF under nitrogen at 0° C. was added dropwise n-butyllithium (34.9 mL, 1.6 M in hexanes). The reaction mixture was slowly warmed to room temperature and stirred for 1 hour. It was then cooled to 0° C., diisopropyl disulfide (2.70 mL, 16.9 mmol) was added dropwise and stirring continued at the same temperature for 2 hours. The reaction mixture was poured into a biphasic mixture of 100 mL ethyl acetate and 50 mL ice water. The pH of the mixture was adjusted to about 6 and the organic portion was separated, washed with water, brine and dried over MgSO$_4$. It was then filtered and the filtrate was concentrated under reduced pressure to afford 1.88 g of (I-2a).

Intermediate: (S)-methyl 3-cyclopentyl-2-(4-(isopropylthio)-1H-pyrazol-1-yl)propanoate (I-3a)

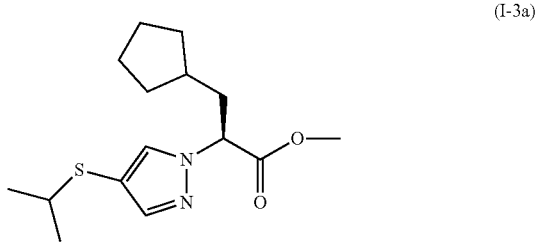 [SMILES: COC(=O)[C@H](CC1CCCC1)n1cc(SC(C)C)cn1]

(I-3a)

To a stirred solution of 124 mg of (I-2a) in 9 mL of anhydrous THF under nitrogen, a solution of lithium bis(trimethylsilyl)amide (0.784 mL, 1 M in hexanes) was added. After 45 minutes, a solution of Intermediate (I-1c) (265 mg in 6 mL of anhydrous THF) was added dropwise and stirring continued for 2 hours at room temperature. It was then quenched with aqueous saturated NH$_4$Cl and extracted with ethyl acetate. The combined organic extracts were dried over MgSO$_4$, filtered, and concentrated. The resulting residue was purified by flash chromatography (silica gel, 0-100% ethyl acetate in heptane) to afford (I-3a), m/z 297.1 (M+H)$^+$.

Intermediate: (S)-methyl 3-cyclopentyl-2-(4-(isopropylsulfonyl)-1H-pyrazol-1-yl)propanoate (I-4a1)

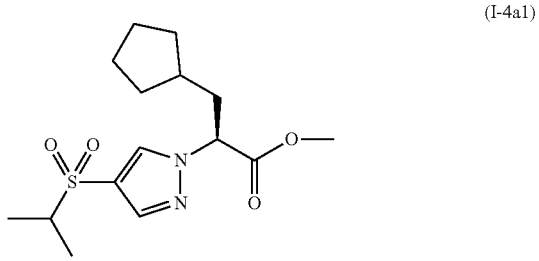 [SMILES: COC(=O)[C@H](CC1CCCC1)n1cc(S(=O)(=O)C(C)C)cn1]

(I-4a1)

To a stirred solution of 0.157 g (I-3a) in 5 mL dichloromethane at 0° C. was added trifluoroacetic acid (0.041 mL) followed by m-chloroperbenzoic acid (0.229 g). After 30 minutes, the ice bath was removed and the reaction stirred at room temperature for another 30 minutes before partitioning between ethyl acetate and aqueous saturated NaHCO$_3$. The aqueous portion was extracted with ethyl acetate and the combined organics were dried over MgSO$_4$. It was then filtered and the filtrate concentrated under reduced pressure. The resulting residue was purified by flash column chromatography (silica gel, 0-100% ethyl acetate in heptane) to afford 0.167 g of (I-4a1) as a white solid, m/z 329.2 (M+H)$^+$.

Intermediates (S)-methyl 3-cyclopentyl-2-(4-(methylsulfonyl)-1H-pyrazol-1-yl)propanoate (I-4a2) (m/z 301.2 (M+H)$^+$) and (S)-methyl 3-cyclopentyl-2-(4-(ethylsulfonyl)-1H-pyrazol-1-yl)propanoate (I-4a3) (m/z 315.4 (M+H)$^+$) were prepared in an analogous manner to that described for the synthesis of Intermediate (I-4a1) from 4-bromo-1H-pyrazole using appropriate starting materials (e.g., dimethyl disulfide or diethyl disulfide, respectively).

Intermediate: 3-(methylsulfonyl)-1H-1,2,4-triazole (I-5a)

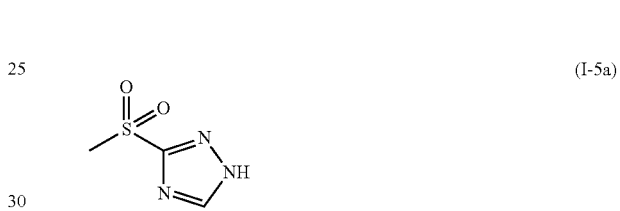

(I-5a)

To a stirred solution of 3-methylthio-4H-1,2,4-triazole (1.00 g; Oakwood Products, Inc., West Columbia, S.C.) in THF (20 mL) and water (20 mL) was added potassium peroxomonosulfate (Oxone®, DuPont Specialty Chemicals, Deepwater, N.J., USA) (10.7 g). After stirring at room temperature for a day, the reaction mixture was filtered and the filtercake was washed with THF. The filtrate was partitioned between water and ethyl acetate, the bilayer was separated and the aqueous portion was extracted twice with ethyl acetate. The combined organic extracts were dried over MgSO$_4$, filtered, and the filtrate concentrated under reduced pressure. The resulting residue was purified by flash chromatography (SiO$_2$, ethyl acetate/methanol, 0-10%) to afford 0.496 g of (I-5a) as a white solid. m/z 148.1 (M+H)$^+$.

Intermediate: (S)-methyl 3-cyclopentyl-2-(3-(methylsulfonyl)-1H-1,2,4-triazol-1-yl)propanoate (I-5b)

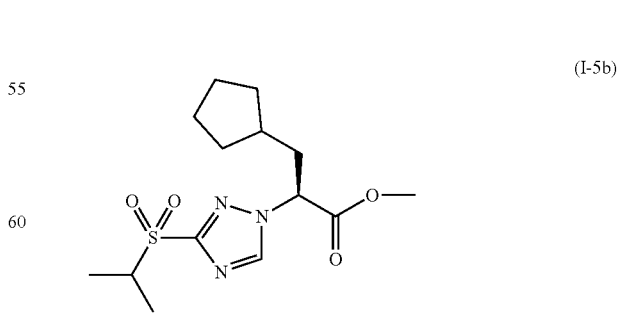

(I-5b)

To a stirred solution of 42.7 mg of (I-5a) in anhydrous THF (4 mL) under nitrogen was added lithium bis(trimethylsilyl)

amide (0.261 mL, 1 M in THF). After stirring for 30 minutes, a solution of Intermediate (I-1c) (88.3 mg) in anhydrous THF (10 mL) was added dropwise. After 1 hour, the reaction was quenched with water, brine was added, and extracted with ethyl acetate twice. The combined organics were dried over MgSO₄ and purified by flash chromatography (40+M, 75:25, 60:40, 50:50, 0:100 heptane:ethyl acetate) to give 0.0447 g of (I-5b) as a clear oil; m/z 302.2 (M+H)⁺

Intermediate: 4-(isopropylthio)-1H-imidazole (I-6a)

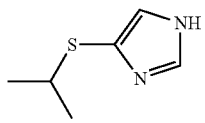

(I-6a)

To a stirred solution of 4-bromo-1H-imidazole (5.0 g; Aldrich Chemical Company, Inc., Milwaukee, Wis.) in 100 mL anhydrous THF at −78° C. in an oven dried 500 mL 3 necked-round bottom flask was added t-butyl-lithium (48.0 mL, 1.7 M in pentane) dropwise over 45 minutes with a dropping funnel. After complete addition, the mixture was warmed to about 10° C. to 15° C. for 2 hours and then it was cooled to −78° C., and a cold (−78° C.) solution of diisopropyl disulfide (6.78 mL) in 30 mL THF was added via cannula. The reaction was stirred for 16 hours allowing the bath to warm. The pale yellow solution was quenched with saturated NH₄Cl followed by neutralization with 10% HCl. The layers were separated and the aqueous extracted with THF three times. The combined organics were dried over MgSO₄ and purified by flash chromatography (40+M, 100:0, 95:5, 90:10 ethyl acetate/methanol) to afford 3.3767 g of (I-6a); m/z 143.0 (M+H)⁺.

Intermediate: 4-(isopropylsulfonyl)-1H-imidazole (I-6b)

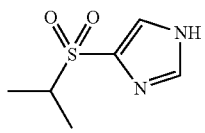

(I-6b)

To a stirred solution of 1.00 g (I-6a) in dichloromethane (14 mL) at 0° C. was added trifluoroacetic acid (0.54 mL) followed by m-chloroperbenzoic acid (6.07 g) was added in portions. An additional 10 mL dichloromethane was added to the mixture and stirring continued. After 20 minutes, the ice bath was removed and the reaction stirred at room temperature for another 30 minutes before adding 1 equivalent of 1N NaOH (7.03 mL). The mixture was concentrated and the residue purified by flash column chromatography (SiO₂, ethyl acetate/heptane 0 to 10%) to afford 1.19 g of (I-6b); m/z 175.1(M+H)⁺.

Intermediate: (S)-methyl 3-cyclopentyl-2-(4-(isopropylsulfonyl)-1H-imidazol-1-yl)propanoate (I-7a1)

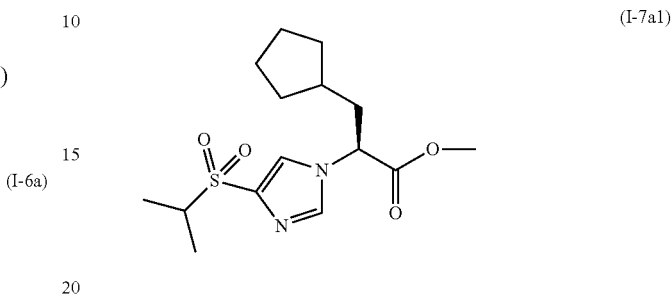

(I-7a1)

To a stirred solution of 50 mg of (I-6a) in anhydrous THF (4 mL) under nitrogen was added lithium bis(trimethylsilyl)amide (0.260 mL, 1 M in THF). After stirring for 30 minutes, a solution of Intermediate (I-1c) (88 mg in 3 mL anhydrous THF) was added dropwise. After 75 minutes, the reaction was quenched with water, brine was added, and extracted with ethyl acetate twice. The combined organics were dried over MgSO₄ and purified by flash chromatography (SiO₂, ethyl acetate/heptane, 25 to 100%) to afford 53 mg of (I-7a1); m/z 329.1 (M+H)⁺.

Intermediates (S)-methyl 3-cyclopentyl-2-(4-(ethylsulfonyl)-1H-imidazol-1-yl)propanoate (I-7a2) m/z 315.4 (M+H)⁺ and (S)-methyl 3-cyclopentyl-2-(4-(methylsulfonyl)-1H-imidazol-1-yl)propanoate (I-7a3) m/z 301.4 (M+H)⁺ were prepared in an analogous manner to that described for the synthesis of Intermediate I-7a1, above, from 4-bromo-1H-imidazole using appropriate starting materials (e.g., diethyl disulfide or dimethyl disulfide, respectively).

Intermediate: (S)-methyl 3-cyclopentyl-2-(4-(trifluoromethyl)-1H-imidazol-1-yl)propanoate (I-8a)

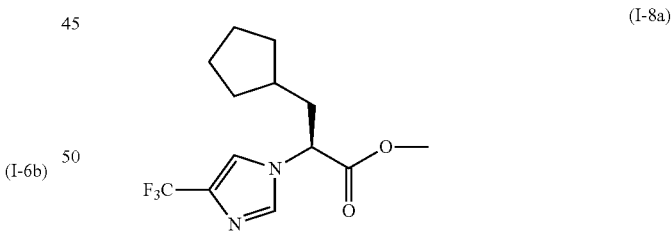

(I-8a)

4-Trifluoromethyl-1H-imidazole (5.0 g, 37.0 mmol; Apollo Scientific Ltd., Bredbury, Cheshire, UK) was stirred in dry THF (180 mL) under nitrogen at room temperature. Lithium hexamethyldisilazide (1 M in THF, 33.4 mL, 33.4 mmol) was added dropwise via addition funnel. The mixture was stirred at room temperature for 50 minutes and then chilled in an ice bath. A solution of (I-1c) (11.3 g, 37 mmol) in dry THF (45 mL), which had been chilled in an ice bath, was added in one portion. The reaction was allowed to warm to room temperature, stirred for 2 hours, quenched with saturated aqueous ammonium chloride solution (20 mL) and allowed to stir overnight. The aqueous layer was separated, and the organic layer was concentrated and then diluted with water and ethyl acetate. The organic layer was washed in series with dilute aqueous phosphoric acid, aqueous 10% potassium carbonate, and brine. The organic layer was then dried over sodium sulfate, filtered, and concentrated under reduced pressure to a brown oil. The crude material, containing the undesired regioisomer as a small impurity, was purified by chromatography on a 330 g pre-packed silica gel column, eluting with 10% ethyl acetate/heptane, linear gradient to 70% ethyl acetate/heptane. The product fractions were located by spotting on a silica TLC plate and visualizing with KMnO$_4$ stain. TLC (1:1 ethyl acetate/heptane, developed in potassium permanganate) located the pure and mixed fractions. The clean product fractions were combined, evaporated, and dried under high vacuum to afford (I-8a) as a clear oil (6.61 g, 22.4 mmol, 67%). $^1$H NMR (400 MHz, CDCl$_3$) δ 7.57 (1 H), 7.38 (1 H), 4.71-4.74 (1 H), 3.76 (3 H), 2.01-2.14 (2 H), 1.45-1.79 (7 H), 1.03-1.18 (2 H); m/z 291.4 (M+H)$^+$.

Intermediate: (S)-3-cyclopentyl-2-(4-(trifluoromethyl)-1H-imidazol-1-yl)propanoic acid (I-8b)

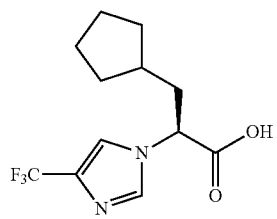

(I-8b)

6N HCl (140 mL) was added to (I-8a) (6.61 g, 22.4 mmol) and the mixture was warmed to 95° C. for 16 hours and then allowed to cool. Solid potassium carbonate (58 g) was added in portions to bring the pH to about 4. A precipitate crashed out. Ethyl acetate was added, and the mixture was stirred until everything dissolved. The aqueous layer was extracted once with ethyl acetate. The combined organics were washed with brine, dried over sodium sulfate, filtered, concentrated under reduced pressure, and dried under high vacuum to afford (I-8b) as a clear glass (6.15 g, 21.9 mmol, 98%). $^1$H NMR (400 MHz, CDCl$_3$) δ 7.73 (1 H), 7.34 (1 H), 6.85-7.15 (1 H), 4.66-4.70 (1 H), 1.98-2.17 (2 H), 1.41-1.75 (7 H), 1.01-1.19 (2 H); m/z 277.4 (M+H)$^+$.

Intermediate: (S)-3-cyclopentyl-2-(4-(trifluoromethyl)-1H-imidazol-1-yl)propanoyl chloride (I-8c)

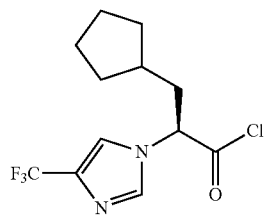

(I-8c)

To a suspension of intermediate (I-8b) (0.25 g, 0.9 mmol) in dichloromethane (5 mL) was added oxalyl chloride (0.35 g, 2.7 mmol) and N,N-dimethylformamide (1 drop) at room temperature. The mixture was stirred for 2 hours at room temperature. The reaction mixture was concentrated in vacuo, and the residue was chased with dichloromethane two times and concentrated in vacuo to afford (I-8c) (0.27 g, 100%) as an oil, which was used in the next step directly.

Intermediate: (S)-methyl 3-cyclopentyl-2-(3-(trifluoromethyl)-1H-pyrazol-1-yl)propanoate (I-9a1)

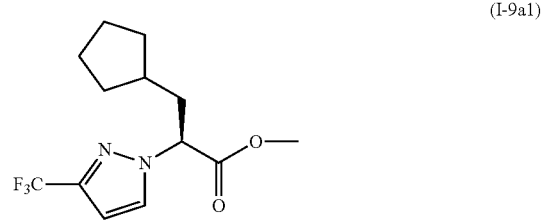 [SMILES: COC(=O)[C@H](CC1CCCC1)n1ccc(C(F)(F)F)n1]

(I-9a1)

To a stirred solution of 3-(trifluoromethyl)-1H-pyrazole (500 mg, 3.67 mmol; Aldrich Chemical Company, Inc., Milwaukee, Wis.) in 10 mL of anhydrous THF under nitrogen was added a solution of lithium hexamethyldisilazide (3.30 mL, 1 M in hexanes, 3.3 mmol). After stirring for 40 minutes at room temperature, a solution of Intermediate (I-1c) (1.12 g (3.67 mmol) in 2 mL of anhydrous THF) was added dropwise and stirring was continued for 2 hours at room temperature. It was then quenched with aqueous saturated NH$_4$Cl and extracted with ethyl acetate. The combined organic extracts were dried over MgSO$_4$, filtered, and concentrated. The resulting residue was purified by flash chromatography (SiO$_2$, dichloromethane/methanol, 0 to 10%)) to afford (I-9a1); m/z 291.0 (M+H)$^+$.

Intermediate (S)-methyl-3-cyclopentyl-2-(4-dimethylcarbamoyl)-1H-pyrazol-1-yl)-propanoate, (I-9a2), m/z 294.2 (M+H)$^+$ was prepared in an analogous manner to that described for the synthesis of Intermediate (I-9a1) from 1H-pyrazole-4-carboxylic acid (Aldrich Chemical Company, Inc., Milwaukee, Wis.) dimethylamide and Intermediate (I-1c).

Intermediate: 3,6-dihydro-2H-pyran-4-yl trifluoromethanesulfonate (I-10a)

(I-10a)

Under argon, diisopropylamine (66.8 g (92.5 mL), 0.66 mol) was dissolved in THF (1 L) and cooled to −5° C. in an ice/methanol bath. Over 30 minutes, n-butyl-lithium (2.34 M, 290 mL, 0.66 mol) was added while maintaining the temperature below 1° C. The mixture was stirred at about 0° C. to about −5° C. for 15 minutes and cooled to −72° C. with an acetone and dry ice bath. Dihydro-2H-pyran-4(3H)-one (Aldrich Chemical Company, Inc., Milwaukee, Wis.) was added slowly over 15 minutes while maintaining the temperature at −78° C. for 1 hour. N-phenyl-bis-(trifluoromethyl sulfonimide; Aldrich Chemical Company, Inc., Milwaukee, Wis.) was suspended in THF (500 mL) and added slowly to the mixture while maintaining a temperature below −60° C. The mixture was left stirring in the cooling bath, warming to room temperature overnight. The mixture was concentrated under reduced pressure. The residues were slurried in hexane at 50° C. (1 L and 250 mL), the liquors were concentrated under reduced pressure to afford (I-10a). $^1$H NMR (CDCl$_3$, 300 MHz) δ 5.74 (1H), 4.19 (2H), 3.80 (2H), 2.39 (2H).

Intermediate: (R)-methyl 2-(tert-butoxycarbonyl)-3-(3,6-dihydro-2H-pyran-4-yl)propanoate (I-10b)

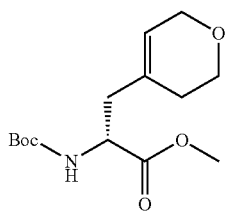

(I-10b)

In rigorously anaerobic conditions, zinc dust (72.7 g, 1.11 mol) was suspended in anhydrous N,N-dimethylformamide (100 mL), and to the stirred solution, trimethylsilyl chloride (23 mL 0.18 mol) was added (exotherm to 55° C.). The mixture was stirred for 20 minutes, during which time the supernatant became brown in color. The mixture was allowed to settle, and the supernatant decanted off using vacuum. The activated zinc powder was washed with N,N-dimethylformamide (4×50 mL), until the supernatant solvent became colorless.

(R)-methyl 2-(tert-butoxycarbonylamino)-3-iodopropanoate (Oakwood Products, West Columbia, S.C.) (85 g, 0.26 mol) was dissolved in N,N-dimethylformamide under argon, added in one portion to the activated zinc powder and stirred briskly. After approximately 5 minutes, the mixture self heated rapidly (21-30° C. over about 15 seconds). The stirring was stopped and the cooling bath immediately applied, allowing the exothermic reaction to be ceased at 50° C. As the temperature subsided, the cooling bath was removed and the mixture stirred at ambient temperature for 20 minutes and allowed to settle. The supernatant was syringed into a pre-prepared solution of (I-10a) (60 g, 0.26 mol) and PdCl$_2$(PPh$_3$)$_2$ (5.44 g, 7.75 mmol). The metallic solids were washed with N,N-dimethylformamide (30 mL) and the washings added to the triflate/catalyst mixture, which was stirred at 50° C. overnight. The solution was concentrated under reduced pressure and the crude product slurried in water (500 mL) and 20% ethyl acetate in hexane (500 mL). The mixture was filtered and partitioned, and the aqueous layer re-extracted with 20% ethyl acetate in hexane (500 mL). The combined organic phases were washed with brine (500 mL), dried over MgSO$_4$, and concentrated under reduced pressure. The semi-crude product was obtained as a free running red-brown oil (81 g), which was purified twice by dry-flash chromatography (SiO$_2$, ethyl acetate and Hexanes, 2 to 20%) followed by carbon treatment in 10% ethyl acetate/hexane to afford (I-10b): $^1$H NMR (CDCl$_3$, 300 MHz): δ 5.50 (1H), 4.95 (1H), 4.40 (1H), 4.10 (2H), 3.77 (2H), 3.73 (3H), 2.50 (1H), 2.31 (1H), 2.07 (2H), 1.43 (9H).

Intermediate: (R)-methyl 2-(tert-butoxycarbonyl)amino-3-(tetrahydro-2H-pyran-4-yl)propanoate (I-10c)

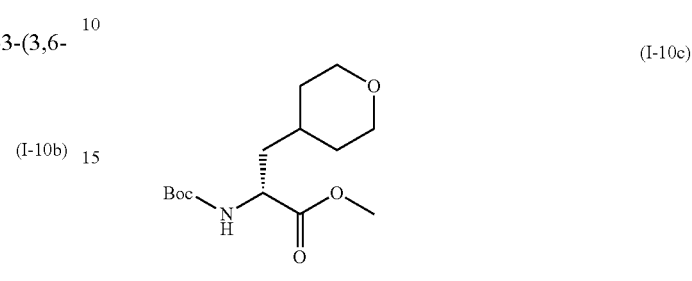

In a stainless steel autoclave, 22.83 g (80.0 mmol) of (I-10b) was dissolved in methanol (150 mL) to which was added 5% Pd/C (2.3 g) as a slurry in toluene (10 mL). The autoclave was charged to 20 bar with hydrogen and the reaction mixture was stirred for 2 hours at room temperature. The mixture was filtered through celite and the filtrates concentrated under reduced pressure to afford (I-10c). The product was used in the next step without further purification. $^1$H NMR (CDCl$_3$, 300 MHz): δ 4.92 (1H), 4.38 (1H), 3.92 (2H), 3.73 (3H), 3.35 (2H), 1.5-1.8 (4H), 1.43 (9H), 1.2-1.4 (2H).

Intermediate: (R)-2-amino-3-(tetrahydro-2H-pyran-4-yl)propanoic acid (I-10d)

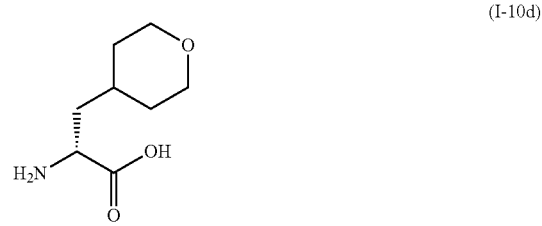 [SMILES: N[C@H](CC1CCOCC1)C(=O)O]

First, Intermediate (I-10c) (22.9 g, 80.0 mmol) was suspended in 6N aqueous HCl (200 mL) and heated at 100° C. overnight. The mixture was cooled to room temperature and extracted with 20% ethyl acetate/hexane (100 mL) to remove any unwanted organics. The aqueous phase was concentrated under reduced pressure and co-distilled with toluene (2×200 mL) to afford the HCl salt of (I-10d), giving a yield of 17.9 g; 108% (off-white powder, presumed damp with water or toluene): $^1$H NMR (d$_6$-DMSO, 300 MHz) δ 8.49 (3H), 3.79 (3H), 3.19 (2H), 2.44 (1H), 1.4-1.9 (5H), 1.12 (2H). Secondly, the HCl salt of (I-10d) (11.6 g, 55.3 mmol) and isobutylene oxide (5.33 mL) were suspended in N,N-dimethylformamide (120 mL) in 4 Anton Paar 30 mL microwave vials. The mixtures were reacted at 100° C. for 1 hour and allowed to cool. The mixtures were washed out of the vials with ethyl acetate (50 mL each), combined and stirred briskly in further ethyl acetate (total volume 500 mL) for 10 minutes, during which time a thick cream-coloured suspension formed. The solids were filtered off, broken up with a spatula and dried in a vacuum oven at 50° C. overnight to afford Intermediate (I-10d)

Intermediate: (R)-2-hydroxy-3-(tetrahydro-2H-pyran-4-yl)propanoic acid (I-10e)

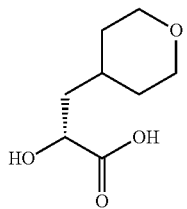

(I-10e)

Intermediate (I-10d) (7.68 g, 44.3 mmol) was dissolved in 1N H$_2$SO$_4$ (140 mL) and cooled to 0° C. under argon. NaNO$_2$ (4.6 g, 66.45 mmol) as a solution in water (25 mL) was introduced dropwise under the surface of the mixture and the whole stirred overnight. The mixture was extracted with ethyl acetate (100 mL). The aqueous phase was extracted with further ethyl acetate (5×100 mL). The aqueous phase was cooled to 0° C. under argon and re-dosed with concentrated H$_2$SO$_4$ (3.5 mL) and NaNO$_2$ (4.6 g, 66.45 mmol) as a solution in water (25 mL) and stirred overnight. The mixture was extracted with ethyl acetate (6×100 mL), re-dosed as above, stirred overnight and finally extracted a third time with ethyl acetate (6×100 mL). All 1800 mL of organics were combined and stripped to afford compound (I-10e) with a yield of 7.0 g (91%) as an orange oil. $^1$H NMR (CD$_3$OD, 300 MHz): δ 4.20 (1H), 3.92 (2H), 3.39 (2H), 1.7 (2H), 1.6 (2H), 1.27 (2H).

Intermediate: (R)-methyl 2-hydroxy-3-(tetrahydro-2H-pyran-4-yl)propanoate (I-10f)

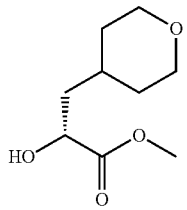

(I-10f)

Intermediate (I-10e) (9.0 g, 51 mmol) was dissolved in methanol (100 mL) and stirred. HCl was sparged in to the mixture for 15 minutes (exothermic 20° C. to 65° C.) and the whole was refluxed for 7 hours and allowed to cool. The mixture was stripped to approximately ⅓ volume, diluted with water (100 mL) and extracted with ethyl acetate (2×100 mL). The organics were stripped and the crude product puri- fied by dry-flash chromatography (SiO$_2$, ethyl acetate and hexanes, 10 to 20%)) to 3.8 g of (I-10f). The aqueous phase was re-extracted with ethyl acetate (2×200 mL), stripped, and re-purified to a further 1.2 g of (I-10f): $^1$H NMR (CDCl$_3$, 300 MHz): δ 4.24 (1H), 3.95 (2H), 3.78 (3H), 3.39 (2H), 2.73 (1H), 1.83 (1H), 1.52-1.75 (4H), 1.22-1.42 (1H).

Intermediate: (R)-methyl 3-(tetrahydro-2H-pyran-4-yl)-2-(trifluoromethylsulfonyloxy)-propanoate (I-10g)

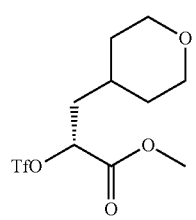

(I-10g)

Intermediate (I-10f), (1.21 g, 6.43 mmol) was dissolved in anhydrous dichloromethane (60 mL) under nitrogen. The mixture was stirred in an ice bath, and lutidine (1.6 mL) was added. Triflic anhydride (1.95 mL, 11.6 mmol) was added dropwise, and the reaction was stirred for 60 minutes then was diluted with methyl tert-butyl ether, and washed 3 times with 3:1 brine/1 N HCl. The organic layer was dried over MgSO$_4$, filtered, evaporated, and dried under high vacuum to afford (I-10g), which was utilized in the following reaction without further purification.

Intermediate: (S)-methyl 3-(tetrahydro-2H-pyran-4-yl)-2-(4-(trifluoromethyl)-1H-imidazol-1-yl)pro- panoate (I-10h)

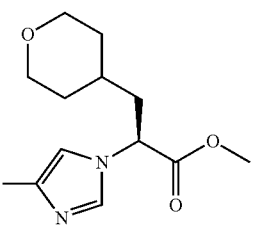

(I-10h)

4-(trifluoromethyl)-1H-imidazole (Flourine Chemicals, Shanghai, China) (291 mg) was stirred in 20 mL anhydrous THF at room temperature under nitrogen. A lithium bis(tri- methylsilyl)amide solution (1.96 mL, 1.0 M in THF) was added. After 50 minutes, a solution of intermediate (I-10g) (685 mg) in 10 mL anhydrous THF was added. The reaction was stirred for 2 hours. The reaction was quenched with saturated ammonium chloride and diluted with brine and ethyl acetate. The aqueous layer was extracted, dried, filtered, and then concentrated. The resulting residue was purified (Combi-flash, Redi-sep 40 g, 30% ethyl acetate/heptane gradient to 100% ethyl acetate/heptane) to afford (I-10h): m/z 307.4 (M+H)⁺.

Intermediate: 5-(methylsulfonyl)-1H-tetrazole (I-11a)

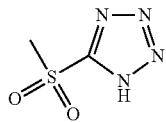

To a stirred solution of 5-(methylthio)-1H-tetrazole (300 mg; Aldrich Chemical Company, Inc., Milwaukee, Wis.) in THF (15 mL) and water (15 mL) was added potassium peroxomonosulfate (Oxone®, DuPont Specialty Chemicals, Deepwater, N.J., USA) (3.18 g). After stirring at room temperature for five days, the reaction mixture was filtered and the filtercake was washed with THF. The filtrate was concentrated under reduced pressure. Crude NMR showed this to be a mixture of desired product and starting material, so the mixture was taken up in methanol and treated with potassium peroxomonosulfate (Oxone®, DuPont Specialty Chemicals, Deepwater, N.J., USA). After stirring at room temperature for five days, the reaction mixture was filtered and the filtercake was washed with methanol. The filtrate was concentrated under reduced pressure to afford 0.400 g of impure (I-11a) as a solid which was used in the next step without purification; m/z 146.9 (M−H)⁻.

Intermediate: (S)-methyl 3-cyclopentyl-2-(5-(methylsulfonyl)-2H-tetrazol-2-yl)propanoate (I-11b)

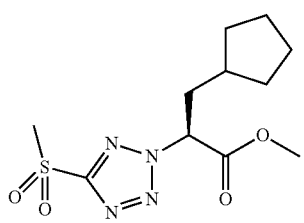

To a stirred solution of 200 mg of (I-11a) in anhydrous THF (10 mL) under nitrogen was added lithium bis(trimethylsilyl)amide (0.276 mL, 1 M in THF). After stirring for 40 minutes, a solution of Intermediate (I-1c) (414 mg) in anhydrous THF (2 mL) was added dropwise. After 2 hours, the reaction was quenched with aqueous saturated NH₄Cl and extracted with ethyl acetate twice. The combined organics were dried over MgSO₄ and purified by flash chromatography (10 g snap Biotage, 0-10% methanol in dichloromethane) to give 0.180 g of (I-11b) as an oil; m/z 303.1 (M+H)⁺.

Intermediate: (R)-2-amino-3-(tetrahydrofuran-2-yl)propanoic acid (I-12a)

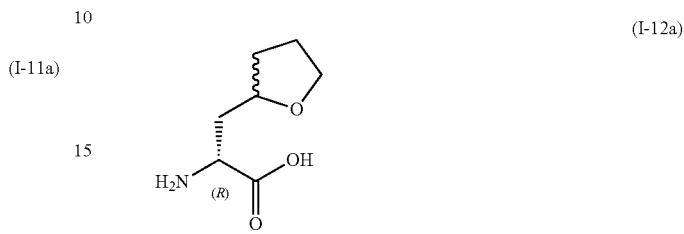

In a 400 mL beaker, D-2-furyl alanine (8.16 g, 52.6 mmol; Chem-Impex International, Inc., Wood Dale, Ill.) was slurried in water (200 mL) with 10% Pd/C (0.85 g). The beaker was placed in the bottom of a 2L stainless steel autoclave, charged to 20 bar (290 psi) with hydrogen and stirred for 5 hours at RT. TLC (1:1:1:1:1 toluene/acetone/butan-1-ol/water/acetic acid) showed some starting material remained. The reaction was re-charged with hydrogen to 20 bar and stirred overnight at RT, after which time TLC showed that starting material was no longer present. The mixture was filtered through a pad of celite (pad washed with 2×200 ml water), and the combined filtrates stripped to afford (I-12a) as a brown solid that was a mixture of diastereomers (8.4 g, 52.8 mmol, 100%): ¹H NMR (400 MHz, TFA-d): δ 84.60 (2 H), 4.12 (2 H), 2.58 (1 H), 2.40 (2 H), 2.1-2.35 (4 H), 1.89 (2 H).

Intermediate: (R)-2-hydroxy-3-(tetrahydrofuran-2-yl)propanoic acid (I-12b)

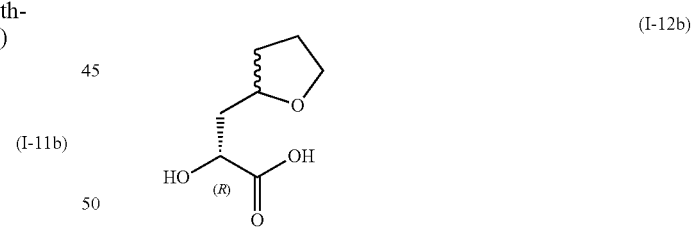

Intermediate (I-12a) (8.4 g, 52. 8 mmol) was dissolved in 1N H₂SO₄ (160 mL) and cooled in an ice/brine bath to 0° C. NaNO₂ (5.46 g, 79.2 mmol) as a solution in water (20 mL) was trickled in under the surface of the solution, and the mixture stirred overnight, gradually warming to RT. The mixture was extracted with ethyl acetate (6×100 mL), TLC (TA-BWA) showed product in each fraction, tailing off towards the end, TLC of the aqueous phase showed starting material remained. The aqueous phase was cooled to 3° C. and carefully re-dosed with conc. H₂SO₄ (4.5 mL), followed by further NaNO₂ (5.46 g, 79.2 mmol) in water (20 mL) at −2° C. The mixture was warmed to room temperature overnight, and the following morning extracted and re-dosed as above, three more times. The final extracts showed no significant amount of product, and no obvious starting material in the aqueous phase. The combined organics were stripped to afford (I-12b) as an orange oil that was a mixture of diastereomers (8.34 g, 52.0 mmol, 98%), known to be slightly impure by NMR: $^1$H NMR (400 MHz, CD$_3$OD): δ 4.22 (1 H), 4.05 (1 H), 3.81 (1 H), 3.69 (1 H), 1.82-2.10 (5 H), 1.55 (1 H).

Intermediate: (R)-methyl 2-hydroxy-3-(tetrahydrofuran-2-yl)propanoate (I-12c)

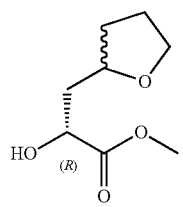
(I-12c)

Intermediate (I-12b) (4.23 g, 26.4 mmol) was dissolved in HPLC grade methanol (100 mL) and to this Amberlyst-15 (4.23 g) was added in one portion, and the mixture stirred for 72 hours. An aliquot was filtered and stripped, and the $^1$H NMR showed only product present. The mixture was combined for workup with two other runs (1 g, 6.2 mmol of I-12b and 1.99 g, 12.4 mmol of I-12b). The combined mixtures were filtered through a pad of Celite, and the pad washed with ethyl acetate (2×100 mL), the combined filtrates were stripped to give the crude product as a yellow oil (6.2 g, 35.6 mmol, 79%). The crude product was purified by column chromatography (ethyl acetate/hexane 1:1), to afford (I-12c) as a pale yellow oil that was a mixture of diastereomers (3.9 g, 22.4 mmol, 43%): $^1$H NMR (400 MHz, CDCl$_3$): δ 4.33 (1 H), 3.73 (1 H), 3.73 (2 H), 3.72 (3 H), 1.8-2.1 (5 H), 1.51 (1 H).

Intermediate: (2R)-methyl 3-(tetrahydrofuran-2-yl)-2-(trifluoromethylsulfonyloxy)propanoate (I-12d)

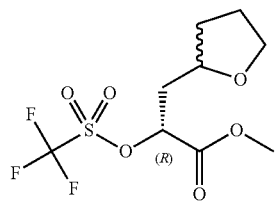
(I-12d)

Intermediate (I-12c) (1.57 g, 9 mmol) was added to a nitrogen purged flask and dissolved in 18 mL anhydrous dichloromethane. The temperature was brought to 0° C. and 2,6-lutidine (1.8 mL, 16 mmol) was added followed by dropwise triflic anhydride (2.48 mL, 14.8 mmol). This yellow solution was stirred at 0° C. for 45 min before adding ether and washing with a mixture of water and 1N HCl (pH=1). The organic layer was washed with brine and then dried over MgSO$_4$ and concentrated to afford 3.40 g of (I-12d) as a yellow oil that was a mixture of diastereomers. This was carried on without characterization.

Intermediate: (S)-methyl 3-(tetrahydrofuran-2-yl)-2-(4-(trifluoromethyl)-1H-imidazol-1-yl)propanoate (I-12e)

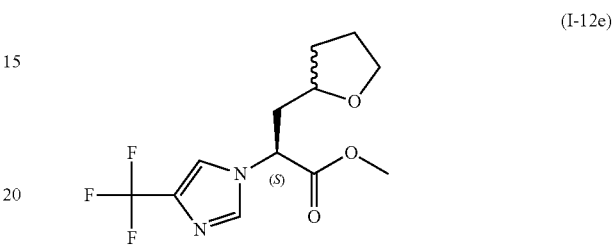
(I-12e)

4-(Trifluoromethyl)-1H-imidazole (397 mg, 2.9 mmol) was stirred in anhydrous THF (4 mL) under nitrogen and lithium hexamethyldisilazide (2.90 mL, 1 M in THF, 2.9 mmol) was added. This was stirred at RT as a solution for 90 min before adding a solution of intermediate (I-12d) (900 mg, 2.9 mmol) in 3 mL anhydrous THF dropwise. The reaction was stirred as a mixture at RT for 3 hr. The reaction was quenched with saturated NH$_4$Cl solution, and extracted with ethyl acetate twice. The combined organics were dried over MgSO$_4$, filtered, and concentrated under reduced pressure. The residue was chromatographed (Isco, 12 gram RediSep Column eluting with 30-50% ethyl acetate/Heptane) to afford 370 mg (43%) of (I-12e) as a yellow solid that was a mixture of diastereomers; m/z 293.1 (M+H)$^+$.

Intermediate: (R)-methyl 2-hydroxy-3-(1H-pyrazol-1-yl)propanoate (I-13a)

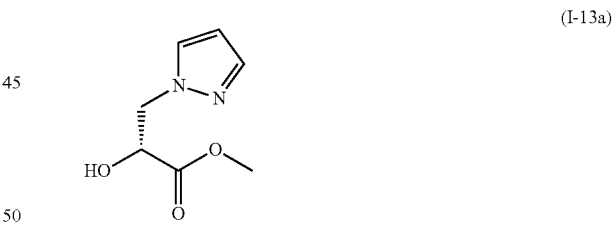
(I-13a)

In a 50 mL round bottomed flask, methyl-2R-glycidate (2.5 g, 24.5 mmol) and pyrazole (4.17 g, 61.2 mmol) were dissolved in industrial methylated spirits (25 mL) and refluxed for 5 hours. A 0.2 mL sample was withdrawn, stripped and tested by $^1$H NMR, showing all of the methyl-2R-glycidate was consumed. The reaction was allowed to cool, stripped and codistilled with methanol (20 mL). The crude material, a yellow oil, (6.67 g) was combined with 130 mg of crude material from a previous experiment, and purified by column chromatography (20%-50% ethyl acetate/hexane). Two fractions were collected and analysed by NMR, the primary spot material contained approximately 5% pyrazole, and the secondary spot approx 27%. The two fractions were re-purified separately to afford (I-13a) as a yellow oil. (2.6 g, 15.2 mmol, 62%): $^1$H NMR (400 MHz, CDCl$_3$): δ 7.50 (1 H), 7.42 (1 H), 6.24 (1 H), 4.55 (1 H), 4.47 (2 H), 3.77 (3 H).

Intermediate: (R)-methyl 3-(1H-pyrazol-1-yl)-2-(trifluoromethylsulfonyloxy)propanoate (I-13b)

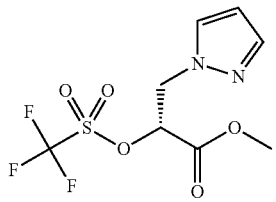

(I-13b)

Intermediate (I-13a) (800 mg, 4.7 mmol) was weighed into a flask and dissolved in dry dichloromethane (60 mL) under nitrogen. The mixture was stirred in an ice bath, and 2,6-lutidine (1.2 mL, 10 mmol) was added. Trifluoromethane sulfonic acid anhydride (1.4 mL, 8.5 mmol) was added dropwise, and the reaction was stirred for 60 minutes, diluted with methyl tert-butyl ether (50 mL), and washed three times with 3:1 brine:HCl. The organic layer was dried over sodium sulfate, filtered, concentrated under reduced pressure, and dried under high vacuum to affor (I-13b) as a light brown oil (1.42 g, 4.7 mmol, 100%). The compound was used crude in the next step; $^1$H NMR (400 MHz, CDCl$_3$) δ 7.61 (1 H), 7.47 (1 H), 6.27-6.37 (1 H), 5.50-5.54 (1 H), 4.56-4.85 (2 H), 3.88 (3 H).

Intermediate: (S)-methyl 3-(1H-pyrazol-1-yl)-2-(4-(trifluoromethyl)-1H-imidazol-1-yl)propanoate (I-13c)

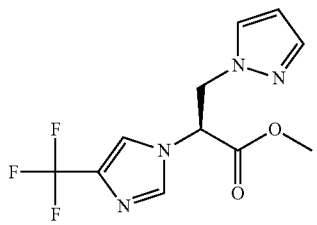

(I-13c)

4-(Trifluoromethyl)-1H-imidazole (640 mg, 4.7 mmol) was stirred in dry THF (30 mL) at room temperature under nitrogen. Lithium hexamethyldisilazide (1M in THF, 4.2 mL, 4.2 mmol) was added. After 45 minutes, a solution of Intermediate (I-13b) (1.42 g, 4.7 mmol) in dry THF (20 mL) was added. The reaction was stirred for 12 hours. The reaction was quenched with saturated ammonium chloride and diluted with brine and ethyl acetate. Enough water was added to dissolve the precipitated salts. The aqueous layer was extracted with ethyl acetate, and the combined organics were dried over sodium sulfate, filtered, and concentrated under reduced pressure. The residue was purified by silica gel chromatography, eluting with 100% heptane gradient to 80% ethyl acetate/heptane. The appropriate fractions were combined, evaporated, and dried under high vacuum to afford (I-13c) as a yellow oil (689 mg, 2.39 mmol, 57%). m/z 289.2 (M+H)$^+$.

Intermediate: (S)-3-cyclopentyl-N-(5-((S)-2,2-dimethyl-1,3-dioxolan-4-yl)pyrazin-2-yl)-2-(4-(trifluoromethyl)-1H-imidazol-1-yl)propanamide (I-14a)

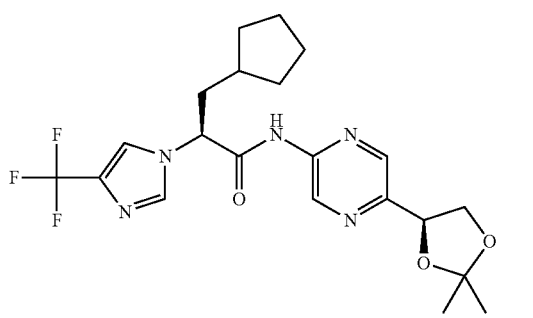

(I-14a)

To a solution of (I-8b) (167 mg, 0.605 mmol) in 3 mL anhydrous dichloromethane at 0° C. was added dropwise oxalyl chloride (0.129 mL, 1.45 mmol) followed by 2 drops of N,N-dimethylformamide. This was stirred at 0° C. for 5 minutes and then at room temperature for 60 minutes before concentrating under reduced pressure. 1,2-Dichloroethane was added and concentrated to ensure all oxalyl chloride was removed. This residue was then dissolved in 3 mL anhydrous dichloromethane and brought to 0° C. In a separate vial (S)-5-(2,2-dimethyl-1,3-dioxolan-4-yl)pyrazin-2-amine (118 mg, 0.605 mmol), prepared as in Chen, et al. US 2004/0147748, was combined with dichloromethane (2 mL) and pyridine (0.147 mL, 1.82 mmol). The amine solution was then added to the acid chloride solution. The ice bath was allowed to melt and the reaction was stirred for 15 h. The reaction mixture was diluted with dichloromethane (50 mL) and 1N HCl (5 mL), the layers were separated, and the aqueous layer was extracted with dichloromethane. The combined organics were dried over MgSO$_4$ and purified by silica gel chromatography (12g-Snap Biotage, heptane/ethyl acetate) to give three fractions of impure desired material. These were combined, diluted with dichloromethane, washed with saturated aqueous sodium bicarbonate and dried over MgSO$_4$. This was filtered and concentrated in vacuo to afford 76 mg of (I-14a) as an oil; m/z 454.1 (M+H)$^+$.

Intermediate: 3-(trifluoromethyl)-1H-1,2,4-triazole (I-15a)

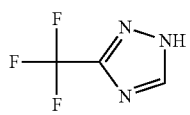

(I-15a)

Hydrazine monohydrate (4.8 g, 96 mmol) was dissolved in industrial methylated spirits (160 mL) and cooled to 0° C. before ethyl trifluoroacetate (14 g, 100 mmol; Aldrich Chemical Company, Inc., Milwaukee, Wis.) was added dropwise. The resulting reaction mixture was then warmed to ambient temperature and stirred for 1 hour. After this time, the solvent was removed under vacuum and the residue re-dissolved in industrial methylated spirits (100 mL). Formamidine acetate (9.9 g, 95 mmol; Aldrich Chemical Company, Inc., Milwaukee, Wis.) was then added and the reaction mixture heated to 80° C. for 2.5 hours. The reaction was then cooled to ambient temperature and the solvent removed under vacuum. To the residue was then added NaHCO$_3$ (aq.) (100 mL), and the product was extracted with ethyl acetate (2×100 mL), dried over MgSO$_4$, filtered and the solvent removed under vacuum. The crude product was then purified by flash chromatography (1:3 hexane/ethyl acetate), giving ~10 g of a pale peach oil, which crystallised on standing overnight. The crystals were then filtered, washed with hexane and dried overnight in an oven to afford (I-15a) as colorless crystals (8.73 g, 66% yield): $^1$H NMR (400 MHz, DMSO-d$_6$): δ 8.81 (1 H).

Intermediate: (S)-methyl 3-cyclopentyl-2-(3-(trifluoromethyl)-1H-1,2,4-triazol-1-yl)propanoate (I-15b)

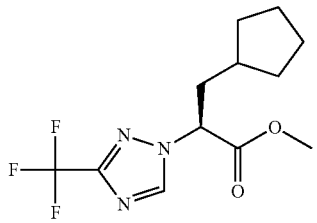

(I-15b)

Intermediate (I-15a) (248 mg, 1.8 mmol) was dissolved in dry THF (20 mL) under argon and lithium hexamethyldisilazide (1 M in THF, 1.62 mL, 1.62 mmol) was added. The reaction mixture was then stirred at ambient temperature for 30 minutes before Intermediate (I-1c) (550 mg, 1.8 mmol) was added as a solution in THF (20 mL), and the resulting reaction mixture stirred at ambient temperature for 16 hours. After this time, the reaction was quenched by the addition of NH$_4$Cl (aq.) (10 mL) at 0° C. and the product was extracted with ethyl acetate (2×40 mL), dried over MgSO$_4$, filtered and the solvent removed under vacuum. The crude product was then purified by flash chromatography (2:1 hexane/ethyl acetate) to afford (I-15b) as a colorless oil (198 mg, 42% yield): $^1$H NMR (400 MHz, CDCl$_3$): δ 8.34 (1 H), 5.10 (1 H), 3.78 (3 H), 2.28-2.16 (2 H), 1.83-1.76 (1 H), 1.74-1.47 (6 H), 1.21-1.04 (2 H).

Intermediate: (S)-3-cyclopentyl-2-(3-(trifluoromethyl)-1H-1,2,4-triazol-1-yl)propanoic acid (I-15c)

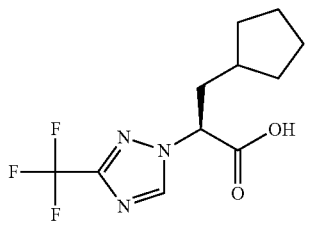

(I-15c)

6N HCl (10 mL) was added to Intermediate (I-15b) (380 mg, 1.30 mmol) and the mixture was warmed to 95° C. for 16 hours and then allowed to cool. Solid potassium carbonate was added to bring the pH to about 4. The mixture was diluted with water and ethyl acetate. The aqueous layer was extracted once with ethyl acetate. The combined organics were washed with brine, dried over sodium sulfate, filtered, evaporated, and dried under high vacuum to afford (I-15c); m/z 277.9 (M+H)$^+$.

Intermediate: (R)-methyl 3-cyclohexyl-2-(trifluoromethylsulfonyloxy)propanoate (I-16a)

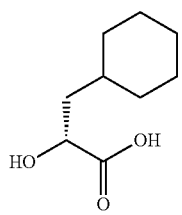

(I-16a)

To a 100 mL round bottom flask containing D-cyclohexylalanine hydrochloride (10 g, 48 mmol; Chem-Impex International, Inc., Wood Dale, Ill.) was added 2N H$_2$SO$_4$ (50 mL), and the stirred solution was cooled to 0° C. To this solution was added NaNO$_2$ (5 g, 72.2 mmol) as a solution in H$_2$O (5 mL) dropwise over 5 min. The reaction mixture was stirred for 3 hr at 0° C. and then the bath was allowed to melt and come to room temperature overnight. The solution was transferred to a separatory funnel and extracted with methyl tert-butylether twice. The combined organics were dried over MgSO$_4$ and concentrated to afford 6 g of a mixture of product and starting material as a pale oil. The aqueous layer was placed in the original round bottom flask and another 4 mL conc. H$_2$SO$_4$ was added. After cooling to 0° C., a solution of NaNO$_2$ (2 g) in H$_2$O (0.5 mL) was added. The reaction was stirred at 0° C. for several hours before being allowed to come slowly to room temperature overnight and stirred at room temp for 16 hours. The 6 g mixture was dissolved in 2N H$_2$SO$_4$ (50 mL), and the stirred solution was cooled to 0° C. To this solution was added NaNO$_2$ (2.5 g, 36.1 mmol) as a solution in H$_2$O (5 mL) dropwise over 5 min. The reaction mixture was stirred for 3 hr at 0° C. and then the bath was allowed to melt and come to room temperature overnight. Both reactions were combined and transferred to a separatory funnel and then extracted with methyl tert-butylether twice. The combined organics were dried over MgSO$_4$ and concentrated to afford (I-16a) (4.8 g) as pale oil; m/z 171.1 (M−H)$^−$.

Intermediate: (R)-methyl 3-cyclohexyl-2-hydroxypropanoate (I-16b)

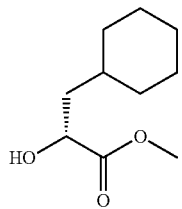

(I-16b)

To a solution of intermediate (I-16a) (6.3 g, 36.58 mmol) in anhydrous methanol (50 mL) was added thionyl chloride (4. mL, 54.9 mmol) dropwise and then the reaction was refluxed for 60 minutes. It was then cooled down and concentrated in vacuo. The residue was partitioned between ethyl acetate and sat. NaHCO$_3$. The aqueous layer was extracted with ethyl acetate and the combined organics dried over MgSO$_4$, filtered, and evaporated to give a crude oil. The crude product was purified with silica gel chromatography (Biotage 40+M, eluting with 0-30% (3 CV), 30% (3 CV), 30-100% (1 CV), 100% (2 CV) ethyl acetate/heptane) to afford (I-16b) (2.4 g) as a colorless oil: $^1$H NMR (400 MHz, CDCl$_3$): δ 4.12-4.34 (1 H), 3.77 (3 H), 2.45-2.72 (1 H), 1.80 (1 H), 1.42-1.75 (7 H), 1.04-1.35 (3 H), 0.71-1.01 (2 H).

Intermediate: (R)-methyl 3-cyclohexyl-2-(trifluoromethylsulfonyloxy)propanoate (I-16c)

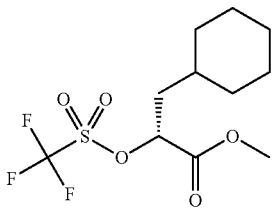

(I-16c)

2,6-Lutidine (0.354 mL, 3.04 mmol) was added to a flask containing intermediate (I-16b) (298 mg, 1.6 mmol) in anhydrous dichloromethane (7 mL) purged with nitrogen at 0° C. To this was added bis(trifluoromethanesulfonic)anhydride (0.469 mL, 2.72 mmol) and stirred for 40 min. The solution was observed to be light yellow. The reaction mixture was concentrated and taken up in diethyl ether. This was washed with brine (3×), and aq. 1N HCl (3×). The organic layer was dried over sodium sulfate, filtered, and concentrated afford (I-16c) (509 mg); m/z 319.0 (M+H)$^+$.

Intermediate: (S)-methyl 3-cyclohexyl-2-(4-(trifluoromethyl)-1H-imidazol-1-yl)propanoate (I-16d)

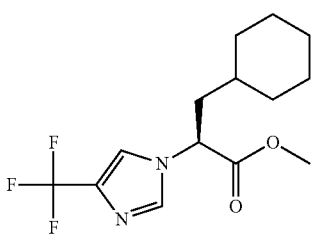

(I-16d)

4-(Trifluoromethyl)-1H-imidazole (204 mg, 1.50 mmol) was taken up in anhydrous THF and purged with nitrogen. To this added lithium hexamethyldisilazide (1.50 mL, 1.15 mmol, 1 M in THF) and the reaction was stirred as a solution for 40 min at room temperature. After 40 min, intermediate (I-16c) (478 mg, 1.28 mmol) in 2 mL of anhydrous THF was added dropwise. This was stirred at room temperature for 2 hours at which point the reaction had turned dark yellow. After 2 hours, the reaction mixture was quenched with aqueous saturated NH$_4$Cl. Ethyl acetate was added and the material transferred to a separatory funnel. The organic layer was washed with aq. 1M HCl (3×), water (3×), aqueous sodium bicarbonate and brine (2×). The organic layer was dried over sodium sulfate, filtered, and concentrated to a crude residue. Purification of the crude product was performed using a combiflash/isco companion system (SiO$_2$, with a gradient of 0-60% ethyl acetate/heptane) to afford (I-16d) as a yellow oil; m/z 305.0 (M+H)$^+$.

Intermediate: (S)-benzyl 6-(3-cyclohexyl-2-(4-(trifluoromethyl)-1H-imidazol-1-yl)propanamido)nicotinate (I-16e)

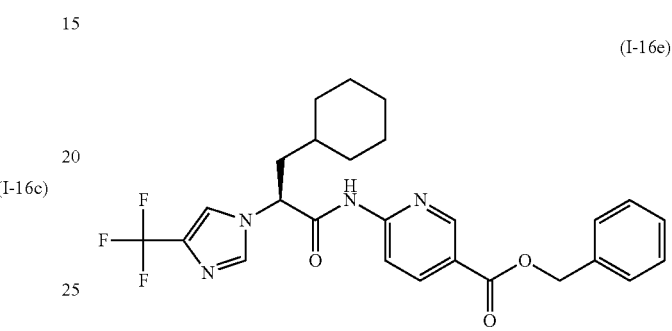

(I-16e)

Intermediate (I-28a) (272 mg, 1.19 mmol) was taken up in 4 mL of toluene. The amine was observed to be insoluble. Dimethylaluminum chloride (1.19 mL, 1.19 mmol) was added to this mixture. The solids dissolved and the solution was observed to be bright yellow/green. Within one minute, this solution was added to a 50° C. solution of intermediate (I-16d) (250 mg, 0.822 mmol) in 3 mL of toluene. This yellow solution was stirred at 50° C. for 2 hours then 0.3 eq more of dimethylaluminum chloride was added and stirred for another hour. The heat was discontinued and aqueous saturated Rochelle's salt (15 mL) was added and stirred for 0.5 hrs. 15 mL of ethyl acetate was used to transfer to a separatory funnel. The organic layer was washed with water (3×) and brine (2×). The organic layer was dried over sodium sulfate, filtered, and concentrated to a crude residue. Purification of the crude product was performed using a combiflash/isco companion system with a gradient of 0-50% ethyl acetate/heptane to afford (I-16e) as a clear foam; m/z 501.0 (M+H)$^+$.

Intermediate: (S)-methyl 3-cyclopentyl-2-(2-methyl-4-(trifluoromethyl)-1H-imidazol-1-yl)propanoate (I-17a)

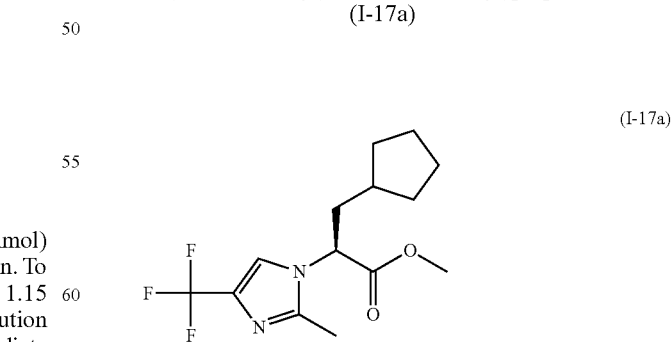

(I-17a)

To a stirred solution of 2-methyl-4-(trifluoromethyl)-1H-imidazole (Chireach USA LLC, San Diego, Calif.) (197 mg, 1.3 mmol) in anhydrous THF (8 mL) under N$_2$ was added a solution of lithium hexamethyldisilazide (1.24 mL, 1 M in hexanes, 1.24 mmol). After stirring for 45 minutes at room temperature, a solution of Intermediate (I-1c) (400 mg, 1.32 mmol) in 8 mL of anhydrous THF was added dropwise and stirring was continued for 4 hours at room temperature. It was then quenched with aqueous saturated NH₄Cl and extracted with ethyl acetate. The combined organic extracts were dried over MgSO₄, filtered, and concentrated. The resulting residue was purified by flash chromatography (SiO₂, heptane/ethyl acetate, 0 to 50%) to afford (I-17a) in 47% yield; m/z 305.4 (M+H)⁺.

Intermediate: (S)-benzyl 6-(3-cyclopentyl-2-(2-methyl-4-(trifluoromethyl)-1H-imidazol-1-yl)propanamido)nicotinate (I-17b)

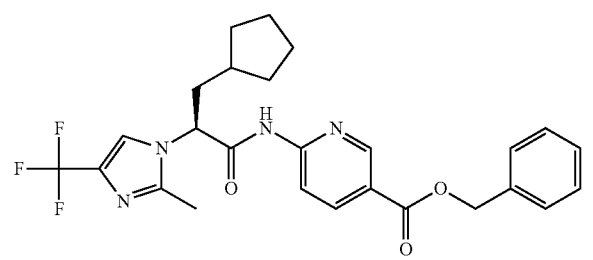
(I-17b)

Intermediate (I-28a) was taken up in 3 mL of toluene. The amine was observed to be insoluble. Dimethylaluminum chloride (0.44 mL, 1.0M in hexanes, 1.19 mmol) was added to this mixture. The solids dissolved and the solution was observed to be bright yellow/green. Within one minute, this solution was added to a 50° C. solution of intermediate (I-17a) in 2 mL of toluene. This yellow solution was stirred at 50° C. for 2 hours then another 0.3 eq of 1.0 M dimethylaluminum chloride was added and stirred for another hour. The reaction was cooled to room temperature over 1 hour and then saturated aqueous Rochelle's salt (15 mL) was added and stirred for 0.5 h. 15 mL of ethyl acetate was used to transfer the material to a separatory funnel. The organic layer was washed sequentially with water (3×) and brine (2×). The organic layer was dried over sodium sulfate, filtered and concentrated under reduced pressure. The crude residue was purified by silica gel chromatography (20-80% ethyl acetate/heptane) to afford (I-17b); m/z 501.4 (M+H)⁺.

Intermediate: (S)-methyl 3-cyclopentyl-2-(4-methyl-3-(trifluoromethyl)-1H-pyrazol-1-yl)propanoate (I-18a)

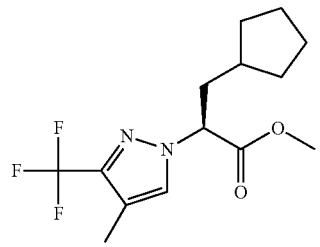
(I-18a)

To a stirred solution of 4-methyl-3-(trifluoromethyl)-1H-pyrazole (Ryan Scientific, Inc., Mt. Pleasant, S.C.) (197 mg, 1.3 mmol) in anhydrous THF (8 mL) under nitrogen was added a solution of lithium hexamethyldisilazide (1.24 mL, 1 M in hexanes, 1.24 mmol). After stirring for 45 minutes at room temperature, a solution of Intermediate (I-1c) (400 mg, 1.32 mmol) in 8 mL of anhydrous THF) was added dropwise and stirring was continued for 4 hours at room temperature. It was then quenched with aqueous saturated NH₄Cl and extracted with ethyl acetate. The combined organic extracts were dried over MgSO₄, filtered, and concentrated. The resulting residue was purified by flash chromatography (SiO₂, heptane/ethyl acetate, 0 to 50%) to afford (I-18a) in 70% yield; m/z 305.4 (M+H)⁺.

Intermediate: (S)-3-cyclopentyl-2-(4-methyl-3-(trifluoromethyl)-1H-pyrazol-1-yl)propanoic acid (I-18b)

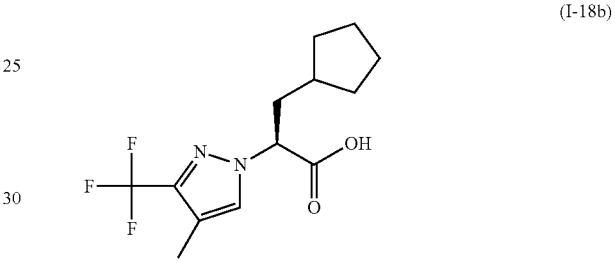
(I-18b)

6N HCl (2 mL) was added to Intermediate (I-18a) (89 mg, 0.29 mmol) and the mixture was warmed to 95° C. for 16 hours and then allowed to cool. Solid potassium carbonate was added to bring the pH to about 3. A precipitate crashed out. Ethyl acetate was added, and the mixture was stirred until everything was dissolved. The aqueous layer was extracted once with ethyl acetate. The combined organics were washed with brine, dried over sodium sulfate, filtered, evaporated, and dried under high vacuum to afford impure (I-18b) with some starting material present; m/z 290.9 (M+H)⁺.

Intermediate: (2S)-3-cyclopentyl-2-[4-(trifluoromethyl)-1H-imidazol-1-yl]propanamide (I-19a)

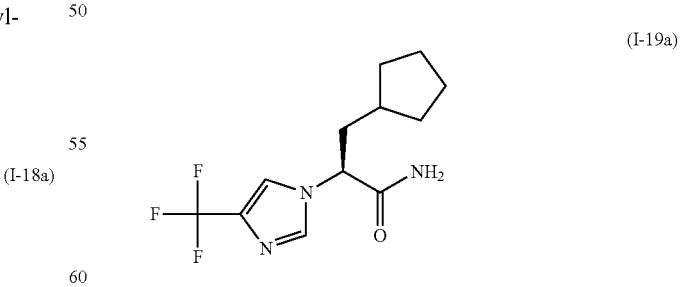
(I-19a)

Intermediate (I-8b) (150 mg, 0.54 mmol) in dichloromethane under nitrogen was treated with oxalyl chloride (0.1 mL, 1.1 mmol) and one drop of N,N-dimethylformamide. The reaction was stirred for 1 hr and then concentrated. The residue, dissolved in dichloromethane, was treated with ammonia in dioxane (0.5M, 3 mL). The resulting mixture was capped and stirred overnight. The reaction mixture was concentrated to afford (I-19a) (80 mg, 54%); m/z 276.1 (M+H)⁺.

Intermediate:
3-methyl-4-(trifluoromethyl)-1H-pyrazole (I-20a)

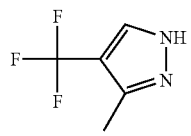

(I-20a)

A solution of 4,4,4-trifluorobutan-2-one (2.0 g, 16 mmol; Alfa Aesar, Ward Hill, Mass.) and 1,1-dimethoxy-N,N-dimethylmethanamine (4.2 mL, 32 mmol; Aldrich Chemical Company, Inc., Milwaukee, Wis.) in toluene (13 mL) was stirred at reflux for 4 h. The reaction was cooled and the mixture was concentrated in vacuo. The crude residue was taken up in ethanol (13 mL) and hydrazine (3.7 mL) was added. The mixture was stirred at room temperature overnight before concentrating in vacuo. The residue was redissolved in ethyl acetate and washed with water. The aqueous layer was reextracted with ethyl acetate three times. The combined organic layer was dried over sodium sulfate, filtered, and concentrated to afford impure (I-20a) as a red oil (1.28 g). This was carried on without further purification. ¹H NMR (400 MHz, CDCl₃): δ 7.73 (1 H), 2.42 (3 H).

Intermediates: (S)-methyl 3-cyclopentyl-2-(3-methyl-4-(trifluoromethyl)-1H-pyrazol-1-yl)propanoate (I-20b), (S)-methyl 3-cyclopentyl-2-(5-methyl-4-(trifluoromethyl)-1H-pyrazol-1-yl)propanoate (I-20c)

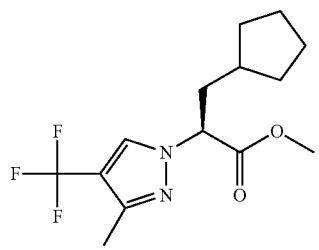

(I-20b)

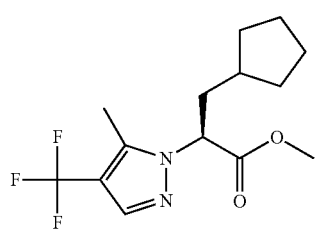

(I-20c)

Intermediate (I-20a) (150.1 mg, 1.00 mmol) was stirred in 5 mL of dry THF at room temperature under nitrogen. Lithium hexamethyldisilazide solution (1.0M in THF, 0.91 mL, 0.909 mmol) was added dropwise. After 50 minutes, a solution of intermediate (I-1c) (304 mg, 1.00 mmol) in 1 mL of dry THF was added. The reaction was stirred for 3 hours. The reaction was quenched with saturated aqueous ammonium chloride and extracted with ethyl acetate three times. The combined organic layer was concentrated and purified by silica gel chromatography (ISCO 12 g, ethyl acetate/heptane 30-100%) to afford a mixture of (I-20b) and (I-20c) as a yellow oil (153 mg); m/z 304.9 (M+H)⁺.

Intermediate: (S)-6-(3-cyclopentyl-2-(4-(trifluoromethyl)-1H-imidazol-1-yl)propanamido)nicotinoyl chloride (I-21a)

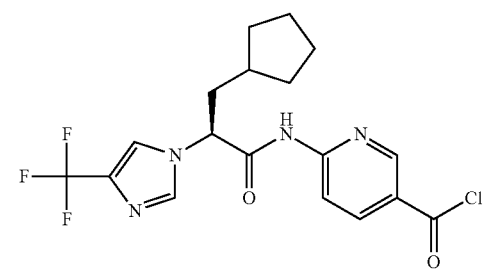

(I-21a)

Thionyl chloride (225 mg, 1.89 mmol) was added to a solution of the compound of Example 48 (150 mg, 0.387 mmol) in dichloromethane (1.5 mL) and the reaction stirred at room temperature for 1 hour. LCMS of an aliquot in methanol showed ~67% methyl ester. To the reaction mixture was added another 25 uL of thionyl chloride and this was stirred at room temp for another 30 minutes. Solvents were evaporated to afford 157 mg (100%) of (I-21a) as a grayish-white solid. LCMS in methanol to generate the methyl ester gave m/z 395.9 (M+H)⁺.

Intermediate: benzyl 5-aminopyrazine-2-carboxylate (I-22a)

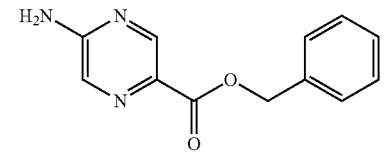

(I-22a)

5-aminopyrazine-2-carboxylic acid (493 mg, 3.54 mmol; Ark Pharm, Inc., Libertyville, Ill.) was stirred in dry N,N-dimethylformamide (3.0 mL) at room temperature under nitrogen. Solid potassium carbonate (742 mg, 5.37 mmol) was added, followed by benzyl bromide (0.43 mL, 3.6 mmol). The mixture was stirred for 22 hours and then diluted with ethyl acetate and water. The layers were separated, and the aqueous layer was extracted with ethyl acetate. The combined organics were washed with brine, dried over sodium sulfate, filtered, and evaporated. The residue was purified by silica chromatography using a 40 g pre-packed column, eluting with ethyl acetate. The product fractions were combined, evaporated, and dried under high vacuum to afford (I-22a) (161.2 mg, 0.70 mmol, 20%): m/z 229.9 (M+H)+.

Intermediate: (S)-3-cyclopentyl-2-(4-(methylsulfonyl)-1H-pyrazol-1-yl)propanoic acid (I-23a)

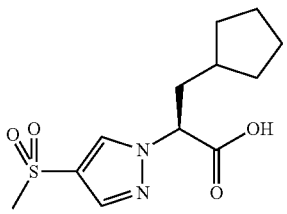

(I-23a)

6N HCl (4 mL) was added to Intermediate (I-4a2) (189 mg, 0.629 mmol) and the mixture was warmed to 95° C. for 16 hours and then allowed to cool to room temperature. Solid potassium carbonate was added to bring the pH to about 3. Ethyl acetate was added, and the mixture was stirred until everything was dissolved. The aqueous layer was extracted once with ethyl acetate. The combined organics were washed with brine, dried over sodium sulfate, filtered, evaporated, and dried under high vacuum to afford (I-23a); m/z 286.8 (M+H)+.

Intermediate: (S)-3-cyclopentyl-2-(4-(methylsulfonyl)-1H-imidazol-1-yl)propanoic acid (I-24a)

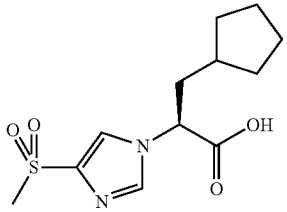

(I-24a)

6N HCl (1 mL) was added to Intermediate (I-7a3) (50 mg, 0.17 mmol) and the mixture was warmed to 95° C. for 16 hours and then allowed to cool to room temperature. Solid potassium carbonate was added to bring the pH to about 3. Ethyl acetate was added, and the mixture was stirred until everything was dissolved. The aqueous layer was extracted once with ethyl acetate. The combined organics were washed with brine, dried over sodium sulfate, filtered, evaporated, and dried under high vacuum to afford (I-24a); m/z 284.9 (M−H)−.

Intermediate: diethyl 6-aminopyridin-3-ylphosphonate (I-25a)

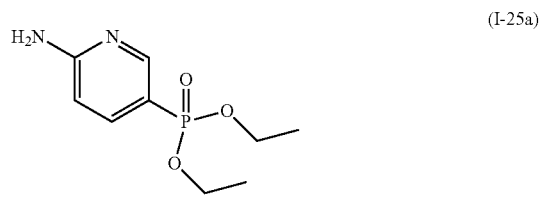

(I-25a)

A mixture of 2-amino-5-bromopyridine (5 g, 0.029 mol; Aldrich Chemical Company, Inc., Milwaukee, Wis.), diethyl phosphate (5.02 g, 0.036 mol), triethylamine (4.4 g, 0.043 mol), Pd(OAc)$_2$ (0.78 g, 3.4 mmol), triphenylphosphine (2.28 g, 8.7 mmol) in ethanol (100 mL) was refluxed for 14 hours under nitrogen. TLC (Petroleum ether/ethyl acetate=1:1) indicated that the reaction was complete. The resulting mixture was filtered, and the filtrate was concentrated in vacuo, the residue was purified by prep. HPLC to afford (I-25a) (4.3 g, 64.4%) as a white solid; m/z 231.3 (M+H)+.

Intermediate: Imidodicarbonic acid, N-(5-methyl-2-pyridinyl)-, C,C'-bis(1,1-dimethylethyl)ester (I-26a)

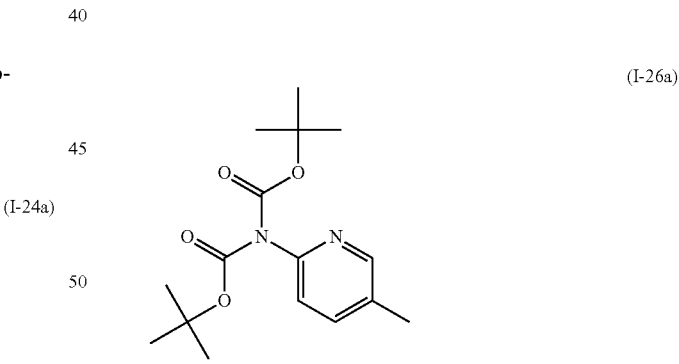

(I-26a)

To a solution of compound 2-amino-5-methylpyridine (10.0 g, 0.092 mol) in dichloromethane (200 mL) was added diisopropylethylamine (23.86 g, 0.185 mol) dropwise at 0° C. After the addition, a solution of (Boc)$_2$O (50.4 g, 0.231 mol) in dichloromethane (50 mL) was added to the mixture, followed N,N-dimethylaminopyridine (11.3 g, 0.092 mol), the resulting mixture was stirred at room temperature for 12 hours. TLC (petroleum ether/ethyl acetate=1:1) indicated that the reaction was complete. The mixture was washed with aq. NH$_4$Cl (50 mL), the residue was extracted with dichloromethane (50 mL×3). The combined organic layers were washed with brine, dried over Na$_2$SO$_4$ and evaporated in vacuo, the residue was purified by chromatography on silica to afford (I-26a) (11.4 g, 40%) as a white solid.

Intermediate: Imidodicarbonic acid, N-[5-(bromomethyl)-2-pyridinyl]-, C,C'-bis(1,1-dimethylethyl)ester (I-26b)

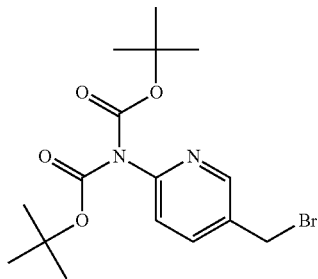

(I-26b)

A mixture of intermediate (I-26a) (5 g, 0.016 mol), N-bromosuccinimide (2.9 g, 0.016 mol), benzoyl peroxide (0.37 g, 0.0016 mol) in carbon tetrachloride (70 mL) was refluxed for 12 hours. TLC (petroleum ether/ethyl acetate=5:1) indicated that the reaction was not complete. The reaction mixture was filtered and the filtrate was concentrated in vacuo. The residue was purified by chromatography on silica to afford (I-26b) (3.1 g, 49.5%) as a white solid.

Intermediate: Imidodicarbonic acid, N-[5-[(diethoxyphosphinyl)methyl]-2-pyridinyl]-, C,C'-bis(1,1-dimethylethyl)ester (I-26c)

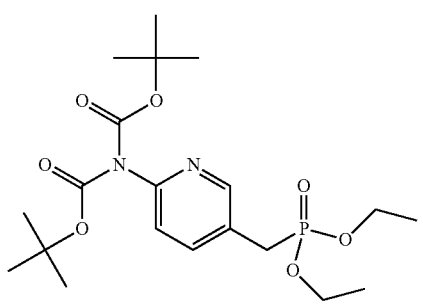

(I-26c)

A mixture of intermediate (I-26b) (4.0 g, 0.01 mol), triethyl phosphite (5.2 g, 31.2 mmol) in THF (100 mL) was refluxed for 72 hours. TLC (petroleum ether/ethyl acetate=1:1) indicated that the reaction was not complete. The reaction mixture was concentrated in vacuo, and the residue was purified by chromatography on silica to afford (I-26c) (4.4 g, 95.6%) as an oil.

Intermediate: diethyl(6-aminopyridin-3-yl)methylphosphonate (I-26d)

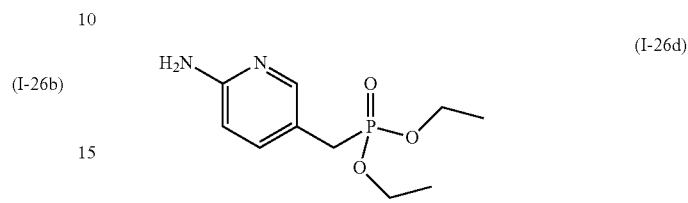

(I-26d)

A mixture of intermediate (I-26c) (4.7 g, 0.011 mmol) and trifluoroacetic acid (14 mL) in dichloromethane (60 mL) was stirred at room temperature for 2 hours. TLC (petroleum ether/ethyl acetate=0:1) indicated that the reaction was complete. The reaction mixture was washed with aq. NaHCO$_3$ (100 mL). The mixture was extracted with dichloromethane (20 mL×3). The combined organic phases were concentrated to afford (I-26d) (1.8 g, 69.7%) as a white solid; $^1$H NMR (400 MHz, CDCl$_3$): δ 7.87 (1 H), 7.37 (1 H), 6.40 (1 H), 4.33 (2 H), 3.98 (4 H), 2.90 (2 H), 1.20 (6 H).

Intermediate: 3-nitro-1H-pyrazole (I-27a)

(I-27a)

A solution of 1-nitro-1H-pyrazole (4.23 gm, 37.4 mmol; Oakwood Products, Inc., West Columbia, S.C.) in benzonitrile (42 mL) was heated to reflux for 2 hours. After cooling to 45° C., the reaction mixture, which was starting to precipitate, was poured into 175 mL hexanes. A white solid precipitated. This was collected by vacuum filtration, rinsed repeatedly with hexane and dried under high vacuum to afford 3.85 grams (91%) of (I-27a) as a white solid; $^1$H NMR (400 MHz, DMSO-d$_6$) δ 13.90 (1 H), 8.01 (1 H), 7.01 (1 H).

Intermediate: 3-nitro-1H-pyrazole (I-27b)

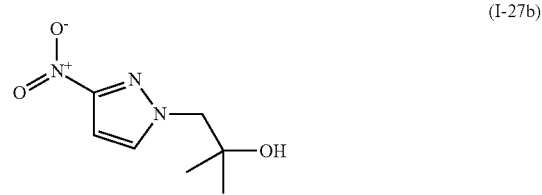

(I-27b)

Intermediate (I-27a) (830 mg, 7.0 mmol) was dissolved in anhydrous N,N-dimethylformamide (20 mL) in a heavy walled reaction tube. Potassium carbonate (1.408 g, 10.19 mmol) and dimethyl oxirane (1.016 g, 14.09 mmol; Aldrich Chemical Company, Inc., Milwaukee, Wis.) were added and the tube was sealed with a teflon screw cap and heated to 100° C. with stirring for 1 hour. After cooling to room temperature, the reaction was diluted with water (40 mL) and extracted with ethyl acetate (3×30 mL). The combined organic layers were dried over $Na_2SO_4$, filtered, and evaporated. The crude material was purified by silica gel flash chromatograpy (50-60% ethyl acetate/heptane over 40 minutes) to afford 985 mg (76%) of (I-27b) as a clear colorless oil. $^1$H NMR (400 MHz, $CDCl_3$) δ 7.59 (1 H), 6.90 (1 H), 4.17 (2 H), 2.11 (1 H), 1.23 (6 H).

Intermediate: 1-(2-methyl-2-(triethylsilyloxy)propyl)-3-nitro-1H-pyrazole (I-27c)

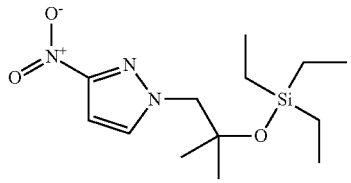
(I-27c)

Intermediate (I-27b) (948 mg, 5.12 mmol) was dissolved in anhydrous N,N-dimethyl formamide (25 mL) and cooled to 0° C. in an ice bath. To this was added chlorotriethylsilane (0.945 mL, 5.63 mmol) and imidazole (871 mg, 12.8 mmol). The mixture was stirred at 0° C. and then slowly allowed to warm to room temperature and stirred for two days. The reaction was diluted with ethyl acetate (75 mL) and washed with brine (50 mL). The aqueous layer was extracted with ethyl acetate (2×75 mL) and the combined organic layers were dried over $Na_2SO_4$, filtered, evaporated, then purified by silica gel flash chromatography (5-25% ethyl acetate/heptanes over 40 minutes) to afford 1.133 g of (I-27c) as a clear colorless oil; m/z 300.0 $(M+H)^+$.

Intermediate: 1-(2-methyl-2-(triethylsilyloxy)propyl)-1H-pyrazol-3-amine (I-27d)

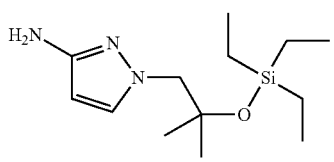
(I-27d)

In a Parr shaker bottle was placed 10% palladium on activated carbon (145 mg) and ethanol (10 mL) followed by a solution of intermediate (I-27c) (1.125 g, 0.65 mmol) in ethanol (40 mL). The bottle was then placed on the Parr shaker at 40 psi of hydrogen pressure for 1 h. The reaction was then filtered through a pad of celite and washed with ethanol. Concentration in vacuo afforded 981 mg (96.9%) of (I-27d) as a clear pale green oil; m/z 270.0 $(M+H)^+$.

Intermediate: benzyl 6-aminonicotinate (I-28a)

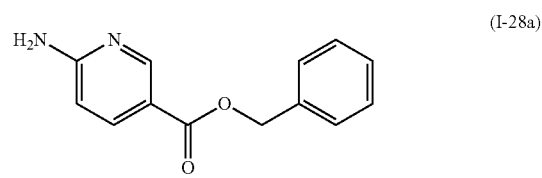 [SMILES: Nc1ccc(C(=O)OCc2ccccc2)cn1]
(I-28a)

To a stirred suspension of 6-aminonicotinic acid (100 g, 0.72 mol; Aldrich Chemical Company, Inc., Milwaukee, Wis.) in N,N-dimethylformamide (700 mL) with brisk mechanical stirring was added potassium carbonate (150 g, 1.08 mol) and the reaction was stirred for 10 min before the portionwise addition of benzyl bromide (95 mL, 0.80 mol). The reaction was stirred at room temperature overnight, then the solids were filtered off and washed thoroughly with ethyl acetate, and the solvent was removed under vacuum. The filter cake was dissolved in water and extracted with ethyl acetate. The residue after evaporation of N,N-dimethylformamide was combined with the ethyl acetate extracts (total volume 2 L of ethyl acetate) and the combined organic extracts washed with brine (5×500 mL), dried ($MgSO_4$) and the solvent removed under reduced pressure. The crude product was refluxed with 1:1 diethyl ether:hexane for 30 min then the solids filtered off (warm), washed with diethyl ether:hexane (1:1), and dried. This solid was precipitated from hot toluene (hot filtration required to remove dibenzylated material) and dried to afford (I-28a) (107.2 g, 65%) as an off-white solid; $^1$H NMR (DMSO-$d_6$): δ 8.50 (1 H), 7.82 (1 H), 7.34-7.29 (5 H), 6.84 (2 H), 6.43 (1 H), 5.23 (2 H); m/z 229.4 $(M+H)^+$.

Intermediate: tert-butyl 5-bromopyridin-2-ylcarbamate (I-29a)

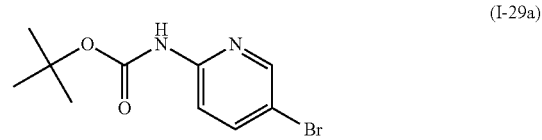
(I-29a)

To a solution of 2-amino-5-bromopyridine (8.65 g, 50 mmol) in THF (100 mL) was added lithium hexamethyldisilazide (105 mL, 105 mmol) under nitrogen at 0° C. After the addition, the mixture was stirred for 30 mins at 0° C. At this point, $(BOC)_2O$ (12 g, 55 mmol) was added to the reaction mixture and the mixture was stirred for another 30 mins at 0° C. TLC (petroleum ether/ethyl acetate=5:1) indicated the reaction was complete. The reaction mixture was washed with 1 N HCl (20 mL), and the residue was extracted with ethyl acetate (50 mL×3). The combined organic layers were washed with brine, dried over $Na_2SO_4$, and evaporated in vacuo. The residue was purified by chromatography on silica to afford (I-29a) (8 g, 58.6%) as a white solid.

Intermediate: butyl phosphenite (I-29b)

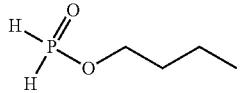

(I-29b)

A mixture of anilinium hypophosphite (20 g, 0.131 mol; Aldrich Chemical Company, Inc., Milwaukee, Wis.) and tetrabutyl orthosilicate (28.23 g, 0.088 mol; Aldrich Chemical Company, Inc., Milwaukee, Wis.) in THF (400 mL) was refluxed for 12 hours under nitrogen. The resulting mixture was cooled to give afford (I-29b) as a solution, which was used in the next step directly without further purification.

Intermediate: butyl methylphosphinate (I-29c)

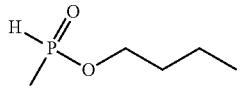

(I-29c)

To a solution of crude intermediate (I-29b) (400 mL THF solution, 0.131 mol) was added methyl iodide (12.44 g, 0.087 mol) and n-butyl lithium (42 mL, 0.105 mol) dropwise at −78° C. under nitrogen. After the addition, the reaction mixture was gradually warmed to room temperature. The resulting mixture was stirred at room temperature for 12 hours. TLC (petroleum ether/ethyl acetate=1:1) indicated the reaction was complete. The mixture was washed with aq. sodium bicarbonate (50 mL) and the residue was extracted with ethyl acetate (50 mL×3). The combined organic layers were washed with brine, dried over $Na_2SO_4$, and evaporated in vacuo. The residue was purified by chromatography on silica to afford (I-29c) (4.3 g, 24%) as an oil; $^1H$ NMR (400 MHz, $CDCl_3$): δ 7.82 (0.5 H), 6.48 (0.5 H), 3.88-4.09 (2 H), 1.59-1.66 (2 H), 1.45-1.53 (3 H), 1.32-1.44 (2 H), 0.84-0.90 (3 H).

Intermediate: tert-butyl 5-(ethoxy(methyl)phosphoryl)pyridin-2-ylcarbamate (I-29d)

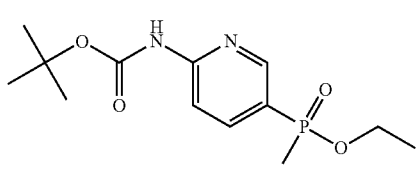

(I-29d)

A mixture of intermediate (I-29c) (2.7 g, 19.8 mmol), intermediate (I-29a) (5.4 g, 19.8 mmol), triethylamine (3.0 g, 29.7 mmol), Pd(OAc)$_2$ (0.533 g, 2.38 mmol), and triphenylphosphine (1.56 g, 5.94 mmol) in ethanol (100 mL) was refluxed for 18 hours under nitrogen. TLC (dichloromethane/methanol=10:1) indicated the reaction was complete. The reaction mixture was concentrated in vacuo, and the residue was washed with water and extracted with ethyl acetate (50 mL×3). The combined organic layers were washed with brine, dried over $Na_2SO_4$, and evaporated in vacuo. The residue was purified by chromatography on silica to afford (I-29d) (1.8 g, 30.4%) as an oil.

Intermediate: ethyl 6-aminopyridin-3-yl(methyl)phosphinate (I-29e)

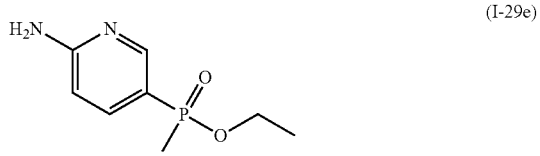

(I-29e)

A mixture of intermediate (I-29d) (1.8 g, 0.006 mol) and trifluoroacetic acid (20 mL) in dichloromethane (30 mL) was stirred at room temperature for 12 hours. TLC (dichloromethane/methanol=10:1) indicated the reaction was complete. The reaction mixture was washed with saturated aq. sodium bicarbonate (100 mL) and the mixture was extracted with dichloromethane (20 mL×3). The combined organic phases were concentrated to afford (I-29e) (1.1 g, 91.7%) as a light yellow solid; $^1H$ NMR (400 MHz, $CDCl_3$): δ 8.26-8.27 (1 H), 7.73-7.79 (1 H), 6.57-6.60 (1 H), 5.88 (2 H), 3.96-4.06 (1 H), 3.77-3.85 (1 H), 1.56-1.60 (3 H), 1.18-1.25 (3 H).

Intermediate: ethyl 6-((S)-3-cyclopentyl-2-(4-(trifluoromethyl)-1H-imidazol-1-yl)propanamido)pyridin-3-yl(methyl)phosphinate (I-29f)

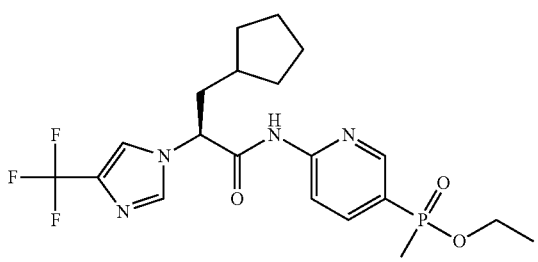

(I-29f)

To a solution of intermediate (I-8c) (0.6 g, 2.06 mmol) in dichloromethane (20 mL) was added intermediate (I-29f) (0.41 g, 2.06 mmol) and triethylamine (0.89 mL, 6.18 mmol) at room temperature, and the mixture was stirred for 12 hours at room temperature under nitrogen. TLC (dichloromethane/methanol=10:1) indicated the reaction was complete. The reaction mixture was concentrated in vacuo, the residue was purified by chromatography on silica to afford (I-29f) (250 mg, 26.6%) as an oil; $^1H$ NMR (400 MHz, $CDCl_3$): δ 9.98 (1

H), 8.61 (1 H), 8.22 (1 H), 8.00 (1 H), 7.71 (1 H), 7.51 (1 H), 5.05 (1 H), 4.07 (1 H), 3.82 (1 H), 2.14 (2 H), 1.39-1.78 (10 H), 1.01-1.33 (5 H).

Intermediate: 2,2-dimethyl-2,3-dihydrobenzo[e][1,3]oxazin-4-one (I-30a)

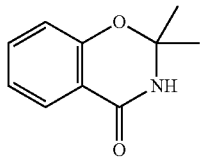
(I-30a)

To a solution of salicylamide (20.0 g, 0.146 mol; Aldrich Chemical Company, Inc., Milwaukee, Wis.) in 2,2-dimethoxypropane (300 mL) was added pyridinium p-toluenesulfonate (11.0 g, 0.044 mol) and then heated to reflux for 2 h. TLC (dichloromethane: methanol=20:1) indicated the reaction was complete. The solvent was removed and then the residue was taken up in ethyl acetate (150 mL). The solution was washed twice with sodium bicarbonate and once with brine. The organic layer was dried and concentrated under reduced pressure to afford (I-30a) (26.0 g, yield: 93.4%) as a yellow solid, which was used to next step without any purification.

Intermediate: 4-chloro-2,2-dimethyl-2H-benzo[e][1,3]oxazine (I-30b)

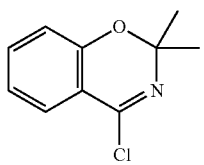
(I-30b)

To a solution of intermediate (I-30a) (42.0 g, 0.237 mol) in POCl$_3$ (200 mL) was added PCl$_5$ (71.95 g, 0.356 mol) and stirred at room temperature for 1 h. Then the mixture was heated to reflux overnight. The solvent was removed by distillation under atmospheric pressure and the residue was distilled under reduced pressure (85~86° C., 2.5 mm Hg) to afford crude (I-30b) (10.2 g, yield: 22.7%); $^1$H NMR (400 MHz, CDCl$_3$): δ 7.55-7.62 (1 H), 7.37-7.42 (1 H), 6.95-7.01 (1 H), 6.80-6.85 (1 H), 1.60-1.70 (6 H).

Intermediate: (1-oxy-pyridin-3-yl)-acetic acid ethyl ester (I-30c)

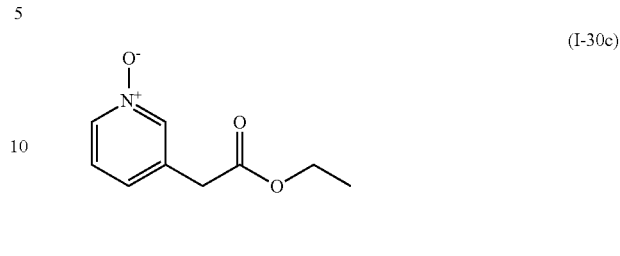
(I-30c)

A solution of ethyl 3-pyridylacetate (10.0 g, 0.061 mol; Aldrich Chemical Company, Inc., Milwaukee, Wis.) and m-chloroperoxybenzoic acid (36.87 g, 0.182 mol) in dichloromethane (300 mL) was stirred at RT overnight. TLC (dichloromethane: methanol=15:1) indicated the reaction was complete. The reaction mixture was quenched with Na$_2$SO$_3$, and then the solvent was removed under reduced pressure to give a crude product. The crude product was purified by chromatography on silica (dichloromethane: methanol=60:1→30:1→20:1) to give crude (I-30c) (15.2 g, 40.5% purity by LC-MS) as a solid.

Intermediate: ethyl 2-(6-(2,2-dimethyl-4-oxo-2H-benzo[e][1,3]oxazin-3(4H)-yl)pyridin-3-yl)acetate (I-30d)

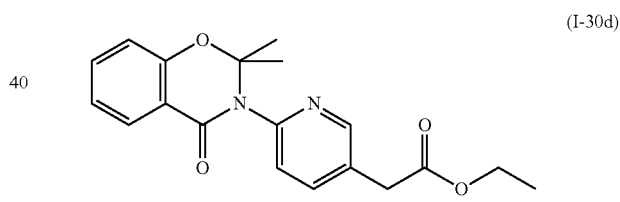
(I-30d)

A solution of intermediate (I-30c) (10.0 g, 55.19 mmol) and intermediate (I-30b) (10.0 g, 46.36 mmol) in 1,2-dichloroethane (100 mL) was heated to reflux for 3 days. TLC (dichloromethane: methanol=15:1) indicated the reaction was complete. The solvent was removed under reduced pressure to afford crude (I-30d) (11.0 g, yield: 69%) as an oil, which was used in the next step without any purification.

Intermediate: 2-(6-aminopyridin-3-yl)acetic acid hydrochloride (I-30e)

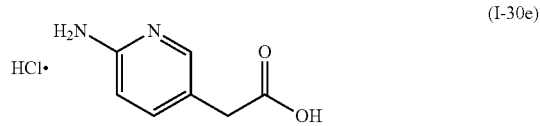 [SMILES: Nc1ccc(CC(=O)O)cn1]
(I-30e)

A solution of intermediate (I-30d) (11.0 g, 0.0324 mol) in conc. HCl (75 mL) was refluxed overnight. The solvent was removed under reduced pressure. The residue was dried by lyophilization to give crude intermediate (I-30e) (11.0 g) as a solid, which was put into next step without any purification.

Intermediate: methyl 2-(6-aminopyridin-3-yl)acetate (I-30f)

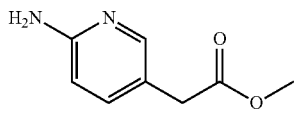

(I-30f)

To a solution of intermediate (I-30e) (11.0 g, 72.36 mmol) in dry methanol (80 mL) was added conc. $H_2SO_4$ (1.6 mL) and heated to reflux overnight. LC-MS indicated the reaction was complete. The reaction mixture was basified to pH 8.0 with sat. aq. sodium bicarbonate and extracted with ethyl acetate (30 mL×3). The combined organic layer was dried and concentrated in vacuo to give a crude product, which was purified by prep. HPLC to afford (I-30f) (2.2 g, yield: 18%) as a white solid; $^1$H NMR (400 MHz, $CD_3OD$): δ 7.78-7.82 (1 H), 7.40-7.50 (1 H), 6.59-6.62 (1 H), 3.69-3.78 (3 H), 3.50-3.60 (2 H); m/z 167.3 $(M+H)^+$.

Intermediate: (S)-methyl 2-(6-(3-cyclopentyl-2-(4-(trifluoromethyl)-1H-imidazol-1-yl)propanamido)pyridin-3-yl)acetate (I-30g)

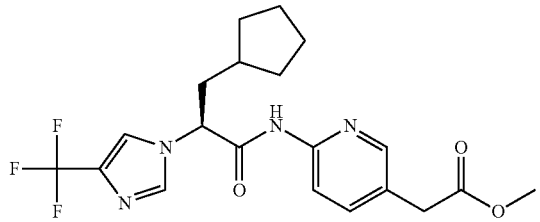

(I-30g)

To a solution of intermediate (I-8c) (0.33 g, 1.12 mmol) in dichloromethane (20 mL) was added intermediate (I-30f) (0.223 g, 0.9 mmol) and triethylamine (0.48 mL, 3.36 mmol) at room temperature, and the mixture was stirred for 12 hours at room temperature under nitrogen. TLC (petroleum ether/ethyl acetate=1:1) indicated the reaction was complete. The reaction mixture was concentrated in vacuo and the residue was purified by chromatography on silica to afford (I-30h) (220 mg, 46.4%) as an oil; $^1$H NMR (400 MHz, $CD_3OD$): δ 8.29 (1 H), 8.12 (1 H), 8.00 (1 H), 7.77 (1 H), 7.45 (1 H), 5.21 (1 H), 3.74 (5 H), 2.25 (2 H), 1.80 (1 H), 1.70 (1 H), 1.68 (3 H), 1.58 (2 H), 1.35 (1 H), 1.22 (1 H).

Intermediate: 2-methyl-2-(1-oxy-pyridin-3-yl)-propionic acid ethyl ester (I-31a)

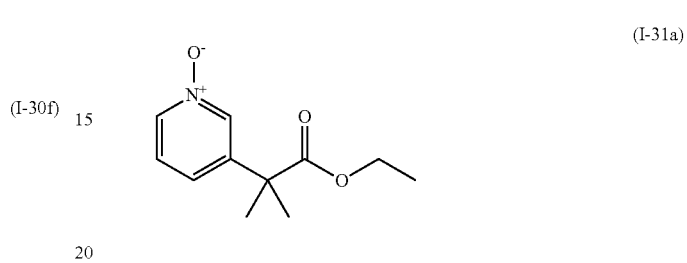

(I-31a)

To a solution of intermediate (I-30c) (15.2 g, 0.084 mol) in THF (250 mL) was added potassium t-butoxide (18.81 g, 0.168 mmol) slowly at −20° C. and stirred for 30 minutes. Methyl iodide (23.86 g, 0.168 mol) was added dropwise so as to maintain the internal temperature between −20° C. to −15° C. Then the mixture was stirred at 0° C. for 12 h. LC-MS indicated the reaction was complete. The reaction mixture was poured into ice water (150 mL) and ethyl acetate (150 mL). The organic layer was separated and the aqueous phase was extracted with ethyl acetate (100 mL×2). The combined organic layer was dried over $Na_2SO_4$ and concentrated under reduced pressure to give a crude product, which was purified by prep. HPLC to afford (I-31a) (4.0 g, yield: 23%) as an oil; $^1$H NMR (400 MHz, $CD_3OD$): δ 8.40-8.47 (1 H), 8.30-8.37 (1 H), 7.70-7.80 (1 H), 7.52-7.61 (1 H), 4.08-4.15 (2 H), 1.52-1.63 (6 H), 1.12-1.20 (3 H).

Intermediate: ethyl 2-(6-(2,2-dimethyl-4-oxo-2H-benzo[e][1,3]oxazin-3(4 H)-yl)pyridin-3-yl)-2-methylpropanoate (I-31b)

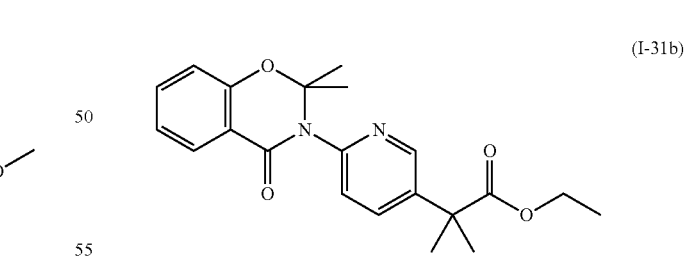

(I-31b)

A solution of intermediate (I-31a) (4.0 g, 0.019 mol) and intermediate (I-30b) (3.135 g, 0.016 mol) in 1,2-dichloroethane (50 mL) was heated to reflux for 3 days. TLC (dichloromethane: methanol=15:1) indicated the reaction was complete. The solvent was removed under reduced pressure to give a crude product, which was purified by flash chromatography (dichloromethane: methanol=80:1→60:1→30:1→20:1) to afford impure (I-31b) (3.68 g, 48.5% purity by LC-MS) as a solid. Intermediate: 2-(6-aminopyridin-3-yl)-2-methylpropanoic acid hydrochloride (I-31c)

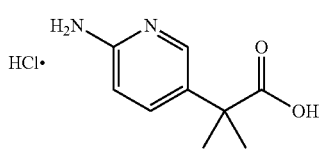

(I-31c)

A solution of intermediate (I-31b) (3.68 g, 0.01 mol) in conc. HCl (30 mL) was refluxed overnight. The solvent was removed under reduced pressure. The residue was dried by lyophilization to afford (I-31c) (3.4 g) as a solid, which was put into next step without any purification.

Intermediate: methyl 2-(6-aminopyridin-3-yl)-2-methylpropanoate (I-31 d)

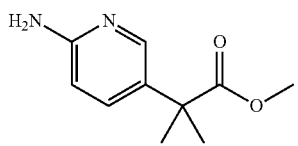

(I-31d)

To a solution of intermediate (I-31c) (3.4 g, 0.019 mmol) in dry methanol (25 mL) was added conc. $H_2SO_4$ (0.5 mL) and heated to reflux overnight. LC-MS indicated the reaction was complete. The reaction mixture was basified to pH 8.0 with sat. aq. sodium bicarbonate and extracted with ethyl acetate (30 mL×3). The combined organic layer was dried over $Na_2SO_4$ and concentrated in vacuo to give a crude product, which was purified by prep. HPLC to afford (I-31d) (0.5 g, yield: 14%) as a white solid; $^1$H NMR (400 MHz, $CD_3OD$): δ 7.80-7.90 (1 H), 7.46-7.51 (1 H), 6.53-6.60 (1 H), 3.60-3.70 (3 H), 1.48-1.60 (6 H); m/z 195.3 $(M+H)^+$.

Intermediate: (S)-methyl 2-(6-(3-cyclopentyl-2-(4-(trifluoromethyl)-1H-imidazol-1-yl)propanamido)pyridin-3-yl)-2-methylpropanoate (I-31e)

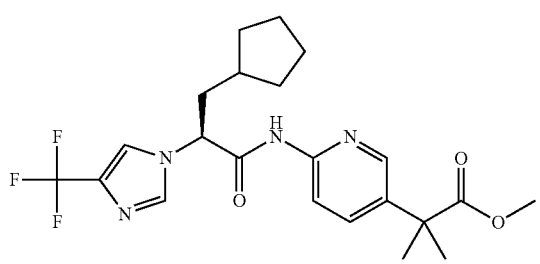

(I-31e)

To a solution of intermediate (I-8c) (0.26 g, 0.88 mmol) in dichloromethane (10 mL) was added intermediate (I-31d) (0.171 g, 0.88 mmol) and triethylamine (0.38 mL, 2.64 mmol) at room temperature, and the mixture was stirred for 12 hours at room temperature under nitrogen. TLC (petroleum ether/ethyl acetate=1:1) indicated the reaction was complete. The reaction mixture was concentrated in vacuo, the residue was purified by chromatography on silica to afford (I-31 e) (240 mg, 60.2%) as a light yellow solid; $^1$H NMR (400 MHz, $CD_3OD$): δ 8.37 (1 H), 8.12 (1 H), 8.05 (1 H), 7.88 (1 H), 7.84 (1 H), 5.18 (1 H), 3.72 (3 H), 2.22 (2 H), 1.85 (1 H), 1.80 (1 H), 1.72 (3 H), 1.67 (6 H), 1.61 (2 H), 1.38 (1 H), 1.28 (1 H).

Intermediate: (S)-3-cyclopentyl-N-(5-nitropyridin-2-yl)-2-(4-(trifluoromethyl)-1H-imidazol-1-yl)propanamide (I-32a)

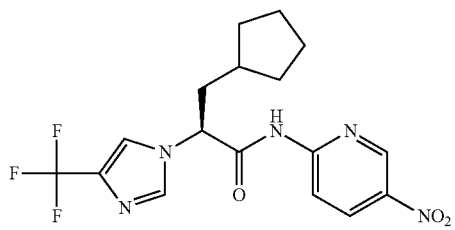

(I-32a)

To a solution of intermediate (I-8c) (2.13 g, 7.2 mmol) in dichloromethane (40 mL) was added 2-amino-5-nitropyridine (1.0 g, 7.2 mmol; Aldrich Chemical Company, Inc., Milwaukee, Wis.) and triethylamine (3.12 mL, 21.6 mmol) at room temperature, and the mixture was stirred for 12 hours at room temperature under nitrogen. TLC (petroleum ether/ethyl acetate=1:1) indicated the reaction was complete. The reaction mixture was concentrated in vacuo, the residue was purified by chromatography on silica to afford (I-32a) (1.1 g, 38.7%) as a light yellow solid.

Intermediate: (S)—N-(5-aminopyridin-2-yl)-3-cyclopentyl-2-(4-(trifluoromethyl)-1H-imidazol-1-yl)propanamide (I-32b)

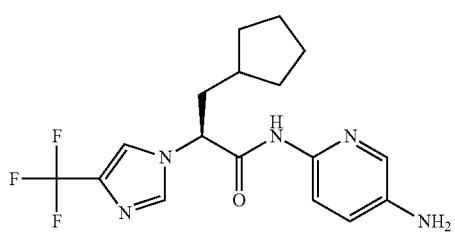

(I-32b)

To a solution of intermediate (I-32a) (0.62 mg, 1.56 mmol) in N,N-dimethylformamide (20 mL) was added zinc (1.02 g, 15.6 mmol) and a solution of $FeCl_3$ (2.53 mg, 15.6 mmol) in water (20 mL) at room temperature. The mixture was heated at 100° C. for 3 hours under nitrogen. TLC (petroleum ether/ethyl acetate=1:1) indicated the reaction was complete. The reaction mixture was filtered, and the filtrate was concentrated in vacuo. The residue was washed with water (20 mL) and the mixture was extracted with ethyl acetate (20 mL×3). The combined organic layers were washed with brine, dried over Na$_2$SO$_4$, and evaporated in vacuo to afford crude (I-32b) (0.58 g, 101.2%) as a light yellow solid, which was used in the next step directly.

Intermediate: (S)-ethyl 2-(6-(3-cyclopentyl-2-(4-(trifluoromethyl)-1H-imidazol-1-yl)propanamido) pyridin-3-ylamino)-2-oxoacetate (I-32c)

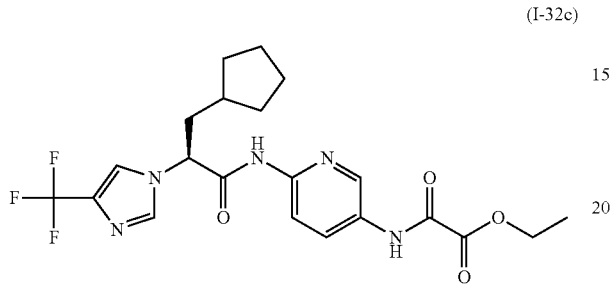

(I-32c)

To a solution of intermediate (I-32b) (crude 0.35 g, 0.95 mmol) in dichloromethane (20 mL) was added ethyl chlorooxoacetate (130 mg, 0.95 mmol; Aldrich Chemical Company, Inc., Milwaukee, Wis.) and triethylamine (0.41 mL, 2.85 mmol) at room temperature, and the mixture was stirred for 12 hours at room temperature under nitrogen. TLC (petroleum ether/ethyl acetate=1:1) indicated the reaction was complete. The reaction mixture was concentrated in vacuo, the residue was purified by chromatography on silica to afford impure (I-32c) (130 mg, 29.2%) as an oil; $^1$H NMR (400 MHz, CDCl$_3$): δ 8.83 (1 H), 8.52 (1 H), 8.20 (2 H), 8.02 (1 H), 7.63 (1 H), 7.45 (1 H), 4.69 (1 H), 4.40 (2 H), 2.15 (2 H), 1.40-1.65 (7 H), 1.35 (3 H), 1.14 (2 H).

Intermediate: (S)-1-(6-(3-cyclopentyl-2-(4-(trifluoromethyl)-1H-imidazol-1-yl)propanamido)pyridin-3-ylamino)-2-methyl-1-oxopropan-2-yl acetate (I-33a)

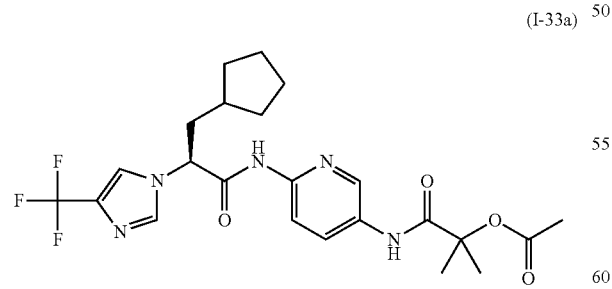

(I-33a)

To a solution of intermediate (I-32b) (crude 1.0 g, 2.72 mmol) in dichloromethane (20 mL) was added 1-chlorocarbonyl-1-methylethyl acetate (448 mg, 2.72 mmol; Aldrich Chemical Company, Inc., Milwaukee, Wis.) and triethylamine (1.17 mL, 8.16 mmol) at room temperature, and the mixture was stirred for 12 hours at room temperature under nitrogen. TLC (petroleum ether/ethyl acetate=1:1) indicated the reaction was complete. The reaction mixture was concentrated in vacuo and the residue was purified by chromatography on silica to afford (I-33a) (350 mg, 26.1%) as an oil; $^1$H NMR (400 MHz, CD$_3$OD): δ 8.51 (1 H), 8.09 (1 H), 7.95 (2 H), 7.86 (1 H), 5.13 (1 H), 2.20 (2 H), 2.10 (3 H), 1.82 (1 H), 1.75 (1 H), 1.52-1.74 (11 H), 1.37 (1 H), 1.18 (1 H).

Intermediate: (S)-3-cyclopentyl-2-(4-(ethylsulfonyl)-1H-imidazol-1-yl)propanoic acid (I-34a)

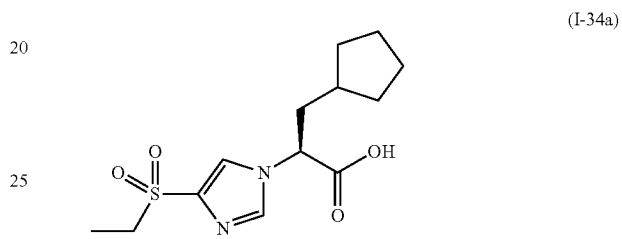

(I-34a)

To a solution of intermediate (I-7a2) (0.63 g, 2.0 mmol) in THF (6.3 mL) and water (6.3 mL) was added lithium hydroxide monohydrate (0.252 g, 6.01 mmol) portionwise at room temperature. After the addition, the mixture was stirred for 2 hours at room temperature. TLC (petroleum ether/ethyl acetate=1:1) indicated the reaction was complete. The reaction mixture was acidified with 0.5 N aq. HCl and the mixture was extracted with ethyl acetate (20 mL×3). The combined organic layers were washed with brine, dried over Na$_2$SO$_4$, and evaporated in vacuo to afford crude (I-34a) (0.55 g, 91.7%) as an oil, which was used in the next step directly.

Intermediate: (S)-3-cyclopentyl-2-(4-(ethylsulfonyl)-1H-imidazol-1-yl)propanoyl chloride (I-34b)

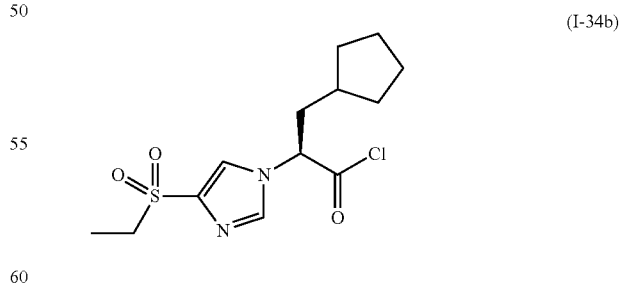

(I-34b)

To a solution of intermediate (I-34a) (0.35 g, 1.17 mmol) in dichloromethane (10 mL) was added oxalyl chloride (0.443 g, 3.49 mmol) and N,N-dimethylformamide (1 drop) at room temperature. The mixture was stirred for 2 hours at room temperature. TLC (petroleum ether/ethyl acetate=1:1) indicated the reaction was complete. The reaction mixture was concentrated in vacuo. The residue was chased with dichloromethane two times and concentrated in vacuo to afford crude (I-34b) (0.35 g, 94.33%) as an oil, which was used in the next step directly.

Intermediate: (S)-benzyl 6-(3-cyclopentyl-2-(4-(ethylsulfonyl)-1H-imidazol-1-yl)propanamido)nicotinate (I-34c1)

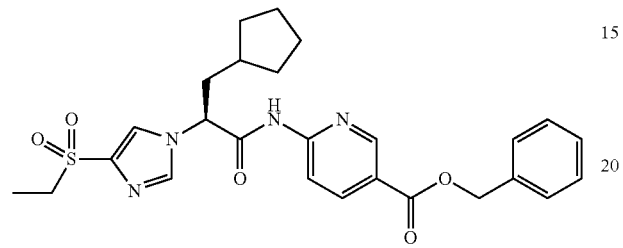

To a solution of intermediate (I-34b) (0.35 g, 1.09 mmol) in dichloromethane (10 mL) was added intermediate (I-28a) (0.25 g, 1.09 mmol) and triethylamine (0.47 mL, 3.29 mmol) at room temperature, and the mixture was stirred for 12 hours at room temperature under nitrogen. TLC (petroleum ether/ethyl acetate=1:1) indicated the reaction was not complete. The reaction mixture was concentrated in vacuo, diluted with 0.5 N aq. HCl (10 mL), and extracted with ethyl acetate (20 mL×3). The combined organic layers were washed with brine, dried over $Na_2SO_4$, and evaporated in vacuo. The residue was purified by chromatography on silica to afford (I-34c1) (100 mg, 17.82%) as an oil.

Intermediates (S)-benzyl 6-(3-cyclopentyl-2-(4-(isopropylsulfonyl)-1H-imidazol-1-yl)propanamido)nicotinate (I-34c2) and (S)-benzyl 6-(2-(4-(cyclobutylsulfonyl)-1H-imidazol-1-yl)-3-cyclopentylpropanamido)nicotinate (I-34c3) were prepared in an analogous manner to that described for the synthesis of Intermediate I-34c1, above, using appropriate starting materials (e.g., I-7a1 or I-34e, respectively).

Intermediate: cyclobutanethiol (I-34d)

To a solution of magnesium (0.87 g, 36.2 mmol) in THF (20 mL) was added cyclobutyl bromide (5.0 g, 37 mmol; Aldrich Chemical Company, Inc., Milwaukee, Wis.) dropwise at 50° C. After the addition, the mixture was refluxed for 2 hours, at which point the magnesium appeared completely consumed. The mixture was cooled to 0° C., sulfur (0.95 g, 29.6 mmol) was added portionwise to the mixture, and the resulting mixture was stirred at 50° C. for 2 hours. The mixture was cooled to 0° C. and lithium aluminum hydride (0.76 g, 19.95 mmol) was added portionwise to the mixture. The resulting mixture was refluxed for 30 mins. The mixture was quenched with aq. ammonium chloride (20 mL), 1 N HCl (20 mL) was added, and extracted with diethyl ether (20 mL×3). The combined organic layers were washed with brine, dried over $Na_2SO_4$, and filtered to give a crude solution of intermediate (I-34d) in THF and diethyl ether, which was used in the next step directly.

Intermediate: 1,2-dicyclobutyldisulfane (I-34e)

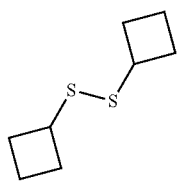

To a crude solution of intermediate (I-34d) in THF and diethyl ether was added a solution of sodium (0.562 g, 0.024 mol) in ethanol dropwise, followed by iodine ($I_2$, 5.6 g, 0.022 mol). After the addition, the mixture was stirred for 1 hour at room temperature. TLC (petroleum ether/ethyl acetate=5:1) indicated the reaction was complete. The mixture was quenched with aq. $NaHSO_3$ (50 mL) and extracted with diethyl ether (20 mL×3). The combined organic layers were washed with brine, dried over $Na_2SO_4$, and evaporated in vacuo. The residue was purified by chromatography on silica to afford (I-34e) (2.1 g, 32.6%) as an oil; $^1H$ NMR (400 MHz, $CDCl_3$): δ 3.48 (2 H), 2.21 (4 H), 2.08 (4 H), 1.85 (4 H).

Intermediate: N,N-dimethyl-1H-imidazole-4-sulfonamide (I-35a)

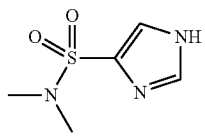

To a solution of 1H-imidazole-4-sulfonyl chloride (0.5 g, 3.0 mmol; Matrix Scientific, Columbia, S.C.) in dichloromethane (10 mL) was added dimethylamine hydrochloride (0.245 g, 3.0 mmol) and triethylamine (1.3 mL, 9.0 mmol) at room temperature. The mixture was stirred for 16 hours at room temperature. TLC (petroleum ether/ethyl acetate=0:1) indicated the reaction was complete. The reaction mixture was washed with aq. ammonium chloride (30 mL) and extracted with dichloromethane: methanol=4:1 (3×50 mL). The combined organic phases were concentrated and precipitated from methanol to afford (I-35a) (0.36 g, 68.2%) as a white solid; $^1$H NMR (400 MHz, CD$_3$OD): δ 7.74 (1 H), 7.61 (1 H), 2.68 (6 H).

Intermediate: (S)-3-cyclopentyl-2-(4-dimethylsulfamoyl-imidazol-1-yl)-propionic acid methyl ester (I-35b)

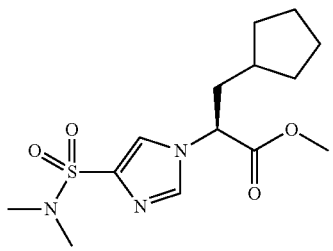

(I-35b)

To a solution of intermediate (I-35a) (0.36 g, 2.045 mmol) in THF (10 mL) was added lithium hexamethyldisilazide (1.84 mL, 1.84 mmol) dropwise at room temperature. After the addition, the mixture was stirred for 1 hour at room temperature and intermediate (I-1c) (0.622 g, 2.045 mmol) was added. The resulting mixture was stirred at room temperature for 12 hours. TLC (petroleum ether/ethyl acetate=1:1) indicated the reaction was complete. The mixture was quenched with aq. ammonium chloride (30 mL) and the residue was extracted with ethyl acetate (20 mL×3). The combined organic layers were washed with brine, dried over Na$_2$SO$_4$, and evaporated in vacuo. The residue was purified by chromatography on silica to afford (I-35b) (580 mg, 86.4%) as an oil; $^1$H NMR (400 MHz, CD$_3$OD): δ 87.96 (1 H), 7.90 (1 H), 5.17 (1 H), 3.78 (3 H), 2.76 (6 H), 2.20 (2 H), 1.72 (1 H), 1.68 (3 H), 1.55 (3 H), 1.23 (1 H), 1.10 (1 H).

Intermediate: (S)-3-cyclopentyl-2-(4-dimethylsulfamoyl-imidazol-1-yl)-propionic acid (I-35c)

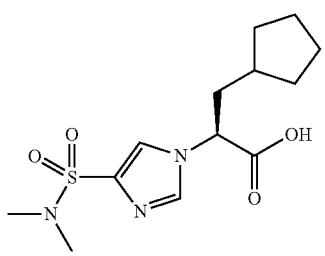

(I-35c)

To a solution of intermediate (I-35b) (0.35 g, 1.06 mmol) in THF (3.5 mL) and water (3.5 mL) was added lithium hydroxide monohydrate (133 mg, 3.18 mmol) portionwise at room temperature. After the addition, the mixture was stirred for 2 hours at room temperature. TLC (petroleum ether/ethyl acetate=1:1) indicated the reaction was complete. The reaction mixture was acidified with 0.5 N aq. HCl and the mixture was extracted with ethyl acetate (20 mL×3). The combined organic layers were washed with brine, dried over Na$_2$SO$_4$, and evaporated in vacuo to afford crude (I-35c) (0.32 g, 95.5%) as a light yellow solid.

Intermediate: (S)-3-cyclopentyl-2-(4-dimethylsulfamoyl-imidazol-1-yl)-propionyl chloride (I-35d)

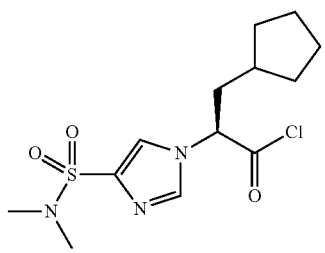

(I-35d)

To a solution of intermediate (I-35c) (0.33 g, 1.04 mmol) in dichloromethane (10 mL) was added oxalyl chloride (0.397 g, 3.13 mmol) and N,N-dimethylformamide (1 drop) at room temperature. The mixture was stirred for 2 hours at room temperature. TLC (petroleum ether/ethyl acetate=1:1) indicated the reaction was complete. The reaction mixture was concentrated in vacuo, the residue was chased with dichloromethane two times, and concentrated in vacuo to afford crude (I-35d) (0.35 g, 100%) as an oil, which was used in the next step directly.

Intermediate: 6-[(S)-3-cyclopentyl-2-(4-dimethylsulfamoyl-imidazol-1-yl)-propionylamino]-nicotinic acid benzyl ester (I-35e)

(I-35e)

To a solution of intermediate (I-35d) (0.35 g, 1.09 mmol) in dichloromethane (15 mL) was added intermediate (I-28a) (0.24 g, 1.04 mmol) and pyridine (0.25 mL, 3.13 mmol) at room temperature, and the mixture was stirred for 12 hours at room temperature under nitrogen. TLC (petroleum ether/ethyl acetate=1:1) indicated the reaction was not complete. The reaction mixture was concentrated in vacuo, 0.5 N aq. HCl (10 mL) was added, and extracted with ethyl acetate (20 mL×3). The combined organic layers were washed with brine, dried over Na$_2$SO$_4$, and evaporated in vacuo. The residue was purified by chromatography on silica to afford (I-35e) (80 mg, 14.6%) as an oil.

Intermediate: methyl 2-(4-(trifluoromethyl)-1H-imidazol-1-yl)acetate (I-36a)

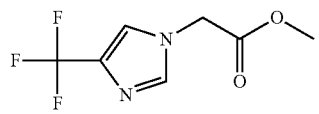

(I-36a)

To a solution of 4-(trifluoromethyl)-1H-imidazole (10.0 g, 73.5 mmol) in THF (75 mL) at 0° C. was added sodium hydride (60% in mineral oil, 3.25 g, 80.8 mmol) under nitrogen. The mixture was stirred at 0° C. for 30 min. Methyl bromoacetate (1.67 mL, 17.6 mmol) was added and the reaction was stirred for 3 h at room temperature. LC-MS showed the reaction was complete. The solvent was removed under reduced pressure. The crude material was redissolved in diethyl ether and washed with sat. aq. ammonium chloride and 1N HCl aqueous solution. The combined aqueous layer was reextracted with ethyl acetate three times. The combined organic layer was dried over MgSO$_4$, filtered, and evaporated to a mixture of solid and oil. The crude was filtered to remove most of the oil, and the solid was washed with heptane. This yellow solid was triturated in a minimum amount of diethyl ether to wash off the yellow impurities. The material was filtered and the solid was retriturated with diethyl ether again. The filtrate was concentrated and the previous trituration steps were repeated. This afforded (I-36a) as a white solid (9.33 g, 61%); $^1$H NMR (400 MHz, CDCl$_3$): δ 7.53 (1 H), 7.30 (1 H), 4.73 (2 H), 3.81 (3 H); m/z 209.0 (M+H)$^+$.

Intermediate: methyl 3-(1-methyl-1H-imidazol-4-yl)-2-(4-(trifluoromethyl)-1H-imidazol-1-yl)acrylate (I-36b)

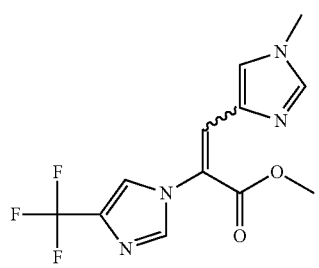

(I-36b)

To a 0.2 M solution of intermediate (I-36a) in THF was added 1.1 eq 1-methyl-1H-imidazole-4-carbaldehyde (Ryan Scientific, Inc., Mt. Pleasant, S.C.), and this solution was then cooled to 0° C. To this solution was added 0.5 equivalents of potassium t-butoxide as a 1 M solution in THF, and the reaction was allowed to slowly warm to RT. After 18 h the solution was acidified with 1N HCl, brine was added, and extracting three times with ethyl acetate. The resulting organic layers were then combined, dried over sodium sulfate and concentrated to afford crude (I-36b). This material was taken forward crude.

Intermediate: methyl 3-(1-methyl-1H-imidazol-4-yl)-2-(4-(trifluoromethyl)-1H-imidazol-1-yl)propanoate (I-36c1)

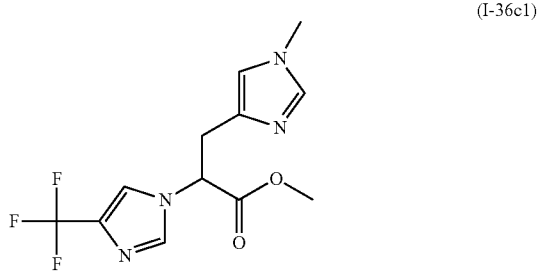 [SMILES: COC(=O)C(Cc1cn(C)cn1)n1cnc(C(F)(F)F)c1]

(I-36c1)

Crude intermediate (I-36b) was dissolved in THF. To this solution was then added 30 equivalents of water, 10 equivalents of ammonium formate, and finally 0.1 equivalent of palladium on carbon (10%). This mixture was then heated to reflux. After 60 min the reaction was worked-up by filtering through a syringe filter, washing with ethanol, drying over magnesium sulfate, and concentrating down to afford crude (I-36c1) which was used in the next step without purification.

Intermediates methyl 3-(4-ethylthiazol-2-yl)-2-(4-(trifluoromethyl)-1H-imidazol-1-yl)propanoate, (I-36c2), and methyl 3-(1-methyl-1H-pyrazol-3-yl)-2-(4-(trifluoromethyl)-1H-imidazol-1-yl)propanoate (I-36c3) were prepared in an analogous manner to that described for the synthesis of Intermediate (I-36c1) from 4-ethylthiazole-2-carbaldehyde (Aces Pharma, Inc., Branford, Conn.) and 1-methyl-1H-pyrazole-3-carbaldehyde (Ryan Scientific, Inc., Mt. Pleasant, S.C.), respectively.

EXAMPLES

The compounds provided below may be prepared using procedures as described herein using appropriate starting materials which are commercially available, prepared using preparations well-known to the skilled artisan, or prepared in a manner analogous to routes described herein.

Examples I-24 of general Formula (1A-1) are provided below.

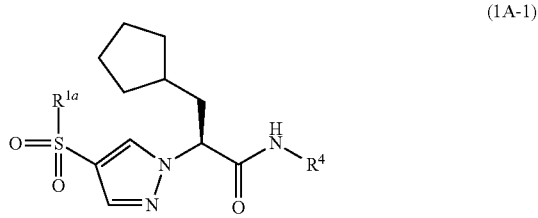

(1A-1)

Example 1

(S)-3-cyclopentyl-2-(4-(isopropylsulfonyl)-1H-pyrazol-1-yl)-N-(5-methylpyridin-2-yl)propanamide Formula (1A-1) wherein $R^{1a}$ is isopropyl and $R^4$ is

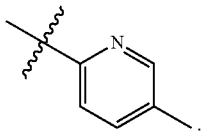 [SMILES: *c1ccc(C)cn1]

To a stirred solution of 2-amino-5-picoline (57 mg, 0.531 mmol) in anhydrous toluene was added $AlMe_3$ (2.0 M in toluene, 0.284 mL, 0.567 mmol). The mixture was stirred at room temperature for 35 minutes, and then a solution of Intermediate (I-4a1) (83 mg, 0.25 mmol) in dichloroethane (2 mL) was added. The reaction mixture was heated at 80° C. for 48 hours and then cooled to room temperature and saturated aqueous potassium sodium tartrate tetrahydrate was added. The mixture was extracted with $CH_2Cl_2$. The combined extracts were dried over $MgSO_4$ and eluted with flash column chromatography ($SiO_2$, 0-100% ethyl acetate/heptane) to afford the title compound. $^1H$ NMR (400 MHz, $d_6$-DMSO) δ 10.94 (1H), 8.52 (1H), 8.15 (1H), 7.85-7.89 (2H), 7.57-7.60 (1H), 5.33-5.37 (1H), 3.23-3.28 (1H), 2.22-2.29 (4H), 2.01-2.08 (1H), 1.43-1.65 (5H), 1.32-1.43 (2H), 1.20-1.29 (1H), 1.13-1.16 (6H), 1.02-1.10 (1H); m/z 405.0 $(M+H)^+$, 403.1 $(M-H)^-$.

Example 2

(S)-3-cyclopentyl-2-(4-(isopropylsulfonyl)-1H-pyrazol-1-yl)-N-(pyrazin-2-yl)propanamide Formula (1A-1) wherein $R^{1a}$ is isopropyl and $R^4$ is

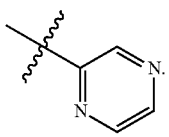 [SMILES: *c1cnccn1]

Example 2 was synthesized in an analogous manner to that of Example 1 from Intermediate I-4a1 and 2-aminopyrazine. $^1H$ NMR (400 MHz, $CDCl_3$) δ 9.48 (1 H), 9.37 (1 H), 8.38 (1 H), 8.27 (1 H), 8.09 (1 H), 7.98 (1 H), 5.03 (1 H), 4.11 (1 H), 3.14 (1 H), 2.20-2.39 (2 H), 2.04 (2 H), 1.45-1.69 (4 H), 1.33 (6H), 1.25 (2 H); m/z 392.2 $(M+H)^+$.

Example 3

(S)-3-cyclopentyl-2-(4-(isopropylsulfonyl)-1H-pyrazol-1-yl)-N-(5-(trifluoromethyl)pyridin-2-yl)propanamide Formula (1A-1) wherein $R^{1a}$ is isopropyl and $R^4$ is

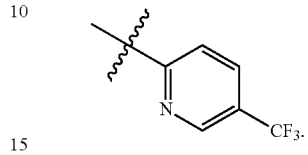

Example 3 was synthesized in an analogous manner to that of Example 1 from Intermediate I-4a1 and 2-amino-5-trifluoromethylpyridine. $^1H$ NMR (400 MHz, $CDCl_3$) δ 9.40 (1 H), 8.56 (1H), 8.30 (1H), 8.03 (2 H), 7.94 (1 H), 4.98 (1 H), 3.20 (1 H), 2.32-2.42 (1 H), 2.19-2.29 (1 H), 1.72-1.85 (1 H), 1.48-1.71 (4H), 1.30-1.38 (6 H), 1.17-1.30 (2 H), 1.04-1.16 (2 H); m/z 459.1 $(M+H)^+$.

Example 4

(S)-3-cyclopentyl-2-(4-(isopropylsulfonyl)-1H-pyrazol-1-yl)-N-(pyrimidin-4-yl)propanamide Formula (1A-1) wherein $R^{1a}$ is isopropyl and $R^4$ is

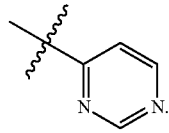 [SMILES: *c1ccncn1]

Example 4 was synthesized in an analogous manner to that of Example 1 from Intermediate I-4a1 and 4-aminopyrimidine. $^1H$ NMR (400 MHz, $CDCl_3$) δ 9.39 (1 H), 8.88 (1 H), 8.65 (1 H), 8.10 (1 H), 8.01 (1 H), 7.98 (1 H), 4.95 (1 H), 3.20 (1 H), 2.37 (1 H), 2.20 (1 H), 1.76 (1H), 1.58-170 (6H), 1.36 (6H), 1.18 (1 H), 1.02 (1 H); m/z 392.1 $(M+H)^+$.

Example 5

(S)-3-cyclopentyl-2-(4-(isopropylsulfonyl)-1H-pyrazol-1-yl)-N-(pyrimidin-2-yl)propanamide Formula (1A-1) wherein $R^{1a}$ is isopropyl and $R^4$ is

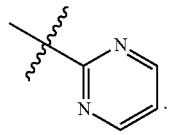

Example 5 was synthesized in an analogous manner to that of Example 1 from Intermediate I-4a1 and 2-aminopyrimidine. $^1H$ NMR (400 MHz, $CDCl_3$) δ 9.91 (1 H), 8.67 (1 H), 8.66 (1 H), 8.18 (1 H), 7.86 (1 H), 7.08 (1 H), 3.20 (1 H), 2.22 (2 H), 1.81 (1H), 1.58-166 (6H), 1.30-132 (6H), 1.23 (2 H), 1.02 (1 H); m/z 392.2 $(M+H)^+$.

Example 6

(S)-3-cyclopentyl-2-(4-(isopropylsulfonyl)-1H-pyrazol-1-yl)-N-(5-methylpyrazin-2-yl)propanamide Formula (1A-1) wherein $R^{1a}$ is isopropyl and $R^4$ is

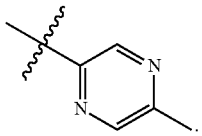 [SMILES: *c1cnc(C)cn1]

Example 6 was synthesized in an analogous manner to that of Example 1 from Intermediate I-4a1 and 2-amino-5-methylpyridine. $^1$H NMR (400 MHz, CDCl$_3$) δ 9.30 (1 H), 9.20 (1 H), 8.09 (1 H), 8.06 (1 H), 7.94 (1 H), 5.02 (1 H), 3.14-3.19 (1 H), 2.49 (3 H), 2.21-2.35 (2 H), 1.76 (1H), 1.44-1.60 (6H), 1.29-131 (6H), 1.16-1.20 (1H), 1.08-1.14 (1 H); m/z 406.2 (M+H)$^+$.

Example 7

(S)-3-cyclopentyl-2-(4-(isopropylsulfonyl)-1H-pyrazol-1-yl)-N-(1-methyl-1H-pyrazol-3-yl)propanamide Formula (1A-1) wherein $R^{1a}$ is isopropyl and $R^4$ is

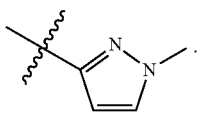 [SMILES: *c1ccn(C)n1]

Example 7 was synthesized in an analogous manner to that of Example 1 from Intermediate I-4a1 and 3-amino-1-methylpyrazole. $^1$H NMR (400 MHz, d$_6$-DMSO) δ 10.96 (1H), 8.48 (1H), 7.83 (1H), 7.53 (1H), 6.37 (1H), 5.20-5.23 (1H), 3.71 (3H), 3.22-3.28 (1H), 2.16-2.23 (1H), 1.99-2.06 (1H), 1.44-1.64 (5H), 1.36-1.44 (2H), 1.20-1.26 (1H), 1.13-1.16 (6H), 0.99-1.10 (1H); m/z 394.0 (M+H)$^+$, 392.1 (M−H)$^−$.

Example 8

(S)-3-cyclopentyl-N-(5-methylpyridin-2-yl)-2-(4-(methylsulfonyl)-1H-pyrazol-1-yl)propanamide Formula (1A-1) wherein $R^{1a}$ is methyl and $R^4$ is

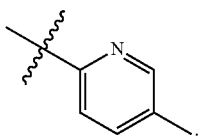 [SMILES: *c1ccc(C)cn1]

Example 8 was synthesized in an analogous manner to that of Example 1 from Intermediate I-4a2 and 2-amino-5-methylpyridine. $^1$H NMR (400 MHz, d$_6$-DMSO) δ 10.97 (1H), 8.55 (1H), 8.16 (1H), 7.88-7.91 (2H), 7.57-7.60 (1H), 5.34-5.36 (1H), 3.20 (3H), 2.11-2.24 (4H), 2.01-2.08 (1H), 1.58-1.64 (2H), 1.44-1.58 (3H), 1.36-1.44 (2H), 1.20-1.30 (1H), 1.04-1.11 (1H); m/z 376.9 (M+H)$^+$, 375.1 (M−H)$^−$.

Example 9

(S)-3-cyclopentyl-N-(1-methyl-1H-pyrazol-3-yl)-2-(4-(methylsulfonyl)-1H-pyrazol-1-yl)propanamide Formula (1A-1) wherein $R^{1a}$ is methyl and $R^4$ is

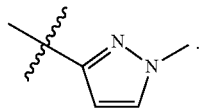 [SMILES: *c1ccn(C)n1]

Example 9 was synthesized in an analogous manner to that of Example 1 from Intermediate I-4a2 and 3-amino-1-methylpyrazole. $^1$H NMR (400 MHz, d$_6$-DMSO) δ 10.98 (1H), 8.51 (1H), 7.90 (1H), 7.53 (1H), 6.38 (1H), 5.18-5.22 (1H), 3.71 (3H), 3.19 (3H), 2.11-2.19 (1H), 1.99-2.06 (1H), 1.60-1.68 (2H), 1.45-1.60 (3H), 1.17-1.45 (2H), 1.17-1.26 (1H), 1.03-1.10 (1H); m/z 366.0 (M+H)$^+$, 364.1 (M−H)$^−$.

Example 10

(S)-3-cyclopentyl-2-(4-(methylsulfonyl)-1H-pyrazol-1-yl)-N-(5-(trifluoromethyl)pyridin-2-yl)propanamide Formula (1A-1) wherein $R^{1a}$ is methyl and $R^4$ is

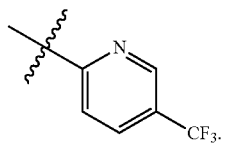

Example 10 was synthesized in an analogous manner to that of Example 1 from Intermediate I-4a2 and 2-amino-5-trifluoromethylpyridine. $^1$H NMR (400 MHz, CDCl$_3$) δ 9.31 (1H), 8.55 (1H), 8.24-8.28 (1H), 8.02-8.07 (2H), 7.90-7.97 (1H), 4.89-4.96 (1H), 3.17 (3H), 2.30-2.40 (1H), 2.18-2.28 (1H), 1.44-1.85 (7H), 1.15-1.28 (1H), 1.03-1.17 (1H); m/z 430.9 (M+H)$^+$, 429.0 (M−H)$^−$.

Example 11

(S)-3-cyclopentyl-N-(1-ethyl-1H-pyrazol-3-yl)-2-(4-(methylsulfonyl)-1H-pyrazol-1-yl)propanamide Formula (1A-1) wherein $R^{1a}$ is methyl and $R^4$ is

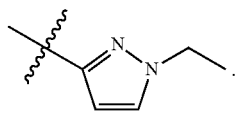

Example 11 was synthesized in an analogous manner to that of Example 1 from Intermediate I-4a2 and 3-amino-1-ethylpyrazole. $^1$H NMR (400 MHz, CDCl$_3$) δ 8.81 (1H), 8.06 (1H), 7.98 (1H), 7.29 (1H), 6.60 (1H), 5.84-4.88 (1H), 4.00-

4.08 (2H), 3.13 (3H), 2.18-2.35 (2H), 1.39-1.82 (10H), 1.01-1.24 (2H); m/z 380.0 (M+H)+, 378.1 (M–H)−.

Example 12

(S)—N-(1-benzyl-1H-pyrazol-3-yl)-3-cyclopentyl-2-(4-(methylsulfonyl)-1H-pyrazol-1-yl)propanamide Formula (1A-1) wherein $R^{1a}$ is methyl and $R^4$ is

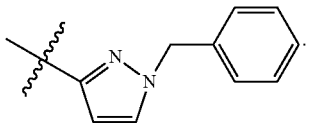

Example 12 was synthesized in an analogous manner to that of Example 1 from Intermediate I-4a2 and 3-amino-1-benzylpyrazole. $^1$H NMR (400 MHz, CDCl$_3$) δ 8.81 (1H), 8.03 (1H), 7.98 (1H), 7.28-7.36 (4H), 7.13-7.18 (1H), 6.64 (1H), 5.17 (2H), 4.83-4.88 (1H), 3.11 (3H), 2.18-2.31 (2H), 1.72-1.81 (1H), 1.42-1.71 (6H), 1.01-1.22 (2H); LCMS for C$_{22}$H$_{27}$N$_5$O$_3$S$_1$ m/z 442.0 (M+H)+, 440.0 (M–H)−.

Example 13

(S)-3-cyclopentyl-2-(4-(methylsulfonyl)-1H-pyrazol-1-yl)-N-(pyrimidin-4-yl)propanamide Formula (1A-1) wherein $R^{1a}$ is methyl and $R^4$ is

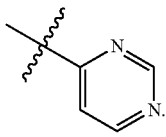 [SMILES: *c1ccncn1]

Example 13 was synthesized in an analogous manner to that of Example 1 from Intermediate I-4a2 and 4-aminopyrimidine. $^1$H NMR (400 MHz, CDCl$_3$) δ 9.25 (1H), 8.88 (1H), 8.62-8.65 (1H), 8.09-8.11 (1H), 8.03 (2H), 4.86-4.91 (1H), 3.15 (3H), 2.30-2.39 (1H), 2.17-2.24 (1H), 1.75-1.83 (1H), 1.44-1.74 (6H), 1.02-1.23 (2H); m/z 364.0 (M+H)+, 362.0 (M–H)−.

Example 14

(S)-3-cyclopentyl-N-(5-methylpyrazin-2-yl)-2-(4-(methylsulfonyl)-1H-pyrazol-1-yl)propanamide Formula (1A-1) wherein $R^{1a}$ is methyl and $R^4$ is

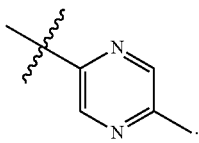 [SMILES: *c1cnc(C)cn1]

Example 14 was synthesized in an analogous manner to that of Example 1 from Intermediate I-4a2 and 2-amino-5-methylpyrazine. $^1$H NMR (400 MHz, CDCl$_3$) δ 9.35 (1H), 9.01 (1H), 8.12 (1H), 8.07 (1H), 8.02 (1H), 4.89-4.97 (1H), 3.12 (3H), 2.51 (3H), 2.28-2.40 (1H), 2.19-2.25 (1H), 1.75-1.82 (1H), 1.42-1.75 (6H), 1.16-1.24 (1H), 1.02-1.16 (1H); m/z 378.0 (M+H)+, 376.0 (M–H)−.

Example 15

(S)-3-cyclopentyl-2-(4-(isopropylsulfonyl)-1H-pyrazol-1-yl)-N-(isoxazol-3-yl)propanamide Formula (1A-1) wherein $R^{1a}$ is isopropyl and $R^4$ is

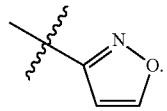

Example 15 was synthesized in an analogous manner to that of Example 1 from Intermediate I-4a1 and 3-aminoisoxazole. m/z 381 (M+H)+.

Example 16

(S)-3-cyclopentyl-2-(4-(isopropylsulfonyl)-1H-pyrazol-1-yl)-N-(pyridin-2-yl)propanamide Formula (1A-1) wherein $R^{1a}$ is isopropyl and $R^4$ is

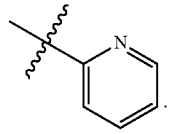

Example 16 was synthesized in an analogous manner to that of Example 1 from Intermediate I-4a1 and 2-aminopyridine. m/z 391 (M+H)+.

Example 17

(S)-3-cyclopentyl-2-(4-(isopropylsulfonyl)-1H-pyrazol-1-yl)-N-(quinolin-2-yl)propanamide Formula (1A-1) wherein $R^{1a}$ is isopropyl and $R^4$ is

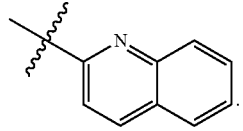 [SMILES: *c1ccc2ccccc2n1]

Example 17 was synthesized in an analogous manner to that of Example 1 from Intermediate I-4a1 and 2-aminoquinoline. m/z 441 (M+H)+.

Example 18

(S)-3-cyclopentyl-N-(1-ethyl-1H-pyrazol-3-yl)-2-(4-(isopropylsulfonyl)-1H-pyrazol-1-yl)propanamide Formula (1A-1) wherein $R^{1a}$ is isopropyl and $R^4$ is

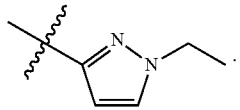

Example 18 was synthesized in an analogous manner to that of Example 1 from Intermediate I-4a1 and 3-amino-1-ethylpyrazole. $^1$H NMR (400 MHz, CDCl$_3$) δ 9.16 (1 H), 9.12 (1 H), 8.05 (1 H), 7.90 (1 H), 7.26 (1 H), 6.59 (1 H), 5.27 (1 H), 4.93-4.97 (1 H), 4.00-4.05 (2 H), 3.10-3.18 (1 H), 2.14-2.28 (2 H), 1.61-1.74 (1H), 1.38-1.55 (7H), 1.29-131 (6H), 1.12-1.17 (1H), 1.01-1.10 (1 H); m/z 408.2 (M+H)$^+$.

Example 19

(S)—N-(1-benzyl-1H-pyrazol-3-yl)-3-cyclopentyl-2-(4-(isopropylsulfonyl)-1H-pyrazol-1-yl)propanamide, Formula (1A-1) wherein $R^{1a}$ is isopropyl and $R^4$ is

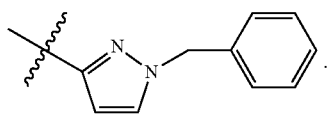 [SMILES: *c1ccn(Cc2ccccc2)n1]

Example 19 was synthesized in an analogous manner to that of Example 1 from Intermediate I-4a1 and 3-amino-1-benzylpyrazole. $^1$H NMR (400 MHz, CDCl$_3$) δ 9.00 (1 H), 8.00 (1 H), 7.90 (1 H), 7.28-7.79 (4 H), 7.14-7.16 (2 H), 6.67 (1 H), 5.28 (2 H), 4.88-4.92 (1 H), 3.11-3.18 (1 H), 2.02-2.30 (2 H), 1.67-1.76 (1H), 1.45-1.60 (6H), 1.30-132 (6H), 1.92-1247? (1H), 1.06-1.18 (1 H); m/z 470.3 (M+H)$^+$.

Example 20

(S)-3-cyclopentyl-2-(4-(ethylsulfonyl)-1H-pyrazol-1-yl)-N-(1-methyl-1H-pyrazol-3-yl)propanamide Formula (1A-1) wherein $R^{1a}$ is ethyl and $R^4$ is

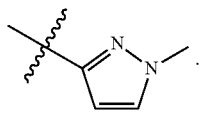

Example 20 was synthesized in an analogous manner to that of Example 1 from Intermediate I-4a3 and 3-amino-1-methylpyrazole. $^1$H NMR (400 MHz, CDCl$_3$) δ 9.37 (1 H), 8.11 (1 H), 7.90 (1 H), 7.22 (1 H), 6.59 (1 H), 4.95-4.99 (1 H), 3.77 (3 H), 3.09-3.14 (2 H), 2.16-2.23 (2 H), 1.40-1.75 (7 H), 1.20-1.31 (3 H), 0.98-1.12 (2 H); m/z 380.5 (M+H)$^+$.

Example 21

(S)-3-cyclopentyl-2-(4-(ethylsulfonyl)-1H-pyrazol-1-yl)-N-(5-methylpyridin-2-yl)propanamide Formula (1A-1) wherein $R^{1a}$ is ethyl and $R^4$ is

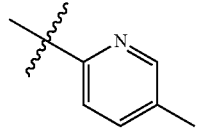

Example 21 was synthesized in an analogous manner to that of Example 1 from Intermediate I-4a3 and 2-amino-5-methylpyridine. $^1$H NMR (400 MHz, CDCl$_3$) δ 9.42 (1 H), 8.13 (2 H), 8.03 (1 H), 7.94 (1 H), 7.49 (1 H), 4.96-4.99 (1 H), 3.10-3.16 (2 H), 2.27 (3 H), 2.14-2.25 (1 H), 1.40-1.72 (8 H), 1.29-1.33 (3 H), 1.00-1.16 (2 H); m/z 391.5 (M+H)$^+$.

Example 22

(S)-3-cyclopentyl-2-(4-(ethylsulfonyl)-1H-pyrazol-1-yl)-N-(5-methylpyrazin-2-yl)propanamide Formula (1A-1) wherein $R^{1a}$ is ethyl and $R^4$ is

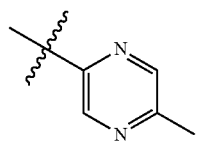

Example 22 was synthesized in an analogous manner to that of Example 1 from Intermediate I-4a3 and 2-amino-5-methylpyrazine. $^1$H NMR (400 MHz, CDCl$_3$) δ 9.31 (1 H), 9.21 (1 H), 8.08 (2 H), 7.97 (1 H), 4.97-5.00 (1 H), 3.11-3.17 (2 H), 2.50 (3 H), 2.24-2.32 (1 H), 1.44-1.77 (8 H), 1.28-1.32 (3 H), 1.07-1.21 (2 H); m/z 390.5 (M–H)$^+$.

Example 23

(S)-benzyl 6-(3-cyclopentyl-2-(4-(methylsulfonyl)-1H-pyrazol-1-yl)propanamido)nicotinate Formula (1A-1) wherein $R^{1a}$ is methyl and $R^4$ is

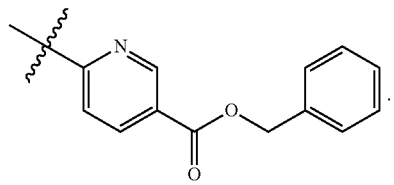 [SMILES: *c1ccc(C(=O)OCc2ccccc2)cn1]

Intermediate (I-23a) (165 mg, 0.576 mmol) was stirred in dry dichloromethane (6 mL) at room temperature under nitrogen. One drop of DMF was added followed by oxalyl chloride (0.10 mL, 1.15 mmol). After bubbling subsided, the reaction

Example 24

(S)-6-(3-cyclopentyl-2-(4-(methylsulfonyl)-1H-pyrazol-1-yl)propanamido)nicotinic acid Formula (1A-1) wherein $R^{1a}$ is methyl and $R^4$ is

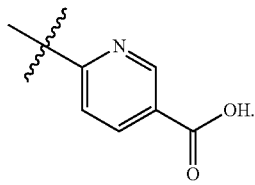 [SMILES: *c1ccc(C(=O)O)cn1]

The compound of Example 23 (182 mg, 0.367 mmol) was dissolved in ethyl acetate (3 mL) and ethanol (6 mL) in a 250 mL Parr bottle. 10% Palladium on carbon (20 mg) was added, and the mixture was shaken under 50 psi hydrogen for 90 minutes. The reaction was filtered, evaporated, and dried under high vacuum to afford the title compound (134.3 mg, 0.33 mmol, 90%). $^1$H NMR (400 MHz, DMSO-$d_6$) δ 11.44 (1 H), 8.83 (1 H), 8.57 (1 H), 8.23-8.26 (1 H), 8.09-8.11 (1 H), 7.93 (1 H), 5.38-5.42 (1 H), 3.20 (3 H), 2.21-2.29 (1 H), 2.03-2.10 (1 H), 1.38-1.88 (7 H), 1.20-1.31 (1 H), 1.04-1.11 (1 H); m/z 404.9 (M−H)$^-$.

Examples 25-27 of general Formula (1A-2) are provided below.

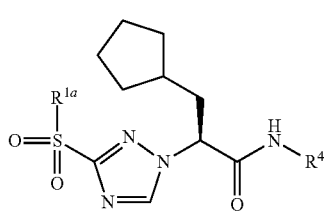

(1A-2)

Example 25

(S)-3-cyclopentyl-N-(5-methylpyridin-2-yl)-2-(3-(methylsulfonyl)-1H-1,2,4-triazol-1-yl)propanamide Formula (1A-2) wherein $R^{1a}$ is methyl and $R^4$ is

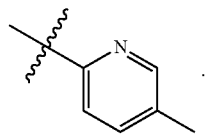 [SMILES: *c1ccc(C)cn1]

To a stirred solution of 2-amino-5-picoline (33 mg, 0.307 mmol) in anhydrous toluene was added AlMe$_3$ (2.0 M in toluene, 0.164 mL, 0.327 mmol). The mixture was stirred at room temperature for 45 minutes, and then added the solution of 44 mg (0.15 mmol) of Intermediate I-5b in dichloroethane (2 mL). The reaction mixture was heated at 80° C. for 18 hours and then cooled to room temperature and saturated aqueous potassium sodium tartrate tetrahydrate was added. The mixture was extracted with CH$_2$Cl$_2$. The combined extracts were dried over MgSO$_4$ and flash column chromatography (SiO$_2$, heptane/ethyl acetate, 25 to 80%) to afford the title compound. $^1$H NMR (400 MHz, $d_6$-DMSO) δ 11.13 (1H), 9.08 (1H), 8.18 (1H), 7.85-7.92 (1H), 7.58-7.63 (1H), 5.41-5.50 (1H), 3.28 (3H), 2.20-2.31 (4H), 2.11-2.20 (1H), 1.46-1.68 (5H), 1.38-1.46 (2H), 1.21-1.32 (1H), 1.02-1.19 (1H); m/z 378.1 (M+H)$^+$, 376.1 (M−H)$^-$.

Example 26

(S)-3-cyclopentyl-N-(1-methyl-1H-pyrazol-3-yl)-2-(3-(methylsulfonyl)-1H-1,2,4-triazol-1-yl)propanamide Formula (1A-2) wherein $R^{1a}$ is methyl and $R^4$ is

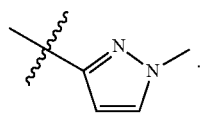 [SMILES: *c1ccn(C)n1]

Example 26 was synthesized in an analogous manner to that of Example 25 from Intermediate I-5b and 3-amino-1-methylpyrazole. $^1$H NMR (400 MHz, CDCl$_3$) δ 9.18 (1 H) 8.59 (1 H) 7.25 (1 H) 6.57 (1 H) 5.24-5.28 (1 H) 3.79 (3 H)) 3.30 (3 H) 2.19-2.29 (2 H) 1.42-1.76 (5 H) 1.02-1.15 (2 H); m/z 365.4 (M−H)$^+$.

Example 27

(S)-3-cyclopentyl-N-(5-methylpyrazin-2-yl)-2-(3-(methylsulfonyl)-1H-1,2,4-triazol-1-yl)propanamide Formula (1A-2) wherein $R^{1a}$ is methyl and $R^4$ is

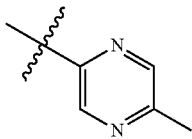

Example 27 was synthesized in an analogous manner to that of Example 25 from Intermediate I-5b and 2-amino-5-methylpyrazine. $^1$H NMR (400 MHz, CDCl$_3$) δ 9.123 (1 H), 9.03 (1 H), 8.57 (1 H), 8.08 (1 H), 5.44-5.248 (1 H), 3.33 (3 H), 2.49 (3 H), 2.27-2.32 (2 H), 1.42-1.81 (7 H), 1.08-1.24 (2 H); m/z 377.4 (M−H)$^+$.

Examples 28-42 of general Formula (1A-3) are provided below.

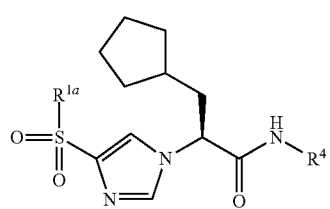

(1A-3)

Example 28

(S)-3-cyclopentyl-2-(4-(isopropylsulfonyl)-1H-imidazol-1-yl)-N-(5-methylpyridin-2-yl)propanamide Formula (1A-3) wherein $R^{1a}$ is isopropyl and $R^4$ is

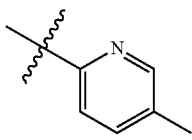

To a stirred solution of 2-amino-5-picoline (36 mg, 0.332 mmol) in anhydrous toluene was added AlMe$_3$ (2.0 M in toluene, 0.177 mL, 0.354 mmol). The mixture was stirred at room temperature for 45 minutes, and then a solution of 52 mg (0.158 mmol) of Intermediate I-7a1 in dichloroethane (2 mL) was added. The reaction mixture was heated at 80° C. for 16 hours and then cooled to room temperature and saturated aqueous potassium sodium tartrate tetrahydrate was added. The mixture was extracted with CH$_2$Cl$_2$. The combined extracts were dried over MgSO$_4$ and flash column chromatography (SiO$_2$, ethyl acetate/heptane, 50 to 100%) to afford the title compound. $^1$H NMR (400 MHz, d$_6$-DMSO) δ 10.97 (1H), 9.08 (1H), 8.17 (1H), 7.97-8.02 (2H), 7.85-7.89 (1H), 7.56-7.61 (1H), 5.18-5.5.23 (1H), 3.22-3.30 (1H), 2.22 (3H), 2.02-2.22 (2H), 1.32-1.64 (7H), 1.24-1.32 (1H), 1.10-1.15 (6H), 0.97-1.07 (1H); m/z 404.9 (M+H)$^+$, 403.0 (M−H)$^-$.

Example 29

(S)-3-cyclopentyl-2-(4-(isopropylsulfonyl)-1H-imidazol-1-yl)-N-(1-methyl-1H-pyrazol-3-yl)propanamide Formula (1A-3) wherein $R^{1a}$ is isopropyl and $R^4$ is

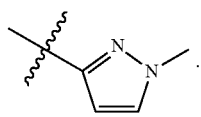

Example 29 was synthesized in an analogous manner to that of Example 28 from Intermediate I-7a1 and 3-amino-1-methylpyrazole. $^1$H NMR (400 MHz, CDCl$_3$) δ 8.78 (1 H), 7.90 (2 H), 7.26 (2 H), 6.60 (1 H), 6.52 (1 H), 5.31 (2 H), 3.79 (3 H), 2.15 (2 H), 1.63-1.77 (2 H), 1.59 (2H), 1.47 (2 H), 1.34-1.40 (6 H), 1.04-1.20 (1 H); m/z 394.2 (M+H)$^+$.

Example 30

(S)-3-cyclopentyl-2-(4-(isopropylsulfonyl)-1H-imidazol-1-yl)-N-(5-methylpyrazin-2-yl)propanamide Formula (1A-3) wherein $R^{1a}$ is isopropyl and $R^4$ is

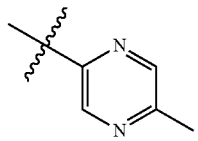

Example 30 was synthesized in an analogous manner to that of Example 28 from Intermediate I-7a1 and 2-amino-5-methylpyrazine. $^1$H NMR (400 MHz, CDCl$_3$) δ 9.36 (1 H), 9.29 (1 H), 8.10 (1 H), 8.03 (2 H), 5.26-5.29 (1 H), 3.38-3.45 (1 H), 2.50 (3 H), 2.08-2.19 (2 H), 1.43-1.64 (5 H), 1.32-1.41 (8 H), 1.06-1.17 (2 H); m/z 406.2 (M+H)$^+$.

Example 31

(S)-3-cyclopentyl-2-(4-(ethylsulfonyl)-1H-imidazol-1-yl)-N-(1-methyl-1H-pyrazol-3-yl)propanamide Formula (1A-3) wherein $R^{1a}$ is ethyl and $R^4$ is

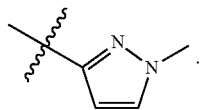 [SMILES: *c1ccn(C)n1]

Example 31 was synthesized according to the procedure described in Example 28 from Intermediate I-7a2 and 3-amino-1-methylpyrazole. $^1$H NMR (400 MHz, CDCl$_3$) δ 9.45 (1 H) 7.92 (2 H) 7.26 (1 H) 6.56 (1 H) 4.96-4.99 (1 H) 3.75 (3 H) 3.24-3.29 (2 H) 2.13-2.19 (1 H) 1.40-1.69 (8 H) 1.25-1.31 (3 H) 1.04-1.12 (2 H); m/z 380.5 (M+H)$^+$.

Example 32

(S)-3-cyclopentyl-2-(4-(ethylsulfonyl)-1H-imidazol-1-yl)-N-(5-methylpyridin-2-yl)propanamide Formula (1A-3) wherein $R^{1a}$ is ethyl and $R^4$ is

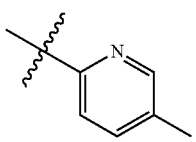

Example 32 was synthesized according to the procedure described in Example 28 from Intermediate I-7a2 and 2-amino-5-picoline. $^1$H NMR (400 MHz, CDCl$_3$) δ 8.20 (2 H), 7.86-7.94 (3 H), 5.45-5.52 (1 H), 3.23 (2 H), 2.40 (3 H), 2.20-2.31 (1 H), 2.07-2.17 (1 H), 1.38-1.92 (7 H), 1.20-1.34 (4 H), 1.00-1.15 (1 H); m/z 391.5 (M+H)$^+$.

Example 33

(S)-3-cyclopentyl-2-(4-(ethylsulfonyl)-1H-imidazol-1-yl)-N-(5-methylpyrazin-2-yl)propanamide Formula (1A-3) wherein $R^{1a}$ is ethyl and $R^4$ is

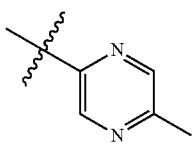

Example 33 was synthesized according to the procedure described in Example 28 from Intermediate I-7a2 and 2-amino-5-methylpyrazine. $^1$H NMR (400 MHz, CDCl$_3$) δ 9.31 (1 H), 9.06 (1 H), 8.11 (1 H), 7.95 (1 H), 7.92 (1 H), 5.11 (1 H), 3.30 (2 H), 2.52 (3 H), 2.08-2.24 (2 H), 1.38-1.79 (7 H), 1.32 (3 H), 1.04-1.20 (2 H); m/z 390.4 (M–H)$^-$.

Example 34

(S)-3-cyclopentyl-N-(5-methylpyrazin-2-yl)-2-(4-(methylsulfonyl)-1H-imidazol-1-yl)propanamide Formula (1A-3) wherein $R^{1a}$ is methyl and $R^4$ is

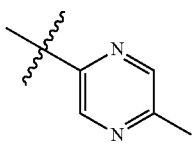

Example 34 was synthesized according to the procedure described in Example 28 from Intermediate I-7a3 and 2-amino-5-methylpyrazine. $^1$H NMR (400 MHz, DMSO-d$_6$) δ 9.15 (1 H), 8.30-8.36 (1 H), 8.02-8.07 (2 H), 5.27 (1 H), 3.13 (3 H), 2.45 (3 H), 2.17-2.27 (1 H), 2.05-2.16 (1 H), 1.38-1.73 (7 H), 1.25-1.36 (1 H), 1.00-1.15 (1 H); m/z 376.4 (M–H)$^-$.

Example 35

(S)-3-cyclopentyl-N-(5-methylpyridin-2-yl)-2-(4-(methylsulfonyl)-1H-imidazol-1-yl)propanamide Formula (1A-3) wherein $R^{1a}$ is methyl and $R^4$ is

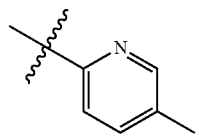

Example 35 was synthesized according to the procedure described in Example 28 from Intermediate I-7a3 and 2-amino-5-picoline. $^1$H NMR (400 MHz, DMSO-d$_6$) δ 8.17-8.19 (1 H), 8.03 (1 H), 8.00 (1 H), 7.93 (1 H), 7.60-7.65 (1 H), 5.23 (1 H), 3.13 (3 H), 2.25 (3 H), 2.05-2.21 (2 H), 1.36-1.71 (7 H), 1.24-1.35 (1 H), 1.04-1.14 (1 H); m/z 377.5 (M+H)$^+$.

Example 36

(S)-3-cyclopentyl-N-(1-methyl-1H-pyrazol-3-yl)-2-(4-(methylsulfonyl)-1H-imidazol-1-yl)propanamide Formula (1A-3) wherein $R^{1a}$ is methyl and $R^4$ is

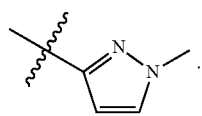 [SMILES: *c1ccn(C)n1]

Example 36 was synthesized according to the procedure described in Example 28 from Intermediate I-7a3 and 3-amino-1-methylpyrazole. $^1$H NMR (400 MHz, DMSO-d$_6$) δ 11.02 (1 H) 7.99 (1 H) 7.57 (1 H) 6.41 (1 H) 5.09 (1 H) 3.74 (3 H) 3.12 (3 H) 2.00-2.19 (2 H) 1.37 (9 H); m/z 364.4 (M–H)$^-$.

Example 37

(S)-benzyl 6-(3-cyclopentyl-2-(4-(methylsulfonyl)-1H-imidazol-1-yl)propanamido)nicotinate Formula (1A-3) wherein $R^{1a}$ is methyl and $R^4$ is

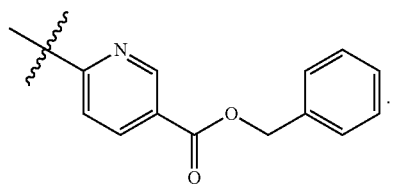 [SMILES: *c1ccc(C(=O)OCc2ccccc2)cn1]

Intermediate (I-24a) (852 mg, 2.98 mmol) was stirred in dry dichloromethane (50 mL) at room temperature under nitrogen. One drop of DMF was added, followed by oxalyl chloride (0.65 mL, 7.5 mmol). After bubbling subsided, the reaction was left stirring for 90 minutes and then evaporated. The residue was re-dissolved and re-evaporated with two successive portions of 1,2-dichloroethane to remove unreacted oxalyl chloride. The residue was then dissolved in dry dichloromethane (60 mL), and intermediate (I-28a) (816 mg, 3.58 mmol) and pyridine (0.65 mL, 8.0 mmol) were added. The reaction was stirred at room temperature under nitrogen for 18 hours, washed twice with water and once with brine, dried over sodium sulfate, filtered, evaporated. The residue was purified by silica gel chromatography, using a pre-packed 80 g column, and eluting with 10% ethyl acetate/heptane with a linear gradient to 70% ethyl acetate/heptane. The product fractions were combined, evaporated, and dried under high vacuum at 60° C. to afford the title compound (1.08 g, 2.17 mmol, 73%) as a white glass. $^1$H NMR (400 MHz, CDCl$_3$) δ 8.92 (1 H), 8.88 (1 H), 8.31-8.34 (1 H), 8.19-8.22 (1 H), 7.89 (1 H), 7.83 (1 H), 7.33-7.44 (5 H), 5.36 (2 H), 4.92-4.95 (1 H), 3.21 (s, 3 H), 2.15-2.19 (2 H), 1.45-1.76 (7 H), 1.09-1.18 (2 H); m/z 496.9 (M+H)$^+$.

Example 38

(S)-6-(3-cyclopentyl-2-(4-(methylsulfonyl)-1H-imidazol-1-yl)propanamido)nicotinic acid Formula (1A-3) wherein $R^{1a}$ is methyl and $R^4$ is

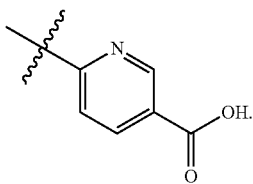 [SMILES: *c1ccc(C(=O)O)cn1]

The compound of Example 37 (1.08 g, 2.18 mmol) was dissolved in ethyl acetate (10 mL) and ethanol (20 mL) in a Parr bottle. 10% Palladium on carbon was added (200 mg), and the mixture was shaken under 30 psi hydrogen for 90 minutes. The mixture was filtered, evaporated, and dried under high vacuum to a clear glass. The glass was triturated with diethyl ether and stirred for 1 hour. The resulting material was filtered, washed with ether, and dried under high vacuum at 60° C. to afford the title compound (651.1 mg, 1.60 mmol, 73%) as a white powder. $^1$H NMR (400 MHz, DMSO-d$_6$) δ 11.45 (1 H), 8.83 (1 H), 8.26-8.28 (1 H), 8.09-8.12 (1 H), 8.00-8.02 (2 H), 5.24-5.28 (1 H), 3.10 (3 H), 2.10-2.19 (2 H), 1.29-1.64 (8 H), 1.01-1.08 (1 H); m/z 406.9 (M+H)$^+$.

Example 39

(S)-6-(3-cyclopentyl-2-(4-(ethylsulfonyl)-1H-imidazol-1-yl)propanamido)nicotinic acid Formula (1A-3) wherein $R^{1a}$ is ethyl and $R^4$ is

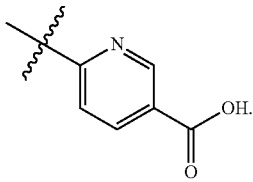 [SMILES: *c1ccc(C(=O)O)cn1]

To a solution of intermediate (I-34c1) (100 mg, 0.196 mmol) in 30 mL of a %:1 mixture of ethanol:ethyl acetate was added Pd(OH)$_2$/C (50 mg) at room temperature, and the mixture was stirred for 12 hours under 50 psi of H$_2$. TLC (1:1 petroleum ether/ethyl acetate) indicated the reaction was complete. The reaction mixture was filtered and the filtrate was concentrated in vacuo. The residue was purified by prep-HPLC to afford the title compound (17.5 mg, 21.2%) as a white solid. $^1$H NMR (400 MHz, CD$_3$OD) δ 8.81 (1 H), 8.23 (1 H), 8.10 (1 H), 7.95 (2 H), 5.11 (1 H), 3.13 (2 H), 2.11 (2 H), 1.71 (1 H), 1.58 (4 H), 1.41 (2 H), 1.24 (1 H), 1.12 (3 H), 1.08 (1 H); m/z 421.3 (M+H)$^+$.

Example 40

(S)-6-(3-cyclopentyl-2-(4-(isopropylsulfonyl)-1H-imidazol-1-yl)propanamido)nicotinic acid Formula (1A-3) wherein $R^{1a}$ is isopropyl and $R^4$ is

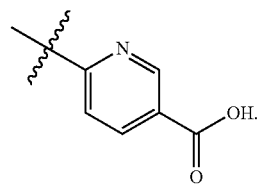 [SMILES: *c1ccc(C(=O)O)cn1]

To a solution of intermediate (I-34c2) (80 mg, 0.153 mmol) in 20 mL of a 5:1 mixture of ethanol:ethyl acetate was added Pd(OH)$_2$/C (40 mg) at room temperature, and the mixture was stirred for 12 hours under 50 psi of H$_2$. TLC (1:1 petroleum ether/ethyl acetate) indicated the reaction was complete. The reaction mixture was filtered and the filtrate was concentrated in vacuo. The residue was purified by prep-HPLC to afford the title compound (22.7 mg, 34.3%) as a white solid. $^1$H NMR (400 MHz, CD$_3$OD) δ 8.90 (1 H), 8.32 (1 H), 8.19 (1 H), 8.03 (2 H), 5.21 (1 H), 3.31 (1 H), 2.21 (2 H), 1.80 (1 H), 1.65 (4 H), 1.50 (2 H), 1.30 (7 H), 1.12 (1 H); m/z 435.5 (M+H)$^+$.

Example 41

(S)-6-(2-(4-(cyclobutylsulfonyl)-1H-imidazol-1-yl)-3-cyclopentylpropanamido)nicotinic acid Formula (1A-3) wherein $R^{1a}$ is cyclobutyl and $R^4$ is

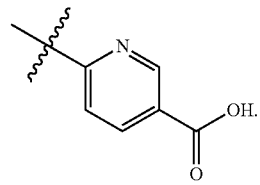 [SMILES: *c1ccc(C(=O)O)cn1]

To a solution of intermediate (I-34c3) (200 mg, 0.373 mmol) in 30 mL of a 5:1 mixture of ethanol:ethyl acetate was added Pd(OH)$_2$/C (100 mg) at room temperature, and the mixture was stirred for 12 hours under 50 psi of H$_2$. TLC (1:1 petroleum ether/ethyl acetate) indicated the reaction was complete. The reaction mixture was filtered and the filtrate was concentrated in vacuo. The residue was purified by prep-HPLC to afford the title compound (66.5 mg, 39.9%) as a white solid. $^1$H NMR (400 MHz, CD$_3$OD) δ 8.89 (1 H), 8.31 (1 H), 8.20 (1 H), 8.02 (2 H), 5.21 (1 H), 4.04 (1 H), 2.49 (2 H), 2.21 (4 H), 1.98 (2 H), 1.80 (1 H), 1.60 (6 H), 1.30 (1 H), 1.11 (1 H); m/z 447.5 (M+H)$^+$.

Example 42

6-[(S)-3-cyclopentyl-2-(4-dimethylsulfamoyl-imidazol-1-yl)-propionylamino]-nicotinic acid Formula (1A-3) wherein $R^{1a}$ is dimethylamino and $R^4$ is

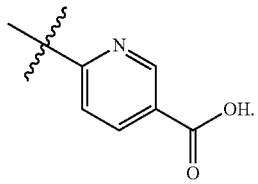 [SMILES: *c1ccc(C(=O)O)cn1]

To a solution of intermediate (I-35e) (80 mg, 0.152 mmol) in 20 mL of 5:1 ethanol:ethyl acetate was added Pd(OH)$_2$/C (40 mg) at room temperature, and the mixture was stirred for 12 hours under 50 psi of H$_2$. TLC (1:1 petroleum ether/ethyl acetate) indicated the reaction was complete. The reaction mixture was filtered and the filtrate was concentrated in vacuo. The residue was purified by prep-HPLC to afford the title compound (5.3 mg, 14.6%) as a white solid. $^1$H NMR (400 MHz, CD$_3$OD) δ8.80 (1 H), 8.22 (1 H), 8.08 (1 H), 7.85 (2 H), 5.11 (1 H), 2.65 (6 H), 2.11 (2 H), 2.21 (4 H), 1.71 (1 H), 1.58 (4 H), 1.42 (2 H), 1.21 (1 H), 1.08 (1 H); m/z 436.4 (M+H)$^+$.

Examples 43-67 of general Formula (1A-4) are provided below.

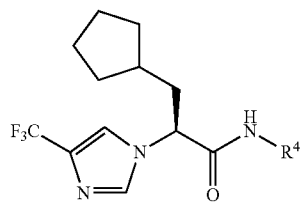

(1A-4)

Example 43

(S)-3-cyclopentyl-N-(1-methyl-1H-pyrazol-3-yl)-2-(4-(trifluoromethyl)-1H-imidazol-1-yl)propanamide Formula (1A-4) wherein $R^4$ is

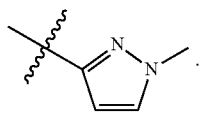 [SMILES: *c1ccn(C)n1]

To a stirred solution of 2-amino-N-methyl-pyrazole (49.1 mg, 0.506 mmol) in 3 mL anhydrous toluene was added a solution of AlMe$_3$ (0.270 mL, 2.00 M in toluene, 0.54 mmol). After stirring for 35 minutes at room temperature a solution of 70 mg of Intermediate I-8a in 2 mL anhydrous dichloroethane was added. The reaction was heated to 80° C. for 18 hours. The reaction mixture was cooled and stirred for several minutes with saturated Rochelle's salt and extracted twice with ethyl acetate. The combined organics were dried over MgSO$_4$, filtered, and the filtrate was concentrated under reduced pressure. The residue was purified by flash chromatography on a Biotage column (SiO$_2$, ethyl acetate/hepatane, 50 to 100%)). The purified fractions were collected, concentrated, and residue was titurated in diethyl ether to afford the title compound. $^1$H NMR (400 MHz, DMSO) δ10.97 (1 H), 7.91 (1H), 7.89 (1 H), 7.54 (1 H), 6.38 (1 H), 5.02-5.05 (1 H), 3.71 (3 H), 2.01-2.08 (2 H), 1.40-1.62 (7 H), 1.20-1.22 (1 H), 1.04-1.07 (1 H); m/z 356.2 (M+H)$^+$.

Example 44

(S)-3-cyclopentyl-N-(5-methylpyridin-2-yl)-2-(4-(trifluoromethyl)-1H-imidazol-1-yl)propanamide Formula (1A-4) wherein $R^4$ is

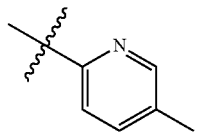

Example 44 was synthesized in an analogous manner to that of Example 43 from Intermediate I-8a and 2-amino-5-methylpyridine. $^1$H NMR (400 MHz, CDCl$_3$) δ 9.02 (1 H), 8.07 (2H), 7.69 (1 H), 7.54 (2 H), 4.73-4.77 (1 H), 2.28 (3 H), 2.13-2.20 (2 H), 1.45-1.67 (7 H), 1.10-1.12 (2 H); m/z 367.0 (M+H)$^+$.

Example 45

(S)-3-cyclopentyl-N-(5-methylpyrazin-2-yl)-2-(4-(trifluoromethyl)-1H-imidazol-1-yl)propanamide Formula (1A-4) wherein $R^4$ is

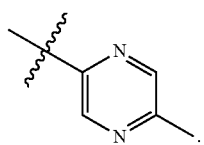 [SMILES: *c1cnc(C)cn1]

Example 45 was synthesized in an analogous manner to that of Example 43 from Intermediate I-8a and 2-amino-5-methylpyrazine. $^1$H NMR (400 MHz, CDCl$_3$) δ 9.34 (1 H), 8.65 (1H), 8.11 (1 H), 7.72 (1 H), 7.53 (1 H), 4.83-4.86 (1 H), 2.52 (3 H), 2.21-2.24 (2 H), 2.17 (1 H), 1.27-1.50 (6 H), 1.08-1.14 (2 H); m/z 368.0 (M+H)$^+$.

Example 46

(S)-methyl 6-(3-cyclopentyl-2-(4-(trifluoromethyl)-1H-imidazol-1-yl)propanamido)nicotinate Formula (1A-4) wherein R⁴ is

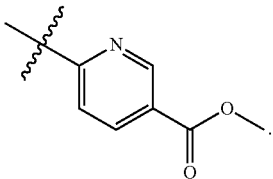 [SMILES: *c1ccc(C(=O)OC)cn1]

To a stirred solution of Intermediate (I-8b) (328.5 mg, 1.189 mmol) in anhydrous dichloromethane (12 mL) at room temperature under nitrogen was added oxalyl chloride followed by 1 drop of DMF. The reaction bubbled and then subsided. It was left stirring for 90 minutes and then evaporated under reduced pressure. 1,2-dichloroethane was added and concentrated two times. The residue was then dissolved in anhydrous dichloromethane (10 mL). Methyl 6-aminonicotinate (221 mg, 1.45 mmol; Aldrich Chemical Company, Inc., Milwaukee, Wis.) was added, followed by pyridine (0.21 mL, 2.6 mmol). The reaction was stirred overnight at room temperature before diluting with ethyl acetate and water. 1M aqueous potassium dihydrogen phosphate was added. The layers were separated, and the organic layer was washed with brine, dried over sodium sulfate, filtered, and concentrated under reduced pressure. The residue was purified (Combi-flash, Redi-sep 40 g, 45% ethyl acetate/heptane) to afford the title compound as an off-white glass. $^1$H NMR (400 MHz, CDCl$_3$) δ 8.89 (1 H), 8.57 (1 H), 8.31-8.33 (1 H), 8.24 (1 H), 7.70 (1 H), 7.51 (1 H), 4.76-4.82 (1 H), 3.92 (3 H), 2.16-2.21 (2 H), 1.48-1.79 (7 H), 1.11-1.17 (2 H); m/z 411.1 (M+H)⁺.

Example 47

(S)-benzyl 6-(3-cyclopentyl-2-(4-(trifluoromethyl)-1H-imidazol-1-yl)propanamido)nicotinate Formula (1A-4) wherein R⁴ is

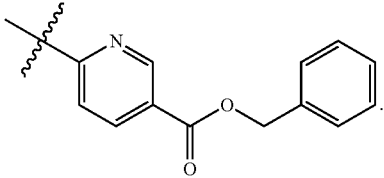 [SMILES: *c1ccc(C(=O)OCc2ccccc2)cn1]

To Intermediate (I-8b) (16.28 g, 59.8 mmol) stirring in dry dichloromethane (400 mL) at room temperature under nitrogen was added 2 drops of DMF. Oxalyl chloride (11 mL, 130 mmol) was added dropwise. After the bubbling subsided the reaction was left stirring for 90 minutes and then concentrated under reduced pressure. Two successive portions of 1,2-dichloroethane were added and evaporated to remove all excess oxalyl chloride. The crude acid chloride was taken up in dichloromethane (150 mL) and stirred at room temperature. Intermediate (I-28a) (14.3 g, 62.5 mmol) and pyridine (10 mL, 130 mmol) were stirred in 400 mL dry dichloromethane. This was added to the acid chloride solution, using another 50 mL dry dichloromethane to complete the transfer. The mixture was left stirring at room temperature under nitrogen for 18 hours. The reaction was diluted with dichloromethane and water, and 1M aqueous phosphoric acid was added. The organic layer was separated and washed sequentially with dilute aqueous potassium carbonate, and brine. This was then dried over sodium sulfate, filtered, and concentrated under reduced pressure to a glass, which was taken up in hot ethyl acetate and stirred at room temperature. A precipitate appeared at about 30 minutes. The mixture was stirred for 16 hours and then filtered. The precipitate was washed with ethyl acetate and then diethyl ether and dried under high vacuum at 60° C. to afford the title compound as a white solid (17.8 g, 36.6 mmol, 61%). The mother liquor was evaporated and purified by silica gel chromatography on a 120 g pre-packed column, eluting with 40% ethyl acetate/heptane. The product fractions were combined, concentrated under reduced pressure, dried under high vacuum to a glass, and converted as previously described to additional product (3.5 g, 7.2 mmol, 12%, total yield 73%). $^1$H NMR (400 MHz, DMSO-d$_6$) δ 11.50 (1 H), 8.87-8.88 (1 H), 8.29-8.32 (1 H), 8.12-8.14 (1 H), 7.93-7.94 (2 H), 7.39-7.46 (2 H), 7.30-7.37 (3 H), 5.32 (2 H), 5.21-5.25 (1 H), 2.06-2.19 (2 H), 1.26-1.63 (8 H), 1.01-1.06 (1 H); m/z 487.5 (M+H)⁺.

Example 48

(S)-6-(3-cyclopentyl-2-(4-(trifluoromethyl)-1H-imidazol-1-yl)propanamido)nicotinic acid Formula (1A-4) wherein R⁴ is

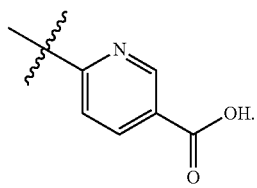 [SMILES: *c1ccc(C(=O)O)cn1]

The compound of Example 47 (4.07 g, 8.35 mmol) was added to a 500 mL Parr bottle, followed by ethyl acetate (50 mL) and ethanol (100 mL). The mixture was warmed until all of the solid dissolved, and then cooled to room temperature. 10% Pd/C (450 mg) was added, and the mixture was shaken under 50 psi hydrogen for 90 minutes. The reaction was filtered through a microfiber filter. The filtrate was concentrated under reduced pressure and dried under high vacuum at 50° C. to afford product as a glassy solid (3.0 g, 7.75 mmol, 90.6%). The glassy solid was stirred overnight in diethyl ether. The white solid precipitate was filtered, washed with diethyl ether, suction dried, and dried under high vacuum at 50° C. to afford the title compound as a white solid. $^1$H NMR (400 MHz, DMSO-d$_6$) δ 13.10-13.25 (1 H), 11.44 (1 H), 8.83 (1 H), 8.23-8.26 (1 H), 8.09-8.12 (1 H), 7.94-7.95 (2 H), 5.22-5.26 (1 H), 2.06-2.17 (2 H), 1.29-1.64 (8 H), 1.04-1.07 (1 H); m/z 397.3 (M+H)⁺.

Example 49

(S)-3-cyclopentyl-N-(2-ethyl-2H-[1,2,3]triazol-4-yl)-2-(4-trifluoromethyl-1H-imidazol-1-yl)propanamide Formula (1A-4) wherein $R^4$ is

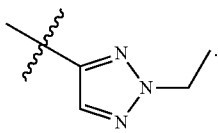 [SMILES: *c1cnn(CC)n1]

Example 49 was synthesized in an analogous manner to that of Example 43 from Intermediate I-8a and 2-ethyl-2H-1,2,3-triazol-4-amine (Chembridge Corporation, San Diego, Calif.). $^1$H NMR (400 MHz, CDCl$_3$) δ 8.19 (1 H), 7.93 (1 H), 7.67 (1 H), 7.49 (1 H), 4.74 (1 H), 4.34 (2 H), 2.04-2.34 (2 H), 1.67-1.84 (2 H), 1.57-1.63 (4 H), 1.43-1.54 (4 H), 1.07-1.22 (2 H); m/z 371.2 (M+H+).

Example 50

(S)-3-cyclopentyl-N-(5-((S)-1,2-dihydroxyethyl)pyrazin-2-yl)-2-(4-(trifluoromethyl)-1H-imidazol-1-yl)propanamide Formula (1A-4) wherein $R^4$ is

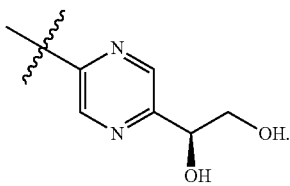 [SMILES: *c1cnc([C@H](O)CO)cn1]

To a solution of Intermediate (I-14a) (75 mg, 0.16 mmol) in THF (2.5 mL) was added 1N HCl (2.4 mL) and this was stirred at room temperature for 18 h. After 1 day, the reaction was extracted with ethyl acetate twice. The combined organics were washed with aqueous saturated NaHCO$_3$ and dried over MgSO$_4$. Purification by silica gel chromatography (12g-Snap Biotage, heptane/ethyl acetate) afforded 30 mg of Example 50 as an oil. $^1$H NMR (400 MHz, CD$_3$OD) δ 9.28 (1 H), 8.50 (1 H), 7.94 (1 H), 7.82 (1 H), 5.16 (1 H), 4.83 (2 H), 4.77 (1 H), 3.77-3.94 (1 H), 3.66-3.77 (1 H), 2.10-2.34 (2 H), 1.40-1.89 (7 H), 1.22-1.36 (2 H); m/z 414.1 (M+H$^+$).

Example 51

(S)-3-cyclopentyl-N-[5-(methylsulfonyl)pyridin-2-yl]-2-[4-(trifluoromethyl)-1H-imidazol-1-yl]propanamide Formula (1A-4) wherein $R^4$ is

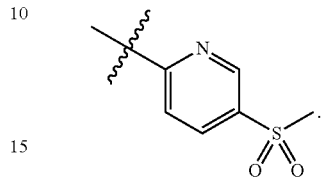

Intermediate (I-19a) (80 mg, 0.29 mmol), 2-bromo-5-(methylsulfonyl)pyridine (69 mg, 0.29 mmol), cesium carbonate (144 mg, 0 44 mmol), Xantphos (26.2 mg, 0.04 mmol), tris(dibenzylideneacetone)palladium (14 mg, 0.015 mmol) were combined in anhydrous degassed toluene (4 mL). The mixture was stirred at 100° C. for 12 hrs. The reaction was diluted with ethyl acetate (50 mL) and washed with H$_2$O (10 mL), NaHCO$_3$ (aq, saturated, 10 mL), and brine (10 mL), and dried (Na$_2$SO$_4$), filtered and concentrated. The crude product was purified by chromatography (silica gel, 0 to100% EtOAc gradient in heptane) to give a gummy residue, which was precipitated using (Et$_2$O/Heptane/Dichloromethane) to afford the title compound as white solid (55 mg, 44%). $^1$H NMR (400 MHz, CDCl$_3$) δ 8.80 (1 H), 8.45 (1 H), 8.35 (1 H), 8.22 (1 H), 7.70 (1 H), 7.50 (1 H), 4.80 (1 H), 2.16-2.25 (2 H), 1.68-1.86 (2 H), 1.60-1.67 (2 H), 1.45-1.56 (3 H), 1.08-1.28 (5 H); m/z 430.9 (M+H)$^+$.

Example 52

6-[(S)-3-cyclopentyl-2-(4-trifluoromethyl-1H-imidazol-1-yl)-propionylamino]-nicotinamide Formula (1A-4) wherein $R^4$ is

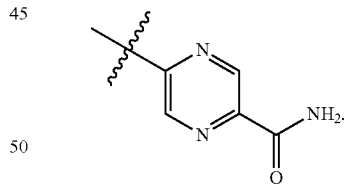

Intermediate (I-21a) (157 mg, 0.378 mmol) was taken up in THF (1.2 mL) and cooled in an ice water bath. To this was added NH$_4$OH (0.8 mL) and this was allowed to slowly warm to room temperature overnight. The reaction mixture was partitioned between water and ethyl acetate. The aqueous layer was extracted with a second portion of ethyl acetate and the combined organics were washed with brine, dried over MgSO$_4$, filtered, and evaporated to give crude material. This material was purified by flash chromatography (SiO$_2$, dichloromethane/methanol, 4 to 10%) to afford 67.7 mg (45.3%) of Example 52 as a tan solid. $^1$H NMR (400 MHz, CDCl$_3$) δ 8.70-8.73 (1 H), 8.09-8.19 (2 H), 7.68 (1 H), 7.53 (1 H), 4.96 (1 H), 3.30-3.33 (1 H), 2.98 (2 H), 2.01-2.17 (1 H), 1.69 (1 H), 1.40-1.62 (4 H), 1.02-1.26 (4 H); m/z 396.0 (M+H+).

Example 53

(S)-benzyl 5-(3-cyclopentyl-2-(4-(trifluoromethyl)-1H-imidazol-1-yl)propanamido)pyrazine-2-carboxylate Formula (1A-4) wherein $R^4$ is

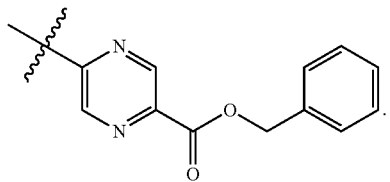

Intermediate (I-8b) (157.5 mg, 0.57 mmol) was dissolved in dry dichloromethane (6 mL) and stirred at room temperature under nitrogen. One drop of DMF was added, followed by oxalyl chloride (0.10 mL, 1.18 mmol). After bubbling had subsided, the mixture was left stirring for 90 minutes and then evaporated. The residue was dissolved in two successive portions of 1,2-dichloroethane and evaporated to remove excess oxalyl chloride, and the residue was dissolved in dry dichloromethane (4 mL). Intermediate (I-22a) (161 mg, 0.70 mmol) and pyridine (0.10 mL, 1.24 mmol) were dissolved in dry dichloromethane (5 mL) and added to the solution of acid chloride. The reaction was stirred at room temperature under nitrogen for 2 days. The reaction was then diluted with dichloromethane and water, and the organic layer was separated, washed with brine, dried over sodium sulfate, filtered, and evaporated. The residue was purified by silica gel chromatography on a 40 g pre-packed column, using 25% ethyl acetate/heptane, linear gradient to 100% ethyl acetate. The product fractions were combined, evaporated, and dried under high vacuum to afford the title compound (145 mg, 0.3 mmol, 52%) as a yellow glass. $^1$H NMR (400 MHz, CDCl$_3$) δ 9.57 (1 H), 8.96-8.97 (1 H), 8.30-8.32 (1 H), 7.69 (1 H), 7.50 (1 H), 7.39-7.47 (2 H), 7.32-7.38 (3 H), 5.45 (2 H), 4.80-4.85 (1 H), 2.04-2.25 (2 H), 1.49-1.81 (7 H), 1.11-1.18 (2 H); m/z 487.9 (M+H)$^+$.

Example 54

(S)-5-(3-cyclopentyl-2-(4-(trifluoromethyl)-1H-imidazol-1-yl)propanamido)pyrazine-2-carboxylic acid, Formula (1A-4) wherein $R^4$ is

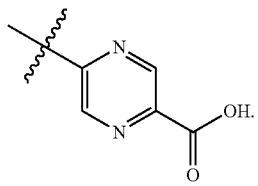

The compound of Example 53 (145 mg, 0.3 mmol) was dissolved in ethanol (6 mL) and ethyl acetate (3 mL) in a 250 mL Parr bottle. 10% palladium on carbon (20 mg) was added, and the reaction was shaken under 50 psi hydrogen for 90 minutes. The mixture was filtered, evaporated, and dried under high vacuum to afford the title compound (109.2 mg, 0.27 mmol, 92%). $^1$H NMR (400 MHz, DMSO-d$_6$) δ 11.76 (1 H), 9.33 (1 H), 8.95 (1 H), 7.97 (2 H), 5.25-5.29 (1 H), 2.17-2.25 (1 H), 2.05-2.15 (1 H), 1.28-1.64 (8 H), 1.01-1.08 (1 H); m/z 398.3 (M+H)$^+$.

Example 55

(S)-ethyl 2-(3-(3-cyclopentyl-2-(4-(trifluoromethyl)-1H-imidazol-1-yl)propanamido)-1H-pyrazol-1-yl)acetate Formula (1A-4) wherein $R^4$ is

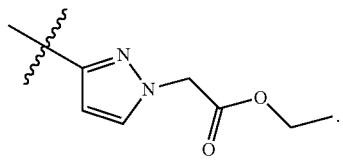 [SMILES: *c1ccn(CC(=O)OCC)n1]

Intermediate (I-8b) (145 mg, 0.525 mmol) was dissolved in dry dichloromethane (5 mL) and stirred at room temperature under nitrogen. One drop of DMF was added, followed by oxalyl chloride (0.095 mL, 1.1 mmol). After bubbling had subsided, the mixture was left stirring for 90 minutes and then evaporated. The residue was dissolved in two successive portions of 1,2-dichloroethane and evaporated to remove excess oxalyl chloride, and the residue was dissolved in dry dichloromethane (4 mL). Ethyl 2-(3-amino-1H-pyrazol-1-yl)acetate hydrochloride (Oakwood Products, Inc., West Columbia, S.C.) (130 mg, 0.630 mmol) and pyridine (0.130 mL, 1.61 mmol) were dissolved in dry dichloromethane (5 mL) and added to the solution of acid chloride. The reaction was stirred at room temperature under nitrogen for 1 day. The reaction was then diluted with dichloromethane and water, and the organic layer was separated, washed with brine, dried over sodium sulfate, filtered, and evaporated. The residue was purified by silica gel chromatography on a 12 g pre-packed column, using 50% ethyl acetate/heptane, linear gradient to 75% ethyl acetate. The product fractions were combined, evaporated, and dried under high vacuum to afford the title compound (153 mg, 68%) as a white glass. $^1$H NMR (400 MHz, CDCl$_3$) δ 8.36 (1 H), 7.71 (1 H), 7.50 (1 H), 7.36 (1 H), 6.74 (1 H), 4.70-4.75 (3 H), 4.20-4.25 (2 H), 2.06-2.20 (2 H), 1.43-1.77 (7 H), 1.25-1.29 (3 H), 1.07-1.15 (2 H); m/z 428.0 (M+H)$^+$.

Example 56

(S)-3-cyclopentyl-N-(1-(2-hydroxy-2-methylpropyl)-1H-pyrazol-3-yl)-2-(4-(trifluoromethyl)-1H-imidazol-1-yl)propanamide Formula (1A-4) wherein $R^4$ is

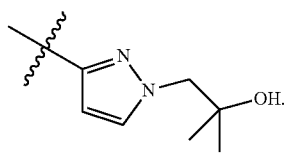 [SMILES: *c1ccn(CC(C)(C)O)n1]

Under a nitrogen atmosphere intermediate (I-27d) was dissolved in anhydrous toluene (4 mL). Trimethylaluminum (2.00 M in toluene, 0.488 mL) was added dropwise. This mixture was stirred at room temperature for 30 min before a solution of intermediate (I-8a) in 4 mL 1,2-dichloroethane was added. The reaction was then stirred at 80° C. After 21 h, the reaction was quenched with saturated aqueous Rochelle's salt. This was extracted twice with dichloromethane. The combined organics were dried over MgSO₄ and concentrated to afford material that was most likely a mixture of the hydroxy product and silyl-protected product. This material was then dissolved in anhydrous THF (10 mL) and tetrabutylammonium fluoride (1.00 M in THF, 3.77 mL) was added. This was stirred at room temperature for two days before partitioning between ethyl acetate and water. The aqueous layer was extracted with ethyl acetate and the combined organics dried over MgSO₄. Purification by silica gel chromatography (40 g ISCO, 20-100% EtOAc in heptane), followed by filtering through a course frit to remove any solids, and triturating several times with dichloromethane/ether and then with ether afforded the title compound as a white solid (0.1563 g). $^1$H NMR (400 MHz, CDCl$_3$) δ 9.03 (1 H), 7.80 (1 H), 7.56 (1 H), 7.33 (1 H), 6.74 (1 H), 4.83 (1 H), 3.99 (2 H), 3.93 (1 H), 2.20-2.30 (1 H), 2.07-2.18 (1 H), 1.49-1.88 (7 H), 1.09-1.21 (8 H); m/z 413.9 (M+H)$^+$.

Example 57

(S)-2-(3-(3-cyclopentyl-2-(4-(trifluoromethyl)-1H-imidazol-1-yl)propanamido)-1H-pyrazol-1-yl)acetic acid Formula (1A-4) wherein R$^4$ is

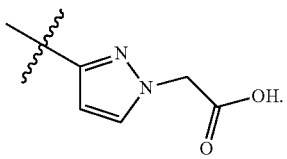 [SMILES: *c1ccn(CC(=O)O)n1]

The compound of Example 55 (153 mg, 0.358 mmol) and lithium hydroxide (50.6 mg, 1.18 mmol) were stirred at room temperature in THF/methanol/water (1:1:1, 3 mL) for 2 hours. The reaction was concentrated, and water and 1N HCl were added to achieve a pH of approximately 4. A thick precipitate settled. Ethyl acetate was added, and the organic layer was washed with brine and dried over sodium sulfate. The mixture was filtered, evaporated, and dried under high vacuum to afford the title compound (31.5 mg, 22%). $^1$H NMR (400 MHz, CD$_3$OD) δ 7.91 (1 H), 7.78 (1 H), 7.52 (1 H), 6.56 (1 H), 5.01-5.05 (1 H), 4.81 (2 H), 2.13-2.17 (2 H), 1.50-1.81 (7 H), 1.21-1.28 (1 H), 1.11-1.18 (1 H); m/z 398.0 (M−H)$^−$.

Example 58

(S)-diethyl(6-(3-cyclopentyl-2-(4-(trifluoromethyl)-1H-imidazol-1-yl)propanamido)pyridin-3-yl)methylphosphonate Formula (1A-4) wherein R$^4$ is

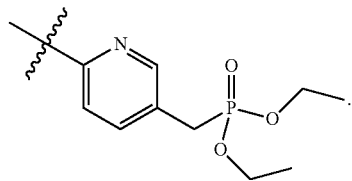 [SMILES: *c1ccc(CP(=O)(OCC)OCC)cn1]

To a solution of intermediate (I-8c) (0.27 g, 0.9 mmol) in dichloromethane (10 mL) was added intermediate (I-26d) (0.223 g, 0.9 mmol) and pyridine (0.22 g, 2.74 mmol) at room temperature. The mixture was stirred for 12 hours at room temperature under nitrogen. TLC (petroleum ether/ethyl acetate=1:1) indicated the reaction was complete. The reaction mixture was concentrated in vacuo and the residue was purified by chromatography on silica to afford the title compound (270 mg, 58.7%) as a light yellow solid. $^1$H NMR (400 MHz, CDCl$_3$) δ 8.79 (1 H), 8.09 (1 H), 8.03 (1 H), 7.62 (1 H), 7.58 (1 H), 7.45 (1 H), 4.73 (1 H), 4.01 (4 H), 3.06 (2 H), 2.08 (2 H), 1.70 (2 H), 1.58 (3 H), 1.48 (2 H), 1.20 (6 H), 1.10 (2 H); m/z 503.3 (M+H)$^+$.

Example 59

(S)-diethyl 6-(3-cyclopentyl-2-(4-(trifluoromethyl)-1H-imidazol-1-yl)propanamido)pyridin-3-ylphosphonate Formula (1A-4) wherein R$^4$ is

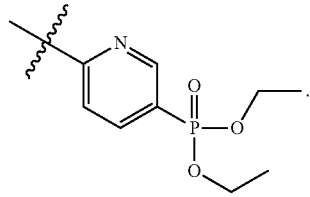 [SMILES: *c1ccc(P(=O)(OCC)OCC)cn1]

To a solution of intermediate (I-8c) (0.329 g, 1.12 mmol) in dichloromethane (8 mL) was added intermediate (I-25a) (0.257 g, 1.12 mmol) and pyridine (0.265 g, 3.36 mmol) at room temperature. The mixture was stirred for 12 hours at room temperature under nitrogen. TLC (petroleum ether/ethyl acetate=0:1) indicated the reaction was complete. The reaction mixture was concentrated in vacuo, the residue was purified by chromatography on silica to afford the title compound (360 mg, 66.2%) as a light yellow solid. $^1$H NMR (400 MHz, CDCl$_3$) δ 8.61 (1 H), 8.39 (1 H), 8.15 (1 H), 8.10 (1 H), 7.63 (1 H), 7.44 (1 H), 4.71 (1 H), 4.07 (4 H), 2.10 (2 H), 1.70 (2 H), 1.58 (2 H), 1.48 (3 H), 1.28 (6 H), 1.10 (2 H); m/z 489.5 (M+H)$^+$.

Example 60

(S)-(6-(3-cyclopentyl-2-(4-(trifluoromethyl)-1H-imidazol-1-yl)propanamido)pyridin-3-yl)methylphosphonic acid Formula (1A-4) wherein $R^4$ is

To a solution of the compound of Example 58 (138 mg, 0.27 mmol) in dichloromethane (2 mL) was added bromotrimethylsilane (2 mL) at room temperature. The mixture was stirred for 12 hours at room temperature under nitrogen. LCMS indicated the reaction was complete. The reaction mixture was quenched with methanol (2 mL), and the mixture was concentrated in vacuo, the residue was purified by prep-HPLC to afford the title compound (54.3 mg, 47.4%) as a white solid. $^1$H NMR (400 MHz, CD$_3$OD): δ 8.23 (1 H), 8.00 (1 H), 7.98 (1 H), 7.81 (1 H), 7.73 (1 H), 5.12 (1 H), 3.06 (2 H), 2.18 (2 H), 1.75 (1 H), 1.70 (1 H), 1.61 (3 H), 1.51 (2 H), 1.30 (1 H), 1.18 (1 H); m/z 445.5 (M–H)$^-$.

Example 61

(S)-6-(3-cyclopentyl-2-(4-(trifluoromethyl)-1H-imidazol-1-yl)propanamido)pyridine-3-sulfonic acid Formula (1A-4) wherein $R^4$ is

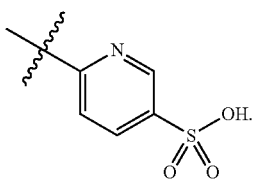 [SMILES: *c1ccc(S(=O)(=O)O)cn1]

To a solution of intermediate (I-8c) (0.40 g, 1.35 mmol) in dichloromethane (10 mL) was added 6-aminopyridinesulfonic acid (0.236 g, 1.35 mmol; Toronto Research Chemicals, North York, Ontario, Canada) and pyridine (0.32 mL, 4.1 mmol) at room temperature. The mixture was refluxed for 12 hours under nitrogen. LCMS indicated the starting material was not consumed completely. The reaction mixture was concentrated in vacuo, the residue was purified by chromatography on silica to afford the title compound (47.2 mg, 8.1%) as a white solid. $^1$H NMR (400 MHz, DMSO-d$_6$): δ 11.18 (1 H), 8.50 (1 H), 7.98 (4 H), 7.03 (1 H), 5.22 (1 H), 2.18 (2 H), 1.60 (4 H), 1.48 (3 H), 1.31 (1 H), 1.11 (1 H); m/z 431.4 (M–H)$^-$.

Example 62

(S)-6-(3-cyclopentyl-2-(4-(trifluoromethyl)-1H-imidazol-1-yl)propanamido)pyridin-3-ylphosphonic acid Formula (1A-4) wherein $R^4$ is

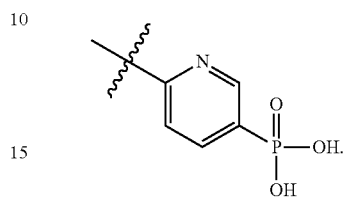

To a solution of the compound of Example 59 (170 mg, 0.348 mmol) in dichloromethane (2 mL) was added bromotrimethylsilane (2 mL) at room temperature, and the mixture was stirred for 12 hours at room temperature under nitrogen. LCMS indicated the reaction was complete. The reaction mixture was quenched with methanol (2 mL) and the mixture was concentrated in vacuo. The residue was purified by prep-HPLC to afford the title compound (47.1 mg, 30.0%) as a white solid. $^1$H NMR (400 MHz, CD$_3$OD): δ 8.64 (1 H) 8.15 (2 H) 7.93 (1 H) 7.81 (1 H) 5.12 (1 H) 2.18 (2 H) 1.80 (1 H) 1.70 (4 H) 1.55 (2 H) 1.30 (1 H) 1.25 (1 H); m/z 431.4 (M–H)$^-$.

Example 63

6-((S)-3-cyclopentyl-2-(4-(trifluoromethyl)-1H-imidazol-1-yl)propanamido)pyridin-3-yl(methyl)phosphinic acid Formula (1A-4) wherein $R^4$ is

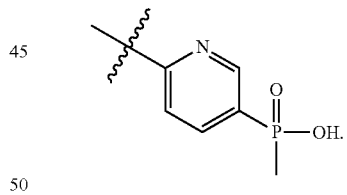

To a solution of intermediate (I-29f) (300 mg, 0.655 mmol) in dichloromethane (4 mL) was added bromotrimethylsilane (2 mL) at room temperature, and the mixture was stirred for 12 hours at room temperature under nitrogen. TLC (dichloromethane/methanol=10:1) indicated the reaction was complete. The reaction mixture was concentrated in vacuo, the residue was washed with water (5 mL), and extracted with dichloromethane (20 mL×3). The combined organic layers were washed with brine, dried over Na$_2$SO$_4$, and evaporated in vacuo. The residue was purified by chromatography on silica to afford the title compound (132.3 mg, 46.9%) as a white solid and as a mixture of diastereomers. $^1$H NMR (400 MHz, CD$_3$OD): δ 8.70 (1 H), 8.28 (1 H), 8.16 (1 H), 8.00 (1 H), 7.88 (1 H), 5.21 (1 H), 2.20 (2 H), 1.84 (1 H), 1.75 (1 H), 1.70 (6 H), 1.60 (2 H), 1.46 (1 H), 1.28 (1 H); m/z 431.4 (M+H)$^+$.

Example 64

(S)-2-(6-(3-cyclopentyl-2-(4-(trifluoromethyl)-1H-imidazol-1-yl)propanamido)pyridin-3-yl)acetic acid Formula (1A-4) wherein $R^4$ is

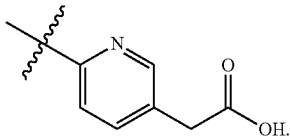 [SMILES: *c1ccc(CC(=O)O)cn1]

A solution of intermediate (I-30g) (207 mg, 0.488 mmol) and lithium iodide (649 mg, 4.88 mmol) in ethyl acetate (5 mL) was refluxed for 24 hours. LCMS indicated the starting material was not consumed completely. The reaction mixture was concentrated in vacuo and the residue was purified by prep-HPLC to afford the title compound (36.9 mg, 18.45%) as a white solid. $^1$H NMR (400 MHz, CD$_3$OD): δ 8.14 (1 H), 7.99 (1 H), 7.85 (1 H), 7.73 (1 H), 7.68 (1 H), 5.10 (1 H), 3.54 (2 H), 2.11 (2 H), 1.75 (1 H), 1.63 (1 H), 1.55 (3 H), 1.48 (2 H), 1.21 (1 H), 1.18 (1 H); m/z 441.4 (M+H)$^+$.

Example 65

(S)-2-(6-(3-cyclopentyl-2-(4-(trifluoromethyl)-1H-imidazol-1-yl)propanamido)pyridin-3-yl)-2-methyl-propanoic acid Formula (1A-4) wherein $R^4$ is

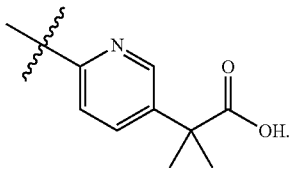 [SMILES: *c1ccc(C(C)(C)C(=O)O)cn1]

A solution of intermediate (I-31 e) (220 mg, 0.486 mmol) and LiI (647 mg, 4.86 mmol) in EtOAc (11 mL) was refluxed for 72 hours. LCMS indicated the starting material was not consumed completely. The reaction mixture was concentrated in vacuo, the residue was purified by prep-HPLC to afford Example 65 (45.6 mg, 21.3%) as a white solid. $^1$H NMR (400 MHz, CD$_3$OD): δ 8.25 (1 H), 7.94 (1 H), 7.85 (1 H), 7.73 (2 H), 5.04 (1 H), 2.10 (2 H), 1.73 (1 H), 1.65 (1 H), 1.55 (3 H), 1.50 (6 H), 1.48 (2 H), 1.23 (1 H), 1.09 (1 H); m/z 439.4 (M+H)$^+$.

Example 66

(S)-2-(6-(3-cyclopentyl-2-(4-(trifluoromethyl)-1H-imidazol-1-yl)propanamido)pyridin-3-ylamino)-2-oxoacetic acid Formula (1A-4) wherein $R^4$ is

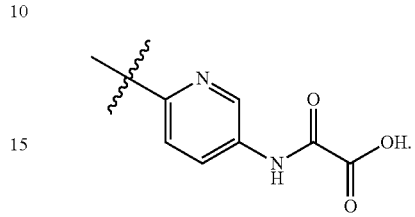

A mixture of intermediate (I-32c) (280 mg, 0.599 mmol) and lithium iodide (796 mg, 5.99 mmol) in ethyl acetate (14 mL) was refluxed for 24 hours. LCMS indicated the reaction was complete. The reaction mixture was concentrated in vacuo and the residue was purified by prep-HPLC to afford the title compound (119.1 mg, 45.3%) as a white solid. $^1$H NMR (400 MHz, CD$_3$OD): δ 8.72 (1 H), 8.16 (2 H), 7.97 (1 H), 7.85 (1 H), 5.17 (1 H), 2.21 (2 H), 1.84 (1 H), 1.75 (1 H), 1.70 (3 H), 1.60 (2 H), 1.32 (1 H), 1.18 (1 H); m/z 440.2 (M+H)$^+$.

Example 67

(S)-3-Cyclopentyl-N-[5-(2-hydroxy-2-methyl-propionylamino)-pyridin-2-yl]-2-(4-trifluoromethyl-imidazol-1-yl)-propionamide Formula (1A-4) wherein $R^4$ is

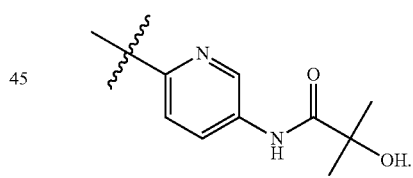

To a solution of intermediate (I-33a) (350 mg, 0.70 mmol) in methanol (8.75 mL) and water (8.75 mL) was added potassium carbonate (146.4 mg, 1.05 mmol) at room temperature, and the mixture was stirred for 12 hours at room temperature. TLC (petroleum ether/ethyl acetate=1:1) indicated the reaction was complete. The reaction mixture was washed with aq. ammonium chloride (20 mL) and the mixture was extracted with ethyl acetate (10 mL×3). The combined organic layers were washed with brine, dried over Na$_2$SO$_4$, and evaporated in vacuo. The residue was purified by chromatography on silica to afford the title compound (177.9 mg, 55.6%) as a white solid. $^1$H NMR (400 MHz, CD$_3$OD): δ 8.63 (1 H), 8.10 (2 H), 7.97 (1 H), 7.86 (1 H), 5.14 (1 H), 2.04 (2 H), 1.85 (1 H), 1.80 (1 H), 1.70 (3 H), 1.58 (2 H), 1.47 (6 H), 1.35 (1 H), 1.20 (1 H); m/z 454.2 (M+H)$^+$.

Examples 68-70 of Formula (1A-5) are provided below.

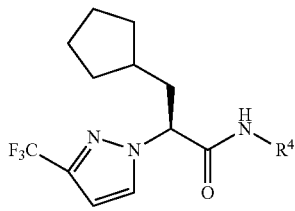
(1A-5)

Example 68

(S)-3-cyclopentyl-N-(1-methyl-1H-pyrazol-3-yl)-2-(3-(trifluoromethyl)-1H-pyrazol-1-yl)propanamide Formula (1A-5) wherein $R^4$ is

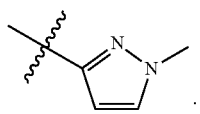 [SMILES: *c1ccn(C)n1]

To a stirred solution of of 1-methyl-3-aminopyrazole (1.219 g, 1.25 mmol) in dichloroethane (2 mL) at 0° C. was added Al(CH$_3$)$_2$Cl (1.0 M, 1.25 mL, 1.25 mmol) and stirred for 15 minutes. A solution of Intermediate I-9a1 (50 mg, 0.16 mmol) in 0.5 mL of 1,2-dichloroethane was then added and the reaction mixture was stirred at room temperature for 16 hours. The mixture was quenched with 20% potassium sodium tartrate tetrahydrate (5 mL) slowly and then diluted with water (30 mL) and extracted with CHCl$_3$ (30 mL). The organic layer was dried over Na$_2$SO$_4$ and concentrated. The residue was purified on Biotage column (SiO$_2$, dichloromethane/methanol, 0 to 8%) to afford the title compound. $^1$H NMR (400 MHz, CDCl$_3$) δ 8.99 (1 H), 7.64 (1H), 7.22 (1 H), 6.60 (2 H), 4.99 (1 H), 3.85 (3 H), 2.22 (2 H),1.73 (1 H), 1.44-1.58 (6 H), 1.10-1.20 (1 H), 1.02-1.07 (1 H); m/z 356.2 (M+H)$^+$.

Example 69

(S)-3-cyclopentyl-N-(5-methylpyridin-2-yl)-2-(3-(trifluoromethyl)-1H-pyrazol-1-yl)propanamide Formula (1A-5) wherein $R^4$ is

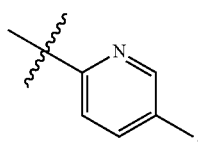

Example 69 was synthesized in an analogous manner to that of Example 68 from Intermediate I-9a1 and 2-amino-5-methylpyridine. $^1$H NMR (400 MHz, CDCl$_3$) δ 9.31 (1 H), 8.94 (1H), 8.12 (1 H), 7.63 (1 H), 6.62 (1 H), 4.95-4.99 (1 H), 2.50 (3 H), 2.21-2.38 (2 H), 1.68-1.81 (1 H), 1.44-1.64 (4 H), 1.07-1.30 (4 H); m/z 367.0 (M+H)$^+$.

Example 70

(S)-3-cyclopentyl-N-(5-methylpyrazin-2-yl)-2-(3-(trifluoromethyl)-1H-pyrazol-1-yl)propanamide Formula (1A-5) wherein $R^4$ is

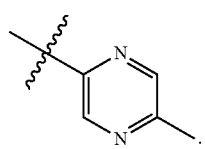 [SMILES: *c1cnc(C)cn1]

Example 70 was synthesized in an analogous manner to that of Example 68 from Intermediate I-9a1 and 2-amino-5-methylpyrazine. $^1$H NMR (400 MHz, CDCl$_3$) δ 9.31 (1 H), 8.94 (1H), 8.12 (1 H), 7.63 (1 H), 6.62 (1 H), 4.95-4.99 (1 H), 2.50 (3 H), 2.21-2.38 (2 H), 1.68-1.81 (1 H), 1.44-1.64 (4 H), 1.07-1.30 (4 H); m/z 368.0 (M+H)$^+$.

Examples 71-73 of Formula (1A-6) are provided below.

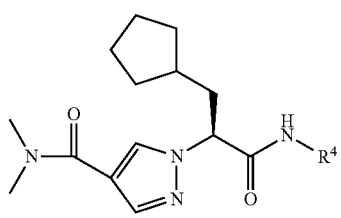
(1A-6)

Example 71

(S)-1-(3-cyclopentyl-1-(1-methyl-1H-pyrazol-3-ylamino)-1-oxopropan-2-yl)-N,N-dimethyl-1H-pyrazole-4-carboxamide Formula (1A-6) wherein $R^4$ is

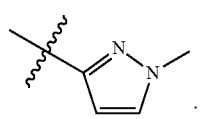 [SMILES: *c1ccn(C)n1]

Example 71 was synthesized in an analogous manner to that of Example 68 from Intermediate I-9a2 and 3-amino-1-methylpyrazole. $^1$H NMR (400 MHz, CDCl$_3$) δ 9.46 (1 H), 7.93 (1H), 7.82 (1 H), 7.17 (1H), 6.55 (1 H), 4.87-4.91 (1 H), 3.72 (3 H), 3.15 (3 H), 3.03 (3 H), 2.19-2.49 (2 H), 1.38-1.68 (7 H), (1 H), 1.08-1.17 (1 H), 0.97-1.02 (1 H); m/z 359.2 (M+H)$^+$.

Example 72

(S)-1-(3-cyclopentyl-1-(5-methylpyridin-2-ylamino)-1-oxopropan-2-yl)-N,N-dimethyl-1H-pyrazole-4-carboxamide Formula (1A-6) wherein $R^4$ is

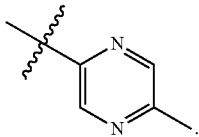 [SMILES: *c1cnc(C)cn1]

Example 72 was synthesized in an analogous manner to that of Example 68 from Intermediate I-9a2 and 2-amino-5-methylpyridine. $^1$H NMR (400 MHz, CDCl$_3$) δ 12.61 (1 H), 8.48 (1H), 8.17 (2 H), 8.03 (1 H), 7.79 (1 H), 5.28 (1 H), 3.24 (3 H), 3.08 (3 H), 2.43 (3 H), 2.16-2.32 (2 H), 1.44-1.77 (6 H), 1.26 (2 H), 1.08-1.14 (1 H); m/z 370.1 (M+H)$^+$.

Example 73

(S)-1-(3-cyclopentyl-1-(5-methylpyrazin-2-ylamino)-1-oxopropan-2-yl)-N,N-dimethyl-1H-pyrazole-4-carboxamide Formula (1A-6) wherein $R^4$ is

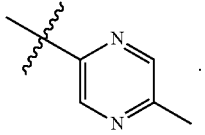 [SMILES: *c1cnc(C)cn1]

Example 73 was synthesized in an analogous manner to that of Example 68 from Intermediate I-9a2 and 2-amino-5-methylpyrazine. $^1$H NMR (400 MHz, CDCl$_3$) δ 9.61 (1 H), 9.32 (1H), 8.08 (1 H), 7.95 (1 H), 7.88 (1 H), 4.94-4.98 (1 H), 3.19 (3 H), 3.07 (3 H), 2.49 (3 H), 2.29-2.37 (2 H), 1.40-1.76 (7 H), 1.05-1.19 (2 H); m/z 371.1 (M+H)$^+$.

Examples 74-78 of Formula (1A-7) are provided below.

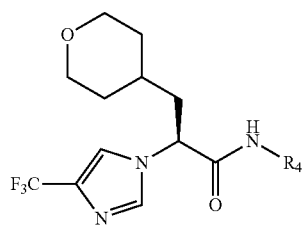

(1A-7)

Example 74

(S)—N-(5-methylpyrazin-2-yl)-3-(tetrahydro-2H-pyran-4-yl)-2-(4-(trifluoromethyl)-1H-imidazol-1-yl)propanamide Formula (1A-7) wherein $R^4$ is

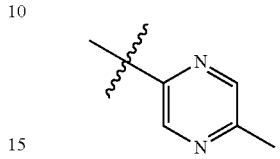

2-amino-5-methylpyrazine (Anichem LLC., Northbrunswick, N.J.) (48.2 mg, 0.44 mM) was weighed into an 8 dram Arqule vial and stirred in anhydrous toluene (0.5 mL). Trimethylaluminum solution (0.23 mL, 2.0M in toluene) was added, and the reaction was sealed and stirred at room temperature for 45 minutes. A 1 mL aliquot of dichloroethane was added to 63 mg (0.21 mmol) of Intermediate I-10h, the reaction was sealed and stirred at 80° C. The reaction was cooled, and the residue was diluted with dichloromethane and 0.5 M Rochelle salt, shaken, and allowed to stand for 90 minutes. The mixture was filtered through an Autovial filter to remove insoluble material. The organic layer was filtered through an Alltech filter and dried under nitrogen. Chromatographic (column: Phenomenex Luna (2) C18, 150×4.6 mm, 5μ (21.2×150 mm 5μ), gradient 0.1% formic acid in water and 0.1% formic acid in acetonitrile (5 to 95%) purification of the crude product to afford the title compound. $^1$H NMR (400 MHz, CDCl$_3$) δ 9.38 (1 H), 9.05 (1 H), 8.06 (1 H), 7.70 (1 H), 7.50 (1 H), 4.92 (1 H), 3.89-3.94 (2 H), 3.27-3.33 (2 H), 2.53 (3 H), 2.04-2.18 (2 H), 1.33-1.62 (5 H); m/z 384.2 (M+H)$^+$.

Example 75

(S)—N-(5-methylpyridin-2-yl)-3-(tetrahydro-2H-pyran-4-yl)-2-(4-(trifluoromethyl)-1H-imidazol-1-yl)propanamide Formula (1A-7) wherein $R^4$ is

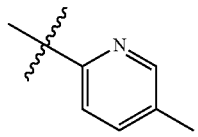

Example 75 was synthesized in an analogous manner to that of Example 74 from Intermediate I-10h and 2-amino-5-methylpyridine. $^1$H NMR (400 MHz, CDCl$_3$) δ 9.62 (1 H), 8.09-8.11 (1 H), 8.02 (1 H), 7.70 (1 H), 7.58-7.60 (1 H), 7.51 (1 H), 4.87-4.91 (1 H), 3.89-3.95 (2 H), 3.26-3.33 (2 H), 2.31 (3 H), 2.02-2.17 (2 H), 1.34-1.64 (5 H); m/z 383.2 (M+H)$^+$.

Example 76

(S)—N-(1-methyl-1H-pyrazol-3-yl)-3-(tetrahydro-2H-pyran-4-yl)-2-(4-(trifluoromethyl)-1H-imidazol-1-yl)propanamide Formula (1A-7) wherein $R^4$ is

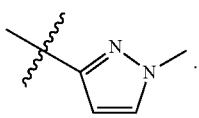 [SMILES: *c1ccn(C)n1]

Example 76 was synthesized in an analogous manner to that of Example 74 from Intermediate I-10h and 3-amino-1-methylpyrazole. $^1$H NMR (400 MHz, CD$_3$OD) δ 7.91 (1 H), 7.78 (1 H), 7.42 (1 H), 6.47 (1 H), 5.10-5.14 (1 H), 3.85-3.91 (2 H), 3.78 (3 H), 3.28-3.35 (2 H), 2.07-2.10 (2 H), 1.31-1.69 (5 H); m/z 372.2 (M+H)$^+$.

Example 77

(S)-3-(tetrahydro-2H-pyran-4-yl)-N-(thiazolo[5,4-b]pyridin-2-yl)-2-(4-(trifluoromethyl)-1H-imidazol-1-yl)propanamide Formula (1A-7) wherein $R^4$ is

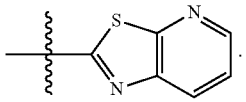 [SMILES: *c1nc2cccnc2s1]

Example 77 was synthesized in an analogous manner to that of Example 74 from Intermediate I-10h and thiazolo[5,4-b]pyridine-2-ylamine (AstaTech, Inc., Bristol, Pa.). $^1$H NMR (400 MHz, CDCl$_3$) δ 8.49-8.51 (1 H), 7.89-7.91 (1 H), 7.71 (1 H), 7.55 (1 H), 7.35-7.38 (1 H), 5.12-5.17 (1 H), 3.91-3.94 (2 H), 3.28-3.53 (2 H), 2.24-2.31 (1 H), 2.06-2.11 (1 H), 1.34-1.62 (5 H); m/z 426.1 (M+H)$^+$.

Example 78

(S)—N-(5-methoxythiazolo[5,4-b]pyridin-2-yl)-3-(tetrahydro-2H-pyran-4-yl)-2-(4-(trifluoromethyl)-1H-imidazol-1-yl)propanamide Formula (1A-7) wherein $R^4$ is

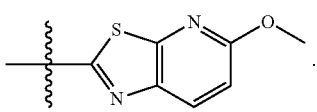 [SMILES: *c1nc2ccc(OC)nc2s1]

Example 78 was synthesized in an analogous manner to that of Example 74 from Intermediate I-10h and 5-methoxythiazolo[5,4-b]pyridin-2-amine (Maybridge, Tevillett, Cornwall, UK). $^1$H NMR (400 MHz, CDCl$_3$) δ 7.79-7.81 (1 H), 7.78 (1 H), 7.54 (1 H), 6.79-6.81 (1 H), 5.06-5.11 (1 H), 3.98 (3 H), 3.91-3.97 (2 H), 3.28-3.35 (2 H), 2.21-2.28 (1 H), 2.06-2.12 (1 H), 1.31-1.62 (5 H); m/z 456.1 (M+H)$^+$.

Examples 79-81 of Formula (1A-8) are provided below.

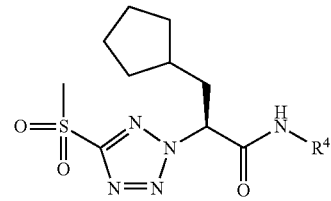

(1A-8)

Example 79

(S)-3-cyclopentyl-N-(1-methyl-1H-pyrazol-3-yl)-2-(5-(methylsulfonyl)-2H-tetrazol-2-yl)propanamide Formula (1A-8) wherein $R^4$ is

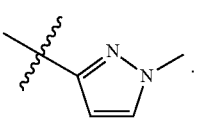 [SMILES: *c1ccn(C)n1]

3-Amino1-methylpyrazole (38.9 mg, 0.40 mmol) was stirred in anhydrous toluene (2 mL). Trimethylaluminum solution (0.21 mL, 2.0M in toluene) was added, and the reaction was stirred at room temperature for 35 minutes. A 2 mL aliquot of dichloroethane was added to 60 mg (0.20 mmol) of Intermediate I-11b. This solution was added and the stirred at 80° C. for 16 h. The reaction was cooled and stirred for several minutes with aqueous saturated Rochelle's salt. This was extracted twice with dichloromethane and the combined organics were dried over MgSO$_4$ and concentrated under reduced pressure. Chromatographic purification of the crude product afforded 13.5 mg of the title compound. $^1$H NMR (400 MHz, CDCl$_3$) δ 8.67 (1 H), 7.26 (1 H), 6.60 (1 H), 5.67 (1 H), 3.80 (3 H), 3.42 (3 H), 2.54-2.64 (1 H), 2.38-2.48 (1 H), 1.76-1.86 (1 H), 1.55-1.76 (4 H), 1.44-1.54 (2 H), 1.02-1.27 (2 H); m/z 366.4 (M−H)$^−$.

Example 80

(S)-3-cyclopentyl-N-(5-methylpyridin-2-yl)-2-(5-(methylsulfonyl)-2H-tetrazol-2-yl)propanamide, Formula (1A-8) wherein $R^4$

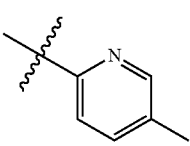

Example 80 was synthesized in an analogous manner to that of Example 79 from Intermediate I-11b and 2-amino-5-methylpyridine. $^1$H NMR (400 MHz, CDCl$_3$) δ 9.02 (1 H), 8.17 (1 H), 7.97 (1 H), 6.96 (1 H), 5.62-5.74 (1 H), 3.43 (3 H), 2.58-2.71 (1 H), 2.39-2.48 (1 H), 2.37 (3 H), 1.45-1.85 (7 H), 1.05-1.25 (2 H); m/z 379.5 (M+H)$^+$.

Example 81

(S)-3-cyclopentyl-N-(5-methylpyrazin-2-yl)-2-(5-(methylsulfonyl)-2H-tetrazol-2-yl)propanamide Formula (1A-8) wherein R⁴

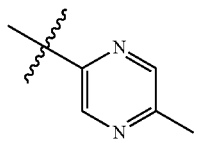

Example 81 was synthesized in an analogous manner to that of Example 79 from Intermediate I-11b and 2-amino-5-methylpyrazine. ¹H NMR (400 MHz, CDCl$_3$) δ 9.31 (1 H), 8.43 (1 H), 8.14 (1 H), 5.75 (1 H), 3.45 (3 H), 2.62-2.72 (1 H), 2.55 (3 H), 2.40-2.51 (1 H), 1.46-1.90 (7 H), 1.07-1.31 (2 H); m/z 378.4 (M−H)⁻.

Example 82

(2S)—N-(5-methylpyridin-2-yl)-3-(tetrahydrofuran-2-yl)-2-(4-(trifluoromethyl)-1H-imidazol-1-yl)propanamide, of Formula (1A-9)

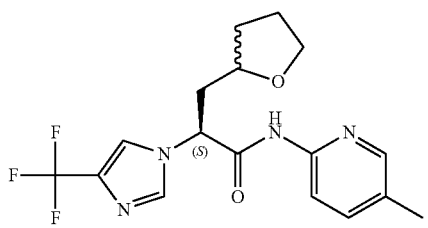

1A-9

To a solution of 5-methylpyridin-2-amine (205 mg, 1.9 mmol) in 4 mL of dimethoxyethane was added dimethylaluminum chloride (1.0 M in hexanes, 3.8 mL, 1.8 mmol). After the light yellow solution was stirred for 0.5 hours, a solution of intermediate (I-12e) (185 mg, 0.63 mmol) in 2.3 mL of dimethoxyethane was added into the mixture. The reaction was heated as a mixture at 90° C. overnight before cooling to room temperature. The crude reaction mixture was taken up in ethyl acetate and washed with 0.5M aqueous Rochelle's salt. The aqueous layer was re-extracted with ethyl acetate twice. The combined organic layers were dried over sodium sulfate, filtered and concentrated under reduced pressure. The crude residue was purified by silica gel chromatography (ISCO 12 g, 30-60% ethyl acetate/heptane) to afford the title compound as a yellow solid and as a mixture of diastereomers (85 mg, yield 36%). ¹H NMR (400 MHz, DMSO-d$_6$) δ 10.93 (1 H), 8.16-8.20 (1 H), 7.88-7.97 (3 H), 7.59-7.65 (1 H), 5.29-5.40 (1 H), 3.71-3.80 (1 H), 3.44-3.66 (2 H), 2.28-2.46 (1 H), 2.25 (3 H), 2.12-2.22 (1 H), 1.38-1.99 (6 H); m/z 369.1 (M+H)⁺.

Example 83

(S)—N-(5-methylpyridin-2-yl)-3-(1H-pyrazol-1-yl)-2-(4-(trifluoromethyl)-1H-imidazol-1-yl)propanamide, of Formula (1A-10)

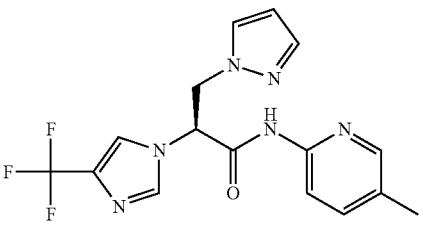

1A-10

5-Methylpyridin-2-amine (97 mg, 0.9 mmol) was weighed into an 8-dram Arqule vial and stirred in dry toluene (1.0 mL). Trimethylaluminum (0.44 mL, 2.0 M in toluene, 0.88 mmol) was added, and the reaction was sealed and stirred at room temperature for 45 minutes. Intermediate (I-13c) (116.3 mg, 0.40 mmol) in 1,2-dichloroethane (2.0 mL) was added, and the reaction was sealed and warmed to 80° C. for 16 hours. The reaction was cooled and shaken with 0.5M aqueous Rochelle salt solution (1 mL). Dichloromethane (1 mL) was added, and the mixture was stirred for 40 minutes. The mixture was suction filtered, and the organic phase of the filtrate was run through an Alltech filter and evaporated. The material was purified (Combi-flash, Redi-sep 40 g, 1:1 ethyl acetate/heptane gradient to 100% ethyl acetate), and the putative product fractions were combined and evaporated. TLC (5% methanol/dichloromethane) showed that the residue contained two components. The material was purified by silica prep TLC, developing with 6% methanol/dichloromethane. Three narrow, close together bands were scraped off and crushed, and the compounds were leached off with 1:1 ethyl acetate/methanol and filtered. The solvent was removed under a nitrogen stream. The residues were checked by LC-MS to locate the desired product mass. The material containing the product was purified by LC (Phenomenex Gemini C18 21.2×150 mm, 5 um, modifier 0.1% ammonium hydroxide, 95% water/5% acetonitrile linear gradient to 5% water/95% acetonitrile) to afford the title compound (19.2 mg, 0.053 mmol, 13%). ¹H NMR (400 MHz, CDCl$_3$) δ 8.06-8.08 (2 H), 7.55-7.60 (2 H), 7.42-7.45 (2 H), 7.13-7.14 (1 H), 6.16-6.17 (1 H), 5.47-5.51 (1 H), 4.86-4.91 (1 H), 4.54-4.59 (1 H), 2.31 (3 H); m/z 365.0 (M+H)⁺.

Examples 84-89 represented of Formula (1A-11) are provided below.

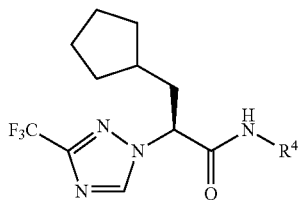
(1A-11)

Example 84

(S)-3-cyclopentyl-N-(pyrazin-2-yl)-2-(3-(trifluoromethyl)-1H-1,2,4-triazol-1-yl)propanamide Formula (1A-11) wherein $R^4$

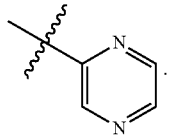 [SMILES: *c1cnccn1]

is Trimethylaluminum (2 M in heptane, 0.510 mL, 1.02 mmol) was added to a solution of 2-aminopyrazine (97 mg, 1.02 mmol) in dry toluene (4 mL) under argon at 0° C., and the resulting reaction mixture warmed to ambient temperature and stirred for 30 minutes. After this time, a solution of intermediate (I-15b) (99 mg, 0.34 mmol) in tetrahydrofuran (4 mL) was added dropwise to the reaction mixture and the reaction heated to reflux overnight. After cooling to ambient temperature, the reaction was quenched with the addition of ammonium chloride (aq.) (5 mL), and the product extracted with ethyl acetate (2×10 mL), washed with brine (10 mL), dried over MgSO$_4$, filtered and the solvent removed under vacuum. Purification was then achieved by flash chromatography (2:1 hexane/ethyl acetate) to afford the title compound as a colorless viscous oil (81 mg, 67% yield). $^1$H NMR (400 MHz, CDCl$_3$) δ 9.46 (1 H), 8.63 (1 H), 8.41 (1 H), 8.38 (1 H), 8.29 (1 H), 5.10 (1 H), 2.39-2.27 (2 H), 1.66-1.79 (1 H), 1.75-1.49 (6 H), 1.27-1.10 (2 H); m/z 354.9 (M+H)$^+$.

Example 85

(S)-3-cyclopentyl-N-(5-methylpyridin-2-yl)-2-(3-(trifluoromethyl)-1H-1,2,4-triazol-1-yl)propanamide Formula (1A-11) wherein $R^4$ is

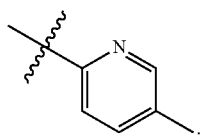 [SMILES: *c1ccc(C)cn1]

Example 85 was synthesized in an analogous manner to that of Example 84 from Intermediate I-15b and 2-amino-5-methylpyridine. $^1$H NMR (400 MHz, CDCl$_3$) δ 8.54 (1 H), 8.41 (1 H), 8.13 (1 H), 8.01 (1 H), 7.53 (1 H), 5.04 (1 H), 2.31-2.27 (2 H), 2.30 (3 H), 1.83-1.77 (1 H), 1.75-1.58 (4 H), 1.54-1.47 (2 H), 1.23-1.08 (2 H); m/z 367.9 (M+H)$^+$.

Example 86

(S)-benzyl 6-(3-cyclopentyl-2-(3-(trifluoromethyl)-1H-1,2,4-triazol-1-yl)propanamido)nicotinate Formula (1A-11) wherein $R^4$ is

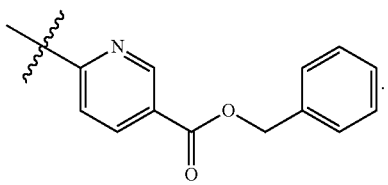 [SMILES: *c1ccc(C(=O)OCc2ccccc2)cn1]

Intermediate (I-15c) (180 mg, 0.65 mmol) was stirred in dry dichloromethane (5 mL) at room temperature under nitrogen. One drop of dimethylformamide was added, followed by oxalyl chloride (0.12 mL, 1.3 mmol). After bubbling had subsided, the reaction was left stirring for 90 minutes and then evaporated. The residue was re-dissolved in 1,2-dichloroethane and re-evaporated twice to remove unreacted oxalyl chloride, and then the residue was dissolved in dry dichloromethane (5 mL). Intermediate (I-28a) (180 mg, 0.789 mmol) and pyridine (0.11 mL, 1.36 mmol) were added to the acid chloride solution, and the reaction was stirred for 18 hours. The reaction was diluted with dichloromethane and water. The organic layer was washed with brine, dried over sodium sulfate, filtered, evaporated, and the residue was purified by silica gel chromatography, using a 12 g pre-packed column, eluting with 25% ethyl acetate/heptane. The product fractions were combined, evaporated, and dried under high vacuum to afford the title compound (262 mg, 0.537 mmol, 83%) as a white glass. $^1$H NMR (400 MHz, CDCl$_3$) δ 8.95 (1 H), 8.82 (1 H), 8.39 (1 H), 8.32-8.34 (1 H), 8.17-8.19 (1 H), 7.34-7.44 (5 H), 5.36 (2 H), 5.08-5.11 (1 H), 2.28-2.33 (2 H), 1.49-1.81 (7 H), 1.08-1.21 (2 H); m/z 488.0 (M+H)$^+$.

Example 87

(S)-ethyl 2-(3-(3-cyclopentyl-2-(3-(trifluoromethyl)-1H-1,2,4-triazol-1-yl)propanamido)-1H-pyrazol-1-yl)acetate Formula (1A-11) wherein $R^4$ is

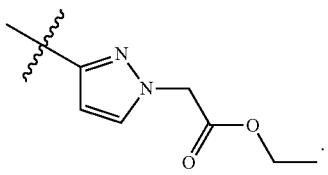 [SMILES: *c1ccn(CC(=O)OCC)n1]

Intermediate (I-15c) (180 mg, 0.65 mmol) was stirred in dry dichloromethane (5 mL) at room temperature under nitrogen. One drop of dimethylformamide was added, followed by oxalyl chloride (0.12 mL, 1.3 mmol). After bubbling subsided, the reaction was left stirring for 90 minutes and then evaporated. The residue was re-dissolved in 1,2-dichloroethane and re-evaporated twice to remove unreacted oxalyl chloride, and then taken up in dry dichloromethane (5.0 mL). Ethyl 2-(3-amino-1H-pyrazol-1-yl)acetate hydrochloride (Oakwood Products, Inc., West Columbia, S.C.) (160 mg, 0.78 mmol) and pyridine (0.16 mL, 2.0 mmol) were added, and the reaction was stirred for 18 hours. The reaction was diluted with dichloromethane and water, and the organic layer was washed with brine, dried over sodium sulfate, and evaporated. The residue was purified by silica gel chromatography, using a 12 g pre-packed column, eluting with 25% ethyl acetate/heptane with a linear gradient to 50% ethyl acetate. The product fractions were combined, evaporated, and dried under high vacuum to afford the title compound (174 mg, 0.406 mmol, 62%) as a white glass. $^1$H NMR (400 MHz, CDCl$_3$) δ 8.48 (1 H), 8.37 (1 H), 7.36 (1 H), 6.72 (1 H), 4.99-5.03 (1 H), 4.77 (2 H), 4.19-4.25 (2 H), 2.20-2.30 (2 H), 1.46-1.81 (7 H), 1.25-1.29 (3 H), 1.04-1.22 (2 H); m/z 429.0 (M+H)$^+$.

Example 88

(S)-6-(3-cyclopentyl-2-(3-(trifluoromethyl)-1H-1,2,4-triazol-1-yl)propanamido)nicotinic acid Formula (1A-11) wherein R$^4$ is

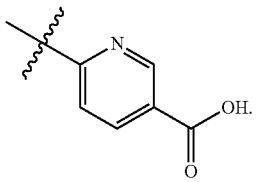 [SMILES: *c1ccc(C(=O)O)cn1]

The compound of Example 86 (262 mg, 0.537 mmol) was dissolved in ethyl acetate (4 mL) and ethanol (6 mL) in a small Parr bottle. 10% Palladium on carbon (40 mg) was added, and the reaction was shaken under 50 psi hydrogen for 2 hours. The mixture was filtered, evaporated, and dried under high vacuum at 50° C. to afford the title compound (176.3 mg, 0.44 mmol, 82%) as a white glass. $^1$H NMR (400 MHz, CD$_3$OD) δ 8.88-8.90 (2 H), 8.29-8.32 (1 H), 8.16-8.18 (1 H), 5.42-5.47 (1 H), 2.24-2.36 (2 H), 1.49-1.80 (7 H), 1.28-1.33 (1 H), 1.14-1.17 (1 H); m/z 396.0 (M–H)$^-$.

Example 89

(S)-2-(3-(3-cyclopentyl-2-(3-(trifluoromethyl)-1H-1,2,4-triazol-1-yl)propanamido)-1H-pyrazol-1-yl)acetic acid Formula (1A-11) wherein R$^4$ is

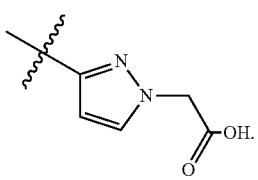 [SMILES: *c1ccn(CC(=O)O)n1]

The compound of Example 87 (174 mg, 0.406 mmol) and lithium hydroxide (57.4 mg, 1.34 mmol) were stirred at room temperature in tetrahydrofuran (2 mL), methanol (2 mL) and water (2 mL) for 2 hours. The mixture was concentrated, and water and 1N HCl were added to reach approximately pH 4. A dense solid crashed out. Ethyl acetate was added, and the organic layer was washed with brine and dried over sodium sulfate. The mixture was filtered, evaporated, and dried under high vacuum to afford the title compound (160 mg, 0.40 mmol, 99%) as a white glass. $^1$H NMR (400 MHz,CDCl$_3$) δ 10.21 (1 H), 8.40 (1 H), 7.35 (1 H), 6.78 (1 H), 5.03-5.07 (1 H), 4.75 (2 H), 2.03-2.24 (2 H), 1.41-1.75 (7 H), 1.01-1.26 (2 H); m/z 399.0 (M–H)$^-$.

Example 90

(S)-6-(3-cyclohexyl-2-(4-(trifluoromethyl)-1H-imidazol-1-yl)propanamido)nicotinic acid, of Formula (1A-12)

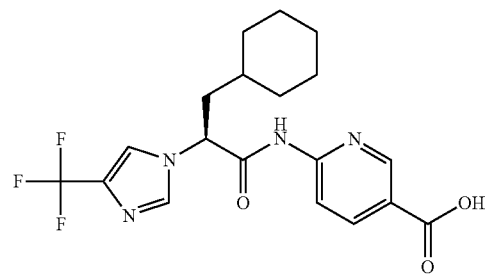

Intermediate (I-16e) (0.145 mg, 290 mmol) was taken up in 30 mL of methanol and was injected onto an H-Cube™. Hydrogenation occurred under a continuous flow of H$_2$ on a 10% Pd/C cartridge at a flow rate of 1 mL per min. The filtrate was collected and concentrated to afford the title compound. $^1$H NMR (400 MHz, CD$_3$OD) δ 8.90-8.89 (1 H), 8.32-8.29 (1 H), 8.20-8.17 (1 H), 7.93 (1 H), 7.81 (1 H), 5.28-5.24 (1 H), 2.08-2.04 (2 H), 1.84-1.81 (1 H), 1.73-1.63 (4 H), 1.18-1.16 (3 H), 1.07-0.99 (3 H); m/z 411 (M+H)$^+$.

Examples 91-92 of Formula (1A-13) are provided below.

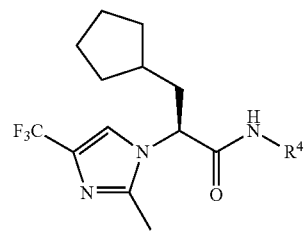

Example 91

(S)-3-cyclopentyl-2-(2-methyl-4-(trifluoromethyl)-1H-imidazol-1-yl)-N-(5-methylpyridin-2-yl)propanamide Formula (1A-13) wherein R$^4$ is

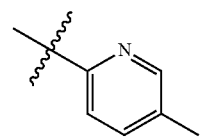

5-methylpyridin-2-amine (96 mg, 0.88 mmol) was taken up in 4 mL of dimethoxyethane and cooled to 0° C. Dimethylaluminium chloride (1.48 mmol, 1M in hexane) was added dropwise. The resulting mixture was warmed up to ambient temperature and stirred for 30 min. A solution of intermediate (I-17a) (90 mg, 0.3 mmol) in dimethoxyethane (2 mL) was then added to the activated amine solution via canula. The combined solution was heated to reflux overnight. The reaction was cooled to room temperature and slowly quenched by the dropwise addition of aqueous Rochelle's salt (concentrated, 10 mL). The mixture was stirred for 20 minutes before separating the layers. The organic layer was washed with aqueous Rochelle's salt (10 mL) and then brine (30 mL), dried over magnesium sulfate, and concentrated in vacuo. The crude product was purified by column chromatography (silica gel, gradient of ethyl acetate from 20-100% in heptane) to afford the title compound in 11% yield. $^1$H NMR (400 MHz, CDCl$_3$) δ 8.19 (1H), 7.96-8.10 (2 H), 7.53 (1 H), 7.46 (1H), 4.64 (1 H), 2.42 (3 H), 2.25-2.32 (3 H), 2.14-2.25 (1 H), 2.00-2.13 (1 H), 1.43-1.78 (7 H), 1.04-1.30 (2 H); m/z 381.4 (M+H)$^+$.

Example 92

(S)-6-(3-cyclopentyl-2-(2-methyl-4-(trifluoromethyl)-1H-imidazol-1-yl)propanamido)nicotinic acid Formula (1A-13) wherein R$^4$ is

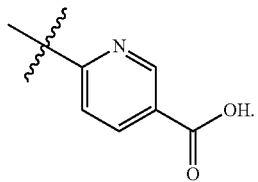 [SMILES: *c1ccc(C(=O)O)cn1]

Intermediate (I-17b) was dissolved in methanol (2 mL) and then hydrogenated with an H-Cube™ at full H$_2$ and 1 mL/min on a Pd-C cartridge. TLC (10% methanol/dichloromethane) showed most of the starting material had reacted. The reaction solution was concentrated and the crude material was purified by silica gel chromatography (4 g column, 0-15% methanol in dichloromethane) to afford the title compound. $^1$H NMR (400 MHz, CDCl$_3$) δ 11.73 (1 H), 9.01 (1 H), 8.54 (2 H), 7.58 (1 H), 5.04 (1 H), 2.54 (3 H), 2.17-2.31 (1 H), 2.03-2.17 (1 H), 1.76-1.91 (2 H), 1.45-1.74 (6 H), 1.27-1.44 (1 H), 1.07-1.24 (1 H); m/z 411.4 (M+H)$^+$.

Examples 93-95 of Formula (1A-14) are provided below.

(1A-14)

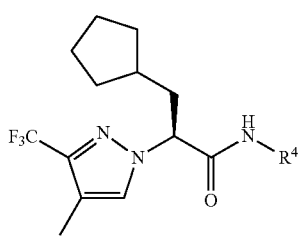

Example 93

(S)-3-cyclopentyl-2-(4-methyl-3-(trifluoromethyl)-1H-pyrazol-1-yl)-N-(5-methylpyridin-2-yl)propanamide Formula (1A-14) wherein R$^4$ is

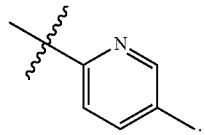 [SMILES: *c1ccc(C)cn1]

5-methylpyridin-2-amine (144 mg, 1.33 mmol) was taken up in 4 mL of dimethoxyethane and cooled to 0° C. Dimethylaluminium chloride (2.22 mmol, 1M in hexane) was added dropwise. The resulting mixture was warmed up to ambient temperature and stirred for 30 min. A solution of intermediate (I-18a) (135 mg, 0.44 mmol) in dimethoxyethane (2 mL) was then added to the activated amine solution via canula. The combined solution was heated to reflux overnight. The reaction was cooled to room temperature and slowly quenched by the dropwise addition of aqueous Rochelle's salt (concentrated, 10 mL). The mixture was stirred for 20 minutes before separating the layers. The organic layer was washed with aqueous Rochelle's salt (10 mL), and then brine (30 mL), dried over magnesium sulfate, and concentrated in vacuo. The crude product was purified by column chromatography (silica gel, gradient of ethyl acetate from 20-100% in heptane) to afford the title compound in 41% yield. $^1$H NMR (400 MHz, CDCl$_3$) δ 8.56 (1H), 8.06-8.11 (1 H), 7.99 (1 H), 7.45-7.50 (1 H), 7.39 (1 H), 4.84 (1 H), 3.66-3.74 (1 H), 2.16-2.33 (5 H), 2.13-2.16 (3 H), 1.42-1.84 (6 H), 1.01-1.21 (2 H); m/z 381.4 (M+H)$^+$.

Example 94

(S)-benzyl 6-(3-cyclopentyl-2-(4-methyl-3-(trifluoromethyl)-1H-pyrazol-1-yl)propanamido)nicotinate Formula (1A-14) wherein R$^4$ is

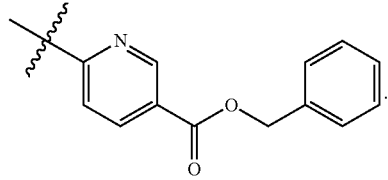 [SMILES: *c1ccc(C(=O)OCc2ccccc2)cn1]

Intermediate (I-18b) (65 mg, 0.22 mmol) was stirred in dry dichloromethane (5 mL) at room temperature under nitrogen. One drop of dimethylformamide was added, followed by oxalyl chloride (0.04 mL, 0.46 mmol). After bubbling subsided, the reaction was stirred for 90 minutes and then evaporated. The residue was re-dissolved in 1,2-dichloroethane and re-evaporated twice to remove unreacted oxalyl chloride, and then the residue was taken up in dry dichloromethane (2.5 mL). Intermediate (I-28a) (61.4 mg, 0.269 mmol) and pyridine (0.048 mL, 0.48 mmol) were added, and the reaction was left to stir for 18 hours. The solvent was evaporated and the residue was purified by silica gel chromatography, using a pre-packed 12 g column, eluting with 10% ethyl acetate/ heptane with a linear gradient to 50% ethyl acetate. The product fractions were combined, evaporated, and dried under high vacuum to afford the title compound (68.4 mg, 0.14 mmol, 62%) as a white glass. $^1$H NMR (400 MHz, CDCl$_3$) δ 9.10 (1 H), 8.93 (1 H), 8.28-8.31 (1 H), 8.18-8.20 (1 H), 7.33-7.43 (6 H), 5.33 (2 H), 4.87-4.91 (1 H), 2.16-2.35 (5 H), 1.46-1.79 (7 H), 1.05-1.20 (2 H); m/z 500.9 (M+H)$^+$.

Example 95

(S)-6-(3-cyclopentyl-2-(4-methyl-3-(trifluoromethyl)-1H-pyrazol-1-yl)propanamido)nicotinic acid Formula (1A-14) wherein R$^4$ is

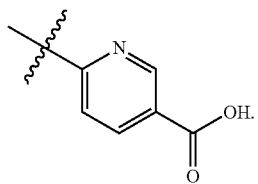

The compound of Example 94 (68 mg, 0.14 mmol) was dissolved in ethyl acetate (2 mL) and ethanol (4 mL) in a small Parr bottle. 10% Palladium on carbon (20 mg) was added, and the reaction was shaken under 30 psi hydrogen for 90 minutes. The mixture was filtered, evaporated, and dried under high vacuum to afford the title compound (47 mg, 0.11 mmol, 82%) as a clear glass. $^1$H NMR (400 MHz, CD$_3$OD) δ 8.88 (1 H), 8.28-8.30 (1 H), 8.16-8.18 (1 H), 7.77 (1 H), 5.19-5.23 (1 H), 2.15-2.29 (5 H), 1.45-1.83 (7 H), 1.08-1.30 (2 H); m/z 410.9 (M+H)$^+$.

Example 96

(S)-3-cyclopentyl-2-(3-methyl-4-(trifluoromethyl)-1H-pyrazol-1-yl)-N-(5-methylpyridin-2-yl)propanamide, of Formula (1A-15)

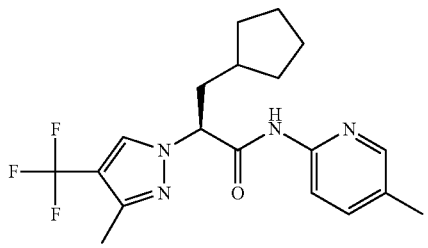

To a solution of 5-methylpyridin-2-amine (63.6 mg, 0.59 mmol) in 1.4 mL of dimethoxyethane was added dimethylaluminum chloride (1.0M in hexanes, 1.2 mL, 1.2 mmol). After stirring for 1 hour at 0° C., it was poured into a solution of intermediates (I-20b) and (I-20c) (89.4 mg, 0.29 mmol, combined) in 1.5 mL of dimethoxyethane. The mixture was heated at reflux for 3 h before cooling and concentrating. The residue was taken up in dichloromethane and stirred with saturated aqueous Rochelle's salts for 1 hour. The layers were separated and the aqueous layer was reextracted with dichloromethane twice. The combined organic layer was dried over sodium sulfate, filtered and concentrated. The crude material was purified by silica gel chromatography (ISCO 12 g, 30-60% ethyl acetate/heptane) to afford Example 96 and Example 97. $^1$H NMR (400 MHz, CDCl$_3$) δ 9.18 (1 H), 8.10-8.14 (1 H), 8.02 (1 H), 7.73 (1 H), 7.49 (1 H), 4.73-4.82 (1 H), 2.40 (3 H), 2.27 (3 H), 2.24-2.27 (1 H), 2.13-2.22 (1 H), 1.37-1.81 (5 H), 1.01-1.29 (4 H); m/z 381.0 (M+H)$^+$.

Example 97

(S)-3-cyclopentyl-2-(5-methyl-4-(trifluoromethyl)-1H-pyrazol-1-yl)-N-(5-methylpyridin-2-yl)propanamide of Formula (1A-16)

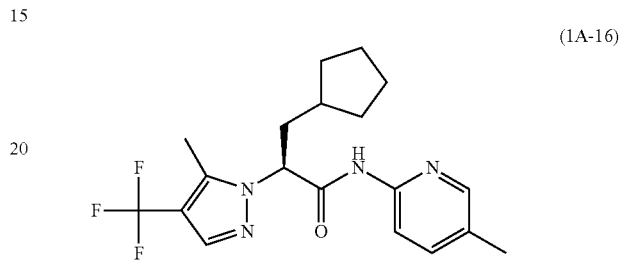

Prepared by the reaction described above for Example 96 to provide the title compound. $^1$H NMR (400 MHz, CDCl$_3$) δ 9.24 (1 H), 8.08 (1 H), 8.01 (1 H), 7.84 (1 H), 7.48 (1 H), 4.80 (1 H), 2.42-2.51 (1 H), 2.41 (3 H), 2.26 (3 H), 2.14-2.24 (1 H), 1.42-1.76 (5 H), 0.97-1.32 (4 H); m/z 380.9 (M+H)$^+$.

BIOLOGICAL ASSAY

Full-length glucokinase (beta cell isoform) was His-tagged at N-terminus and purified by a Ni column followed by size exclusion chromatography. A 320 mL column was packed in house using Superdex75 (Amersham Pharmacia, Carlsbad, Calif.) preparation grade resin. Glucose was obtained from Calbiochem (San Diego, Calif.) and other reagents were purchased from Sigma-Aldrich (St. Louis, Mo.).

All assays were performed in a Corning 384-well plate using Spectramax PLUS spectrophotometer (Molecular Devices, Sunnyvale, Calif.) at room temperature. The final assay volume was 40 ∥L. The buffer conditions used in this assay were as follows: 50 mM HEPES, 5 mM glucose, 2.5 mM ATP, 3.5 mM MgCl$_2$, 0.7 mM NADH, 2 mM dithiothreitol, 1 unit/mL pyruvate kinase/lactate dehydrogenase (PK/LDH), 0.2 mM phosphoenolpyruvate, and 25 mM KCl. The buffer pH was 7.1. The test compound in dimethylsulfoxide solution was added to the buffer and mixed by a plate shaker for 7.5 minutes. The final concentration of dimethylsulfoxide introduced into the assay was 0.25%.

Glucokinase was added to the buffer mixture to initiate the reaction in the presence and absence of compound. The reaction was monitored by absorbance at 340 nm due to the depletion of NADH. The initial reaction velocity was measured by the slope of a linear time course of 0-300 seconds. The percentage of maximum activation was calculated by the following equation:

% Maximum Activation=($Va/Vo$−1)×100;

wherein each of Va and Vo is defined as the initial reaction velocity in the presence and absence of the tested compound, respectively.

To determine the EC$_{50}$ (half maximal effective concentration) and % maximum activation, compounds were serially diluted in dimethylsulfoxide by 3-fold. The glucokinase activities were measured as a function of compound concentrations. The data were fitted to the equation below to obtain the $EC_{50}$ and % max activation values:

$$Va/Vo = 1 + (\% \text{ max activation}/100)/(1 + EC_{50}/\text{compound concentration})$$

Beta Cell Glucokinase His-Tag Purification
Growth and Induction Conditions:

BL21(DE3) cells (Invitrogen Corporation, Carlsbad, Calif.) containing pBCGK (C or N His) vector were grown at 37° C. (in 2× YT) until the OD600 was between 0.6-1.0. Expression was induced by addition of isopropylthiogalactoside to a final concentration of 0.1-0.2 mM to the cells which were then incubated overnight at 23° C. The next day, cells were harvested via centrifugation at 5000 rpm for 15 minutes at 4° C. The cell pellet was stored at −80° C. for future purification.

Purification:

A Ni-NTA (Quigan, Germantown, Md.) column (15-50 mL) was used for separation. Two buffers were prepared, 1) a lysis/nickel equilibration and wash buffer and 2) a nickel elution buffer. The lysis/equilibration/wash buffer was prepared as such: 25 mM HEPES buffer at pH 7.5, 250 mM NaCl, 20 mM imidazole, and 14 mM β-mercaptoethanol as final concentrations. The elution buffer was prepared as such: 25 mM HEPES at pH 7.5, 250 mM NaCl, 400 mM imidazole, and 14 mM β-mercaptoethanol as final concentrations. The buffers were each filtered with a 0.22 μm filter prior to use. The cell pellet (1 L culture) was resuspended in 300 mL of the lysis/equilibration buffer. The cells were then lysed (3 times) with a Microfluidics Model 110Y microfluidizer (Microfluidics Corporation, Newton, Mass.). The slurry was centrifuged with a Beckman Coulter Model LE-80K ultracentrifuge (Beckman Coulter, Fullerton, Calif.) at 40,000 rpm for 45 minutes at 4° C. The supernatant was transferred to a chilled flask. A volume of 20 μl was saved for gel analysis. A Pharmacia AKTA (GMI, Inc., Ramsey, Minn.) purification system was used for separation. The prime lines were purged with lysis/equilibration buffer. The Ni-NTA column was equilibrated with 200 mL of the lysis/equilibration buffer at a flow rate of 5 mL/minute. The supernatant was loaded over the column at 4 mL/minute and the flow-through was collected in a flask. The unbound proteins were washed with lysis/equilibration buffer at a flow rate of 5 mL/minute until the ultraviolet reaches baseline. The protein was then eluted from the column with the imidazole elution buffer via imidazole gradient 20 mM to 400 mM over 320 mL. The column was then stripped of any additional protein with 80 mL of the elution buffer. The elution fractions were each 8 mL, for a total yield of 50 samples. Fractions were analyzed by sodium dodecyl sulfate polyacrylamide (SDS-PAGE) and the fractions containing protein of interest were pooled and concentrated to 10 mL using ultrafiltration cell with a 10,000 molecular weight cut-off (MWCO) Millipore membrane (Sigma-Aldrich, St. Louis, Mo.) under nitrogen gas (60 psi). Protein was further purified by size exclusion chromatography (SEC) using a Sedex 75 evaporative light scattering detector (320 mL) (Amersham Pharmacia, Uppsala, Sweden). SEC was equilibrated with 450 mL sizing buffer containing 25 mM HEPES pH 7.0, 50 mM NaCl, and 5 mM dithiothreitol. Concentrated protein was then loaded over SEC and elution with 400 mL sizing buffer was performed overnight at 0.5 mL/minute. The elution fractions were 5 mL each. The fractions were analyzed by SDS-PAGE and protein containing fractions were pooled. Concentration was measured using Bradford Assay/BSA Standard. Purified protein was stored in small aliquots at −80° C.

Biological Data

The $EC_{50}$ (μM) and percent maximum activation data for Examples 1-97 obtained from the biological procedures as defined above are presented in the table below as a single value or range where the sample size (N) is >1.

Biological Data Table: $EC_{50}$ and Maximum Activation Percent as Determined by the Methods described above.

| Example | $EC_{50}$ (μM) | Maximum Activation (%) | N |
|---|---|---|---|
| 1 | 0.3-0.6 | 38-50 | 2 |
| 2 | 9.0-16.5 | 84-90 | 4 |
| 3 | 0.7-1.9 | 15-23 | 3 |
| 4 | 0.9-2.2 | 57-90 | 4 |
| 5 | >100 | na | 2 |
| 6 | 4.8-5.6 | 70-76 | 2 |
| 7 | 3.5-6.0 | 39-40 | 2 |
| 8 | 3.8 | 100 | 1 |
| 9 | 55 | 174 | 1 |
| 10 | 4.8 | 56 | 1 |
| 11 | 32 | 110 | 1 |
| 12 | >100 | na | 1 |
| 13 | 32 | 100 | 1 |
| 14 | 11 | 122 | 1 |
| 15 | 60 | 89 | 1 |
| 16 | 1.9 | 48 | 1 |
| 17 | 8.2 | 23 | 1 |
| 18 | 15.7 | 24 | 1 |
| 19 | 1.3-1.7 | 33-39 | 2 |
| 20 | 7.2 | 80 | 1 |
| 21 | 2.9 | 65 | 1 |
| 22 | 25 | 144 | 1 |
| 24 | 7.0 | 145 | 1 |
| 25 | 3.9 | 116 | 1 |
| 26 | 33 | 89 | 1 |
| 27 | 22 | 120 | 1 |
| 28 | >100 | na | 1 |
| 29 | 17 | 112 | 1 |
| 30 | 10 | 100 | 1 |
| 31 | 11 | 125 | 1 |
| 33 | 16 | 136 | 1 |
| 34 | 62 | 236 | 1 |
| 35 | 0.8 | 100 | 1 |
| 36 | 23 | 125 | 1 |
| 38 | 2.3 | 160 | 1 |
| 43 | 2.9-3.5 | 147-166 | 2 |
| 44 | 1.1 | 111 | 1 |
| 45 | 2 | 161 | 1 |
| 48 | 0.2-0.7 | 144-223 | 6 |
| 49 | 2.2 | 168 | 1 |
| 50 | 2.6-4.2 | 121-140 | 2 |
| 51 | 6.7-8.8 | 90-113 | 2 |
| 52 | 0.4 | 110 | 1 |
| 54 | 28 | 123 | 1 |
| 56 | 5.2 | 167 | 1 |
| 57 | 8.2 | 138 | 1 |
| 58 | 3.4 | 129 | 1 |
| 59 | 14 | 81 | 1 |
| 60 | 4.6 | 112 | 1 |
| 61 | 5.1 | 123 | 1 |
| 62 | >50 | na | 1 |
| 64 | 4.2 | 163 | 1 |
| 65 | 17 | 84 | 1 |
| 66 | 1.6 | 131 | 1 |
| 67 | 2.8 | 104 | 1 |
| 68 | >100 | na | 1 |
| 69 | 5.5 | 90 | 1 |
| 70 | 24 | 124 | 1 |
| 71 | >30 | na | 1 |
| 72 | >100 | na | 1 |
| 73 | >100 | na | 1 |
| 74 | 8.7 | 115 | 1 |
| 75 | 0.8-2.0 | 51-78 | 4 |
| 76 | 18 | 138 | 1 |
| 77 | 18 | 139 | 1 |
| 78 | 4.2-4.4 | 109-114 | 2 |
| 79 | 40 | 99 | 1 |

-continued

| Example | EC$_{50}$ (μM) | Maximum Activation (%) | N |
|---|---|---|---|
| 80 | 32 | 86 | 1 |
| 81 | >50 | na | 1 |
| 82 | 5.0 | 115 | 1 |
| 83 | >100 | na | 1 |
| 84 | 10 | 171 | 1 |
| 85 | 0.8-1.0 | 125-147 | 2 |
| 88 | 0.7 | 150 | 1 |
| 89 | 45 | 183 | 1 |
| 90 | 0.2-0.3 | 120-138 | 2 |
| 91 | 0.4 | 120 | 1 |
| 92 | 0.4-1.2 | 158-168 | 2 |
| 93 | 4.0-5.4 | 92-95 | 2 |
| 95 | 8.0 | 128 | 1 |
| 96 | 2.8 | 123 | 1 |
| 97 | 28 | 136 | 1 |

We claim:

1. The compound (S)-6-(2-(4-(Cyclobutylsulfonyl)-1H-imidazol-1-yl)-3-cyclopentylpropanamido)nicotinic acid or a pharmaceutically acceptable salt thereof.

2. A pharmaceutical composition comprising a therapeutically effective amount of the compound according to claim 1 and a pharmaceutically acceptable excipient, diluent, or carrier.

3. A compound of structure

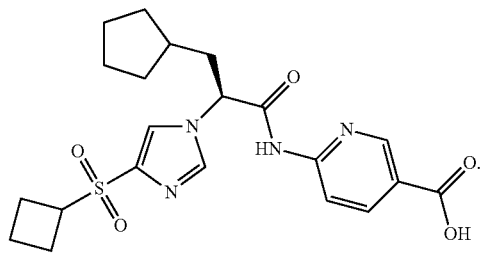 [SMILES: O=C(O)c1ccc(NC(=O)[C@H](CC2CCCC2)n2cnc(S(=O)(=O)C3CCC3)c2)nc1]

* * * * *